(12) United States Patent
Slusher et al.

(10) Patent No.: US 11,712,435 B2
(45) Date of Patent: Aug. 1, 2023

(54) MEBENDAZOLE PRODRUGS WITH ENHANCED SOLUBILITY AND ORAL BIOAVAILABILITY

(71) Applicants: The Johns Hopkins University, Baltimore, MD (US); Institute of Organic Chemistry and Biochemistry AS CR v.v.i., Prague (CZ)

(72) Inventors: Barbara Slusher, Baltimore, MD (US); Rana Rais, Baltimore, MD (US); Gregory Riggins, Baltimore, MD (US); Pavel Majer, Prague (CZ); Tomas Tichy, Prague (CZ); Jan Vavra, Prague (CZ); Andrej Jancarik, Prague (CZ); Lukas Tenora, Prague (CZ)

(73) Assignees: THE JOHNS HOPKINS UNIVERSITY, Baltimore, MD (US); INSTITUTE OF ORGANIC CHEMISTRY & BIOCHEMISTRY AS CR V.V.I., Prague (CZ)

( * ) Notice: Subject to any disclaimer, the term of this patent is extended or adjusted under 35 U.S.C. 154(b) by 0 days.

(21) Appl. No.: 16/967,924

(22) PCT Filed: Feb. 8, 2019

(86) PCT No.: PCT/US2019/017291
§ 371 (c)(1),
(2) Date: Aug. 6, 2020

(87) PCT Pub. No.: WO2019/157338
PCT Pub. Date: Aug. 15, 2019

(65) Prior Publication Data
US 2021/0205271 A1 Jul. 8, 2021

Related U.S. Application Data

(60) Provisional application No. 62/627,810, filed on Feb. 8, 2018.

(51) Int. Cl.
| | | |
|---|---|---|
| *A61K 31/4184* | (2006.01) |
| *A61K 31/685* | (2006.01) |
| *A61K 31/7056* | (2006.01) |
| *C07D 235/32* | (2006.01) |
| *C07D 405/12* | (2006.01) |
| *C07F 9/6506* | (2006.01) |
| *A61P 35/00* | (2006.01) |
| *C07H 13/12* | (2006.01) |
| *A61K 31/675* | (2006.01) |
| *A61K 45/06* | (2006.01) |
| *C07H 15/26* | (2006.01) |

(52) U.S. Cl.
CPC ........ *A61K 31/4184* (2013.01); *A61K 31/675* (2013.01); *A61K 31/685* (2013.01); *A61K 31/7056* (2013.01); *A61K 45/06* (2013.01); *A61P 35/00* (2018.01); *C07D 235/32* (2013.01); *C07D 405/12* (2013.01); *C07F 9/65068* (2013.01); *C07H 13/12* (2013.01); *C07H 15/26* (2013.01)

(58) Field of Classification Search
CPC . C07D 325/32; C07D 405/12; C07F 9/65068; A61K 31/685; A61K 31/4184
See application file for complete search history.

(56) References Cited

U.S. PATENT DOCUMENTS

| | | | |
|---|---|---|---|
| 11,110,079 B2 * | 9/2021 | Riggins | .............. A61K 9/50 |
| 2008/0293796 A1 * | 11/2008 | Chow | .............. A61K 9/1075 |
| | | | 514/395 |
| 2009/0131369 A1 | 5/2009 | Chassaing | |
| 2013/0017266 A1 | 1/2013 | Ogino et al. | |
| 2021/0369679 A1 * | 12/2021 | Riggins | .............. A61K 45/06 |

FOREIGN PATENT DOCUMENTS

| | | | |
|---|---|---|---|
| WO | WO 93/02058 | 2/1993 | |
| WO | WO-9302059 A1 * | 2/1993 | ............ A61P 33/00 |
| WO | WO 2000/041669 | 7/2000 | |
| WO | WO 2016/127168 | 8/2016 | |

OTHER PUBLICATIONS

Idhe et al. "Chemotherapy of Lung Cancer" The New England Journal of Medicine vol. 327 No. 20 pp. 1434-1441 (Year: 1992).*
Nygren et al., "Repositioning of the anthelmintic drug mebendazole for the treatment for colon cancer" J Cancer Res Clin Oncol vol. 139 pp. 2133-2140 DOI 10.1007/s00432-013-1539-5 (Year: 2013).*
Lombardi et al., "Adjuvant colon cancer chemotherapy: where we are and where we'll go" Cacner Treatment Reviews vol. 3653 pp. S34-S41 (Year: 2010).*
Guerini et al., "Mebendazole as a Candidate for Drug Repurposing in Oncology: An Extensive Review of Current Literature" Cancers (2019) 11, 1284; doi:10.3390/cancers11091284 (Year: 2019).*
International Search Report and Written Opinion for PCT/US2019/017291, dated Jun. 6, 2019. 9 pages.
Extended European Search Report for PCT/US2019/017291, dated Oct. 8, 2021. 8 pages.
A Phase I Study of Mebendazole for the Treatment of Pediatric Gliomas. https://ClinicalTrials.gov/show/NCT01837862. 16 pages.
Bai et al., Antiparasitic mebendazole shows survival benefit in 2 preclinical models of glioblastoma multiforme. Neuro Oncol. Sep. 2011;13(9):974-82.
Bai et al., Brain Penetration and Efficacy of Different Mebendazole Polymorphs in a Mouse Brain Tumor Model. Clin Cancer Res. Aug. 1, 2015;21(15):3462-3470.
Bai et al., Effective treatment of diverse medulloblastoma models with mebendazole and its impact on tumor angiogenesis. Neuro Oncol. Apr. 2015;17(4):545-54.

(Continued)

*Primary Examiner* — Eric Olson
(74) *Attorney, Agent, or Firm* — Casimir Jones, S.C.; Jeffrey W. Childers

(57) ABSTRACT

Prodrugs of mebendazole and methods for their use in treating a disease, disorder, or disorder, including cancer, are disclosed.

19 Claims, 6 Drawing Sheets

(56) References Cited

OTHER PUBLICATIONS

Beaumont et al., Design of ester prodrugs to enhance oral absorption of poorly permeable compounds: challenges to the discovery scientist. Curr Drug Metab. Dec. 2003;4(6):461-85.
Berge et al., Pharmaceutical salts. J Pharm Sci. Jan. 1977;66(1):1-19.
Brits et al., Characterization of polymorph transformations that decrease the stability of tablets containing the WHO essential drug mebendazole. J Pharm Sci. Mar. 2010;99(3):1138-51.
Carlert et al., In vivo dog intestinal precipitation of mebendazole: a basic BCS class II drug. Mol Pharm. Oct. 1, 2012;9(10):2903-11.
Chanteux et al., Accumulation and oriented transport of ampicillin in Caco-2 cells from its pivaloyloxymethylester prodrug, pivampicillin. Antimicrob Agents Chemother. Apr. 2005;49(4):1279-88.
Charoenlarp et al., Efficacy of single-dose mebendazole, polymorphic forms A and C, in the treatment of hookworm and Trichuris infections. Southeast Asian J Trop Med Public Health. Dec. 1993;24(4):712-6. Abstract. 1 page.
Chassaing et al., Highly water-soluble prodrugs of anthelmintic benzimidazole carbamates: synthesis, pharmacodynamics, and pharmacokinetics. J Med Chem. Mar. 13, 2008;51(5):1111-4.
Chiba et al., Improvement of dissolution and bioavailability for mebendazole, an agent for human echinococcosis, by preparing solid dispersion with polyethylene glycol. Chem Pharm Bull (Tokyo). Aug. 1991;39(8):2158-60.
Dando et al., Adefovir dipivoxil: a review of its use in chronic hepatitis B. Drugs. 2003;63(20):2215-34.
Daniel-Mwuambete et al., Effect of two formulations of benzimidazole carbamates on the viability of cysts of Echinococcus granulosus in vivo. Parasite. Dec. 2003;10(4):371-3.
Dawson et al., The pharmacokinetics and bioavailability of mebendazole in man: a pilot study using [3H]-mebendazole. Br J Clin Pharmacol 1982, 14, 453-5.
Dawson et al., 4-Amino-3-(3'-methoxycarbonyl-2'-thioureido)benzophenone, a prodrug of mebendazole. Eur J Drug Metab Pharmacokinet 1983, 8, 329-34.
Dawson et al., The effect of dose form on the bioavailability of mebendazole in man. Br J Clin Pharmacol. Jan. 1985;19(1):87-90.
Dawson et al., The pharmacokinetics and bioavailability of a tracer dose of [3H]-mebendazole in man. Br J Clin Pharmacol 1985, 19, 79-86.
Dayan. Albendazole, mebendazole and praziquantel. Review of non-clinical toxicity and pharmacokinetics. Acta Trop. May 2003;86(2-3):141-59.
De Paula et al., Mebendazole mesylate monohydrate: a new route to improve the solubility of mebendazole polymorphs. J Pharm Sci. Oct. 2013;102(10):3528-38.
De Witt et al., Repurposing Mebendazole as a Replacement for Vincristine for the Treatment of Brain Tumors. Mol Med. Apr. 2017;23:50-56.
Degoey, et al., Water-soluble prodrugs of the human immunodeficiency virus protease inhibitors lopinavir and ritonavir. J Med Chem. May 14, 2009;52(9):2964-70.
Doudican et al., Mebendazole induces apoptosis via Bcl-2 inactivation in chemoresistant melanoma cells. Mol Cancer Res. Aug. 2008;6(8):1308-15.
Fan et al., Design, synthesis and biological evaluation of brain-specific glucosyl thiamine disulfide prodrugs of naproxen. Eur J Med Chem. Sep. 2011;46(9):3651-61.
Flores-Ramos et al., A highly water soluble benzimidazole derivative useful for the treatment of fasciolosis. Bioorg Med Chem Lett. Dec. 15, 2014;24(24):5814-5817.
Greene, P.G.M. Wuts, Protective Groups in Organic Synthesis, 3rd ed. John Wiley & Sons. 1999. TOC only. 3 pages.
Honorato et al., Polymorphism evaluation in generic tablets containing mebendazole by dissolution tests. J Braz Chem Soc 2012, 23, 220-227.
Kearney et al., Tenofovir disoproxil fumarate: clinical pharmacology and pharmacokinetics. Clin Pharmacokinet. 2004;43(9):595-612.
Klepser et al., Clinical pharmacokinetics of newer cephalosporins. Clin Pharmacokinet. May 1995;28(5):361-84.
Larsen et al., Repurposing the antihelmintic mebendazole as a hedgehog inhibitor. Mol Cancer Ther. Jan. 2015;14(1):3-13.
Liu et al., An alternative mebendazole formulation for cystic echinococcosis: the treatment efficacy, pharmacokinetics and safety in mice. Parasit Vectors. Dec. 10, 2014;7:589.
Liu et al., Enhanced bioavailability and cysticidal effect of three mebendazole-oil preparations in mice infected with secondary cysts of Echinococcus granulosus. Parasitol Res. Sep. 2012;111(3):1205-11.
Majer et al., Discovery of Orally Available Prodrugs of the Glutamate Carboxypeptidase II (GCPII) Inhibitor 2-Phosphonomethylpentanedioic Acid (2-PMPA). J Med Chem. Mar. 24, 2016;59(6):2810-9.
Martarelli et al., Mebendazole inhibits growth of human adrenocortical carcinoma cell lines implanted in nude mice. Cancer Chemother Pharmacol. Apr. 2008;61(5):809-17.
Martins et al., Intermolecular contacts influencing the conformational and geometric features of the pharmaceutically preferred mebendazole polymorph C. J Pharm Sci. Jul. 2009;98(7):2336-44.
Mebendazole in Newly Diagnosed High-Grade Glioma Patients Receiving Temozolomide. 7 pages. https://ClinicalTrials.gov/show/NCT01729260.
Mukhopadhyay et al., Mebendazole elicits a potent antitumor effect on human cancer cell lines both in vitro and in vivo. Clin Cancer Res. Sep. 2002;8(9):2963-9.
Nielsen et al., N-alkoxycarbonyl prodrugs of mebendazole with increased water solubility. Int J Pharm 1994, 102, 231-9.
Nielsen. Improved peroral bioavailability of mebendazole in rabbits by administraion of various N-alkoxycarbonyl derivatives of mebendazole. International Journal of Pharmaceutics, 104, 1994, pp. 175-179.
Nygren et al., Repositioning of the anthelmintic drug mebendazole for the treatment for colon cancer. J Cancer Res Clin Oncol. Dec. 2013;139(12):2133-40.
Pantziarka et al., Repurposing Drugs in Oncology (ReDO)-mebendazole as an anti-cancer agent. Ecancermedicalscience. Jul. 10, 2014;8:443. 16 pages.
Phase I Study of Mebendazole Therapy for Recurrent/Progressive Pediatric Brain Tumors. 9 pages. https://ClinicalTrials.gov/show/NCT02644291.
Pinto et al., The anthelmintic drug mebendazole inhibits growth, migration and invasion in gastric cancer cell model. Toxicol In Vitro. Dec. 2015;29(8):2038-44.
Rodriguez-Caabeiro et al., Experimental chemotherapy and toxicity in mice of three mebendazole polymorphic forms. Chemotherapy. 1987;33(4):266-71.
Sasaki et al., The anthelmintic drug mebendazole induces mitotic arrest and apoptosis by depolymerizing tubulin in non-small cell lung cancer cells. Mol Cancer Ther. Nov. 2002;1(13):1201-9.
Study of the safety, tolerability and efficacy of metabolic combination treatments on cancer (METRICS). 2021. NCT02201381. 7 pages.
Swanepoel et al., Quality evaluation of generic drugs by dissolution test: changing the USP dissolution medium to distinguish between active and non-active mebendazole polymorphs. Eur J Pharm Biopharm. May 2003;55(3):345-9.
Ueda et al., Phosphonooxymethyl prodrugs of the broad spectrum antifungal azole, ravuconazole: synthesis and biological properties. Bioorg Med Chem Lett. Nov. 3, 2003;13(21):3669-72.
Zhou et al., Development of a high throughput equilibrium solubility assay using miniaturized shake-flask method in early drug discovery. J Pharm Sci. Nov. 2007;96(11):3052-71.
Zimmermann et al., N-Substituted Prodrugs of Mebendazole Provide Improved Aqueous Solubility and Oral Bioavailability in Mice and Dogs. J Med Chem. May 10, 2018;61(9):3918-3929.

* cited by examiner

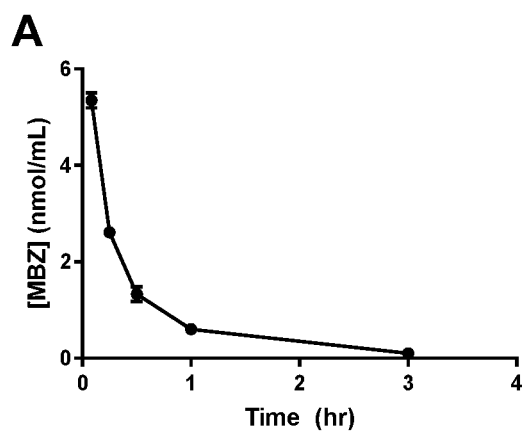
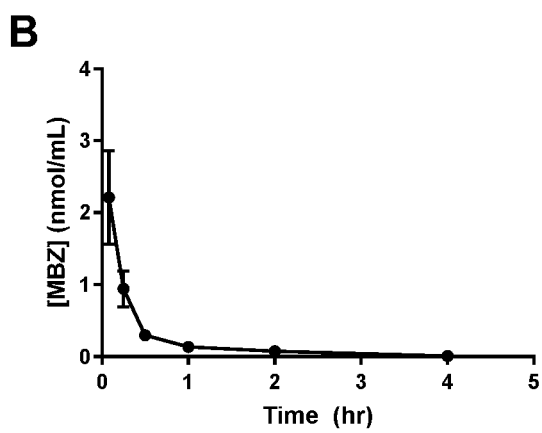
*Fig. 3A*  *Fig. 3B*

A. Plasma
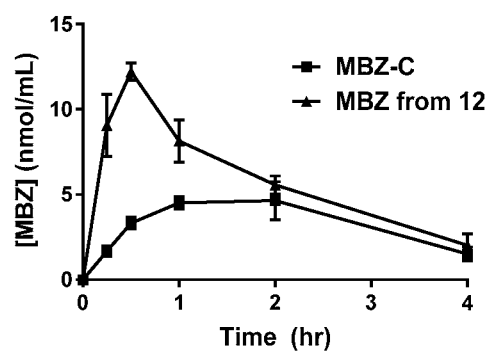
B. Brain
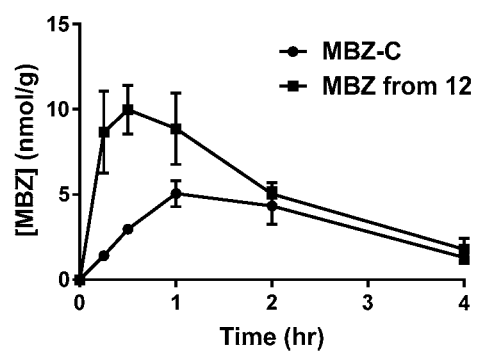
*Fig. 4A*
*Fig. 4B*

MEBENDAZOLE PRODRUGS WITH ENHANCED SOLUBILITY AND ORAL BIOAVAILABILITY

BACKGROUND

Mebendazole (MBZ) is a benzimidazole analog that was originally developed as a broad-spectrum anthelmintic. MBZ also has been shown to have anti-cancer properties in a broad range of pre-clinical studies across various cancer types (Martarelli, et al., 2008; Bai, et al., 2015; Nygren, et al., 2013; Bai, et al., 2011; Bai, et al., Neuro-Oncology, 2015) and more recently in exploratory clinical studies where promising effects were observed (NCT01729260; NCT01837862; NCT02644291; NCT02201381).

Despite these encouraging results, the development of MBZ for indications requiring systemic availability remains challenging. This challenge, in part, is due to its poor physicochemical properties, specifically low aqueous solubility, which leads to poor oral bioavailability. Formulation strategies to improve the oral bioavailability remain actively researched (Liu, et al., 2014; Liu, et al., 2012; Daniel-Mwuambete, et al., 2003; Dawson, et al., 1985; Chiba, et al., 1991).

Prodrug approaches to improve the water solubility of MBZ also have been investigated, focusing on 4-amino-3-(3'-methoxycarbonyl-2'-thioureido) benzophonone (Dawson, et al., 1983) or N-alkoxycarbonyl derivatives of MBZ (Nielsen, et al., 1994). These studies, however, were limited to chemistry focusing on simple acylations of the benzimidazole nitrogens and a single 4-amino-3-(3'-methoxycarbonyl-2'-thioureido)benzophonone analog. Moreover, the prodrugs were not systematically evaluated to demonstrate significant improvements over MBZ.

SUMMARY

The presently disclosed subject matter provides prodrugs of mebendazole and their use for treating a disease, disorder, or condition, including cancer.

In some aspects, the presently disclosed subject matter provides a compound having the structure of formula (I):

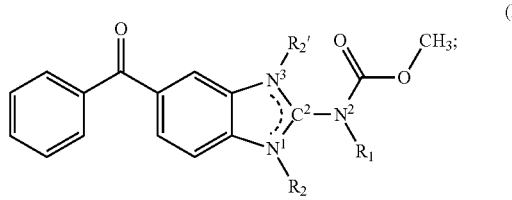

wherein:

$R_2$ or $R_2'$ can be absent or present, provided that at least one of $R_2$ and $R_2'$ is present;

the dashed line indicates a double bond between $N^1$ and $C^2$, in which $R_2'$ is present and $R_2$ is absent, or a double bond between $N^3$ and $C^2$, in which $R_2$ is present and $R_2'$ is absent;

$R_1$ is selected from the group consisting of H and

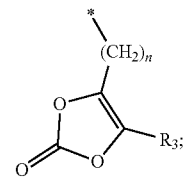

wherein: n is an integer selected from 1, 2, 3, 4, 5, 6, 7, and 8; and $R_3$ is straight-chain alkyl or branched alkyl, each of which can be substituted;

$R_2$ or $R_2'$ when present are each independently H or —$(CR_4R_5)_m$—$R_y$, wherein m is an integer selected from 1, 2, 3, 4, 5, 6, 7, and 8; each $R_4$ and $R_5$ is independently H or straight-chain alkyl or branched alkyl, each of which can be substituted; and $R_y$ is selected from the group consisting of: —O—(C=O)—$R_z$, wherein $R_z$ is selected from the group consisting of —$R_6$, —O—$R_6$, —$(CR_7R_8)_p$—C(=O)—$OR_9$, —O—$(CR_7R_8)_p$—$R_{10}$, —O—$R_{10}$, —$R_{10}$, —$(CR_7R_8)_p$—$CR_{11}R_{12}$—C(=O)—$OR_9$, and —$(CR_7R_8)_p$—$NR_{15}$—(C=O)—$CR_{16}R_{17}(NR_{18}$—C(=O)—$R_{19})$, wherein p is an integer selected from 1, 2, 3, 4, 5, 6, 7, and 8; each $R_6$ is independently straight-chain or branched alkyl, each of which can be substituted; each $R_7$, $R_8$, $R_9$, $R_{11}$, $R_{15}$, $R_{16}$, $R_{17}$, $R_{18}$, and $R_{19}$ is independently selected from the group consisting of H, or straight-chain alkyl or branched alkyl, each of which can be substituted; $R_{10}$ is selected from the group consisting of straight-chain alkyl or branched alkyl, each of which can be substituted or unsubstituted, substituted cycloalkyl, heterocycloalkyl, substituted heterocycloalkyl, and a monosaccharide; and $R_{12}$ is —$NR_{13}R_{14}$, wherein $R_{13}$ and $R_{14}$ are each H, or straight-chain alkyl or branched alkyl, each of which can be substituted;

—O—P(=O)(O⁻)—O—$(CR_7R_8)_p$—O—(C=O)—O—$R_6$ or —O—P(=O)(OH)—O—$(CR_7R_8)_p$—O—(C=O)—O—$R_6$, wherein p, $R_6$, $R_7$, and $R_8$ are as defined hereinabove; and —$R_{20}$, wherein $R_{20}$ is an amino acid or a substituted amino acid, wherein the amino acid or substituted amino acid is attached to the carbon atom of the —$CR_4R_5$— group through a terminal carboxyl moiety of the amino acid or substituted amino acid;

provided that both $R_1$ and $R_2$ are not H at the same time; or a pharmaceutically acceptable salt thereof.

In particular aspects, the presently disclosed prodrugs were obtained as a mixture of their $N^1$ and $N^3$ positional isomers resulting from the undifferentiated substitution of both benzimidazole nitrogen atoms. For simplicity, however, representative structures are shown with promoeities on the $N^1$ position.

In other aspects, the presently disclosed subject matter provides a pharmaceutical composition comprising the compound of formula (I) and a pharmaceutically acceptable carrier, diluent or excipient. In particular aspects, the pharmaceutical composition further comprises one or more therapeutic agents selected from the group consisting of a chemotherapeutic agent, a radiotherapeutic agent, an immunotherapeutic agent, and combinations thereof.

In yet other aspects, the presently disclosed subject matter provides a method for treating a disease, disorder, or condition, the method comprising administering to a subject in need of treatment thereof a therapeutically effective amount of a compound of formula (I) of a pharmaceutical formulation thereof. In particular aspects, the disease, disorder, or condition is cancer. In yet more particular aspects, the method comprises administering to the subject a pharmaceutical composition comprising one or more therapeutic agents selected from the group consisting of a chemotherapeutic agent, a radiotherapeutic agent, an immunotherapeutic agent, and combinations thereof.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
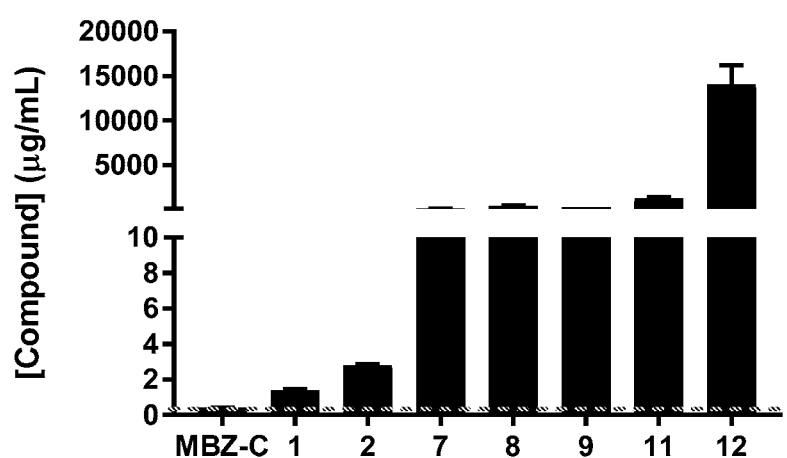
Figure 2:
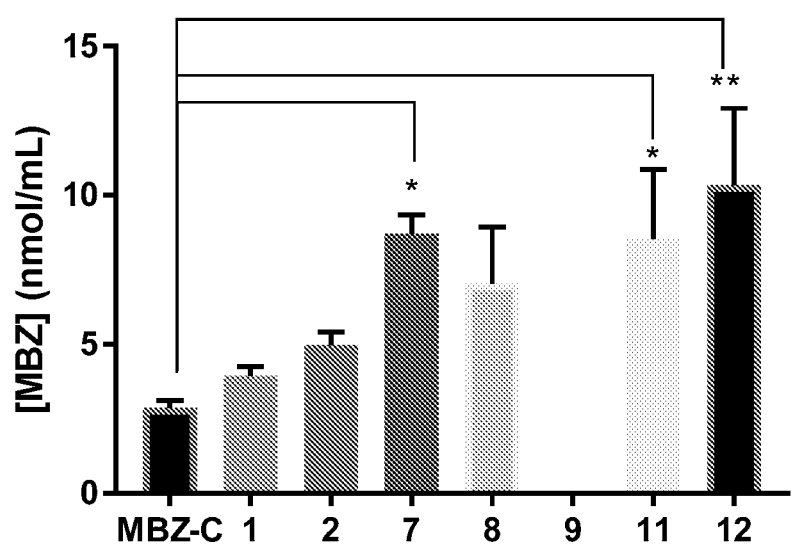
Figure 5:
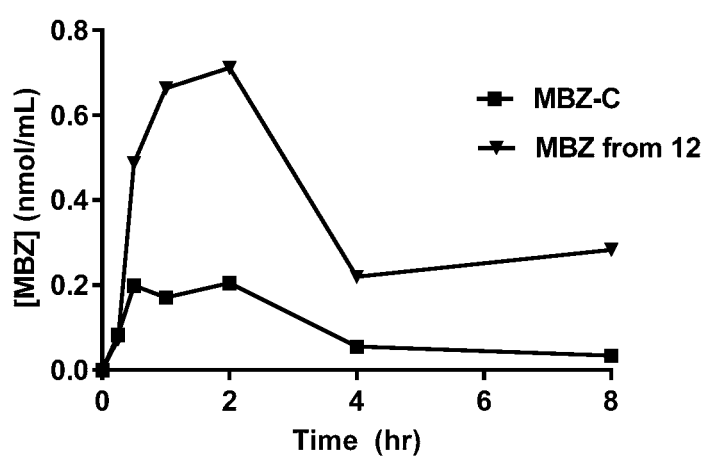
Figure 6:
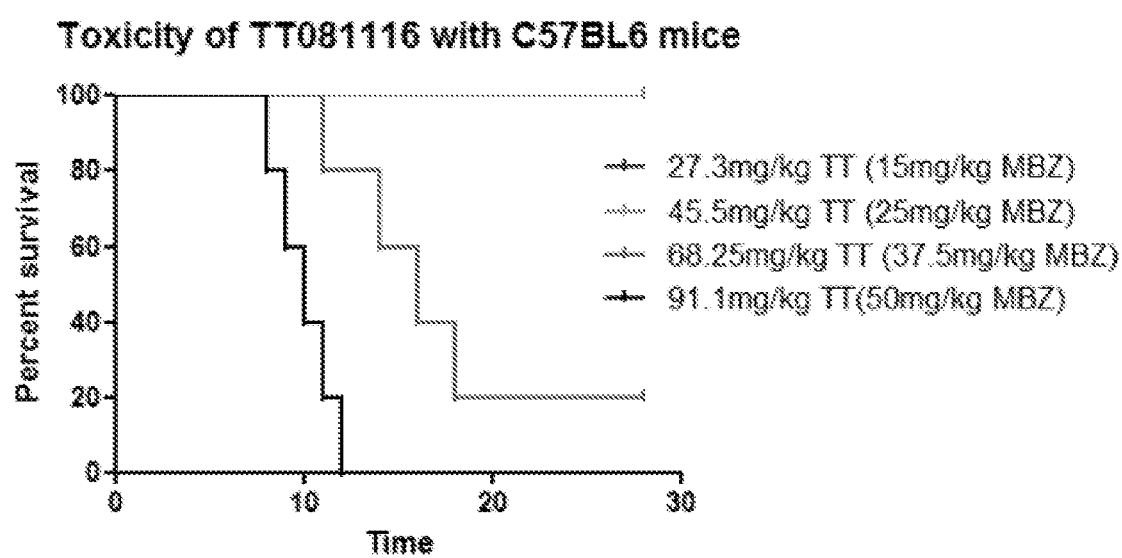

Having thus described the presently disclosed subject matter in general terms, reference will now be made to the accompanying Figures, which are not necessarily drawn to scale, and wherein:

FIG. 1 shows the aqueous solubility of MBZ and MBZ prodrugs 1, 2, 7-9, 11 and 12 in 0.01M PBS determined using equilibrium solubility methods. Data expressed as mean±SEM (n=3). The dotted line represents the solubility of MBZ-C;

FIG. 2 shows MBZ plasma concentration at 1 h post oral administration of MBZ-C or prodrug administration. MBZ-C or 1, 2, 7, 8, 9, 11, 12 were administered to male CD-1 mice as a single dose by oral gavage at 30 mg/kg MBZ equivalent dose. Data expressed as a mean±SEM (n=3), with statistics quantified using one-way ANOVA with Dunnett's multiple comparison test $*p<0.05$, $**p<0.01$;

FIG. 3A and FIG. 3B show the MBZ pharmacokinetics in mice and dogs following intravenous (IV) administration. (FIG. 3A) MBZ-C was administered to male CD-1 mice as a single IV dose at 1.5 mg/kg and plasma concentrations were determined over time. (FIG. 3B) MBZ-C was administered to male beagle dogs as a single IV dose of 0.3 mg/kg and plasma concentrations were determined over time. Pharmacokinetic parameters were calculated using non-compartmental analysis in WinNonlin; data expressed as mean±SEM for mouse (n=3) and as mean for dog (n=2) (Table 4);

FIG. 4A and FIG. 4B show (FIG. 4A) MBZ plasma and (FIG. 4B) brain pharmacokinetics in mice after oral administration of MBZ-C or 12. MBZ-C and 12 was administered to mice as a single PO dose of 30 mg/kg equivalent for 12. Pharmacokinetic parameters were calculated using non-compartmental analysis in WinNonlin, with data expressed as mean±SEM, (n=3 mice/timepoint) (Table 5 and Table 6);

FIG. 5 shows MBZ plasma exposure in male beagle dogs after oral administration of MBZ-C or 12. MBZ-C and prodrug 12 was administered to male beagle dogs (n=2 per group) as a single PO dose of 2.5 mg/kg or equivalent for 12. Pharmacokinetic parameters were calculated using non-compartmental analysis in WinNonlin, with data expressed as a mean (Table 7); and FIG. 6 shows the toxicity of TT081116 (prodrug 12) with C57BL6 mice.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures.

I. Mebendazole Prodrugs with Enhanced Solubility and Oral Bioavailability

The chemical structure of mebendazole (MBZ) is provided immediately herein below:

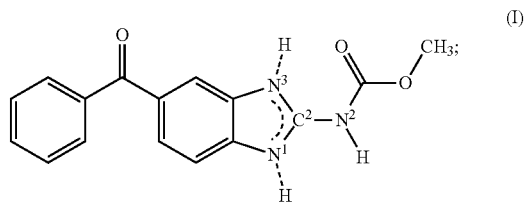

(I)

The presently disclosed subject matter provides, in part, a prodrug approach for MBZ with various promoieties substituted at the —NH— position, i.e., either $N^1$ or $N^3$ of the imidazole moiety of MBZ including, but not limited to, acyloxy methyl, animoacyloxy methyl, and substituted phosphonooxy methyl moieties, to improve the aqueous solubility and bioavailability of MBZ.

Representative prodrugs of MBZ are provided in Table 1, immediately herein below.

TABLE 1

Representative Prodrugs of MBZ.

| Compound No. | Structure | MW (g/mol) |
|---|---|---|
| 1 (TT-040416) | 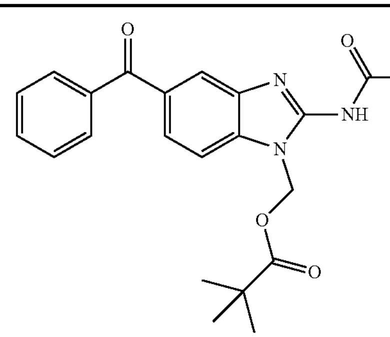 | 409.44 |

TABLE 1-continued
Representative Prodrugs of MBZ.
| Compound No. | Structure | MW (g/mol) |
|---|---|---|
| 2 (TT-110416B) | 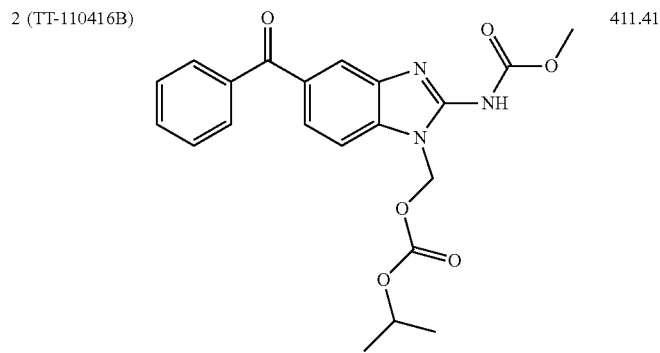 | 411.41 |
| 18 (TT-130416A) | 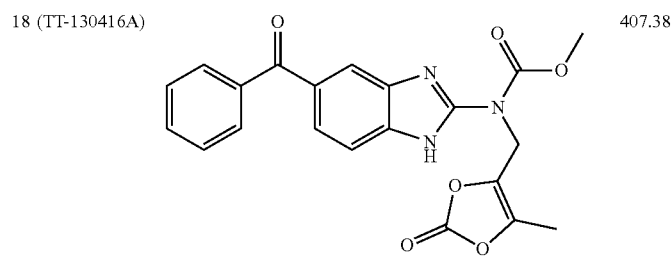 | 407.38 |
| 12 (TT-081116) | 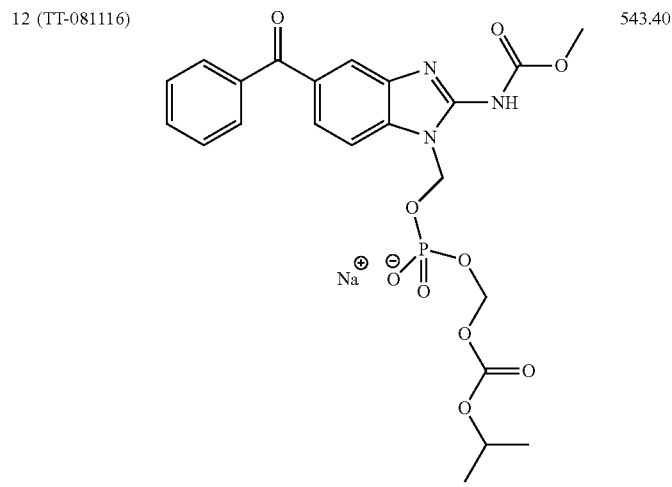 | 543.40 |

TABLE 1-continued

Representative Prodrugs of MBZ.

| Compound No. | Structure | MW (g/mol) |
|---|---|---|
| — | 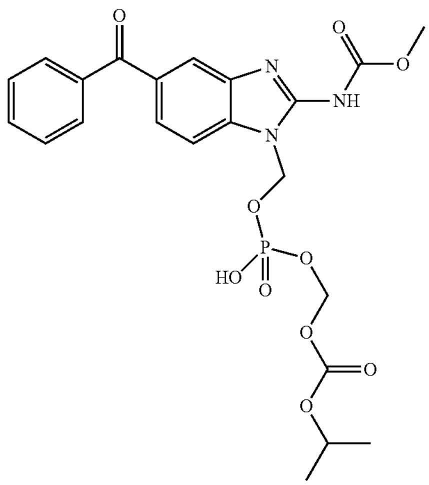 [SMILES: COC(=O)Nc1nc2cc(C(=O)c3ccccc3)ccc2n1COP(=O)(O)OCOC(=O)OC(C)C] | 521.42 |
| 7 (TT-010117) | 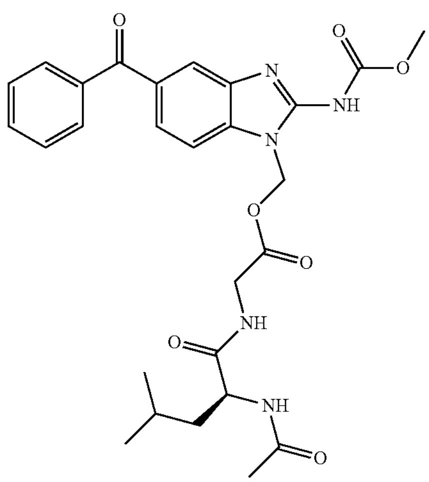 [SMILES: COC(=O)Nc1nc2cc(C(=O)c3ccccc3)ccc2n1COC(=O)CNC(=O)[C@H](CC(C)C)NC(C)=O] | 537.57 |
| 8 (TT-130217) | 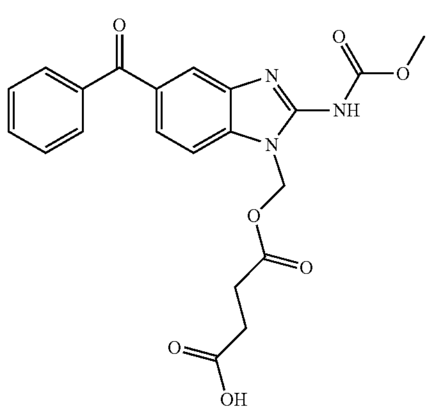 [SMILES: COC(=O)Nc1nc2cc(C(=O)c3ccccc3)ccc2n1COC(=O)CCC(=O)O] | 425.40 |

TABLE 1-continued

Representative Prodrugs of MBZ.

| Compound No. | Structure | MW (g/mol) |
|---|---|---|
| 9 (TT-040317) | 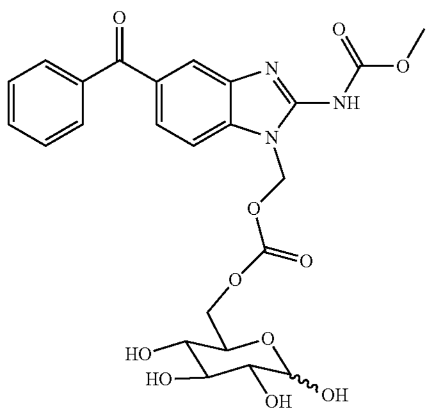 [SMILES: COC(=O)Nc1nc2cc(C(=O)c3ccccc3)ccc2n1COC(=O)OCC1OC(O)C(O)C(O)C1O] | 531.47 |
| 14 (JV-3229) | 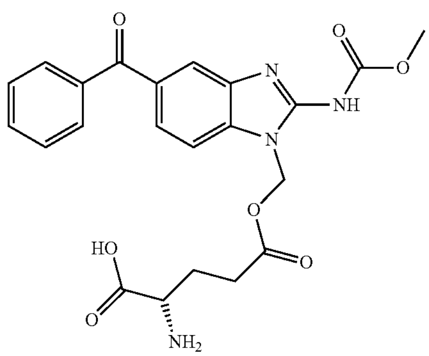 | 454.15 |
| 15 (TTM-001) | 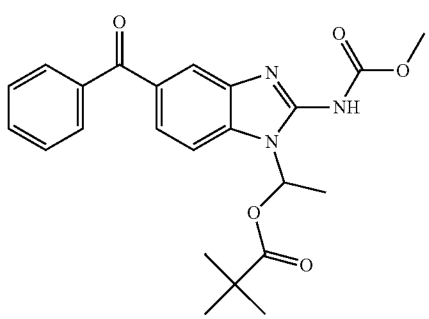 [SMILES: COC(=O)Nc1nc2cc(C(=O)c3ccccc3)ccc2n1C(C)OC(=O)C(C)(C)C] | 423.46 |
| 16 (TTM-002) | 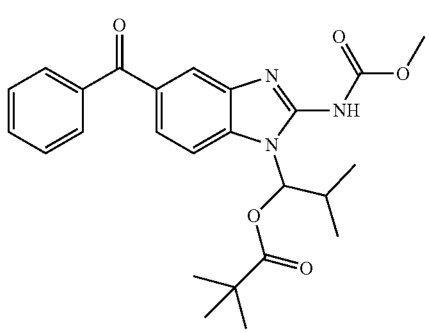 [SMILES: COC(=O)Nc1nc2cc(C(=O)c3ccccc3)ccc2n1C(OC(=O)C(C)(C)C)C(C)C] | 451.51 |

TABLE 1-continued

Representative Prodrugs of MBZ.

| Compound No. | Structure | MW (g/mol) |
|---|---|---|
| 17 (TTM-003) | 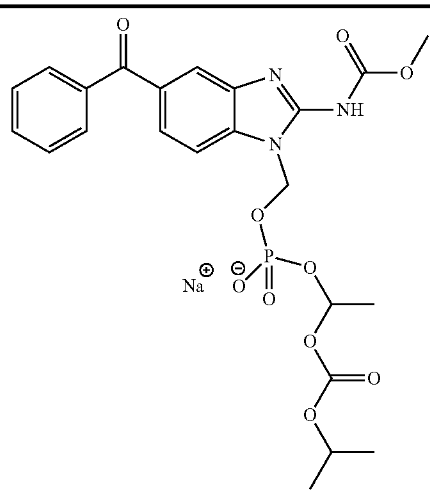 | 557.42 |
| — | 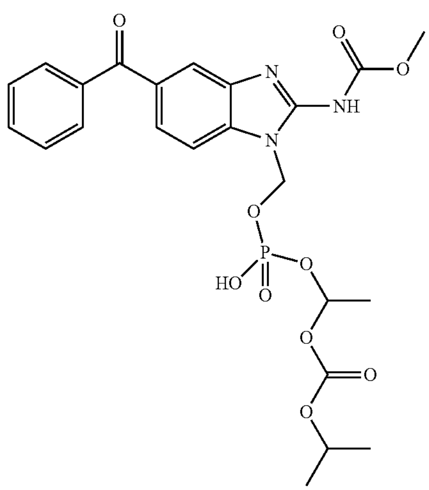 [SMILES: COC(=O)Nc1nc2cc(C(=O)c3ccccc3)ccc2n1COP(=O)(O)OC(C)OC(=O)OC(C)C] | 535.45 |

Accordingly, in some embodiments, the presently disclosed subject matter provides a compound having the structure of formula (I):

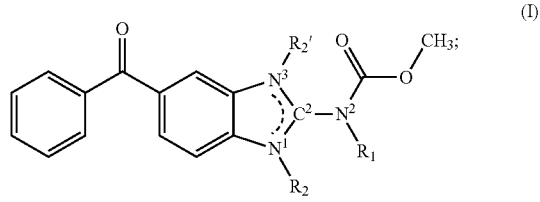

wherein:

R$_2$ or R$_2$' can be absent or present, provided that at least one of R$_2$ and R$_2$' is present;

the dashed line indicates a double bond between N$^1$ and C$^2$, in which R$_2$' is present and R$_2$ is absent, or a double bond between N$^3$ and C$^2$, in which R$_2$ is present and R$_2$' is absent;

R$_1$ is selected from the group consisting of H and

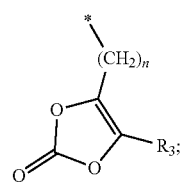

wherein: n is an integer selected from 1, 2, 3, 4, 5, 6, 7, and 8; and R$_3$ is straight-chain alkyl or branched alkyl, each of which can be substituted;

R$_2$ or R$_2$' when present are each independently H or —(CR$_4$R$_5$)$_m$—R$_y$, wherein m is an integer selected from 1, 2, 3, 4, 5, 6, 7, and 8; each R$_4$ and R$_5$ is independently H or straight-chain alkyl or branched alkyl, each of which can be substituted; and R$_y$ is selected from the group consisting of:
—O—(C=O)—R$_z$, wherein R$_z$ is selected from the group consisting of —R$_6$, —O—R$_6$, —(CR$_7$R$_8$)$_p$—C(=O)—OR$_9$, —O—(CR$_7$R$_8$)$_p$—R$_{10}$, —O—R$_{10}$, —R$_{10}$, —(CR$_7$R$_8$)$_p$—

$CR_{11}R_{12}$—C(=O)—$OR_9$, and —$(CR_7R_8)_p$—$NR_{15}$—(C=O)—$CR_{16}R_{17}(NR_{18}$—C(=O)—$R_{19})$, wherein p is an integer selected from 1, 2, 3, 4, 5, 6, 7, and 8; each $R_6$ is independently straight-chain or branched alkyl, each of which can be substituted; each $R_7$, $R_8$, $R_9$, $R_{11}$, $R_{15}$, $R_{16}$, $R_{17}$, $R_{18}$, and $R_{19}$ is independently selected from the group consisting of H, or straight-chain alkyl or branched alkyl, each of which can be substituted; $R_{10}$ is selected from the group consisting of straight-chain alkyl or branched alkyl, each of which can be substituted or unsubstituted, substituted cycloalkyl, heterocycloalkyl, substituted heterocycloalkyl, and a monosaccharide; and $R_{12}$ is —$NR_{13}R_{14}$, wherein $R_{13}$ and $R_{14}$ are each H, or straight-chain alkyl or branched alkyl, each of which can be substituted;

—O—P(=O)(O)—O—$(CR_7R_8)_p$—O—(C=O)—O—$R_6$ or —O—P(=O)(OH)—O—$(CR_7R_8)_p$—O—(C=O)—O—$R_6$, wherein p, $R_6$, $R_7$, and $R_8$ are as defined hereinabove; and —$R_{20}$, wherein $R_{20}$ is an amino acid or a substituted amino acid, wherein the amino acid or substituted amino acid is attached to the carbon atom of the —$CR_4R_5$— group through a terminal carboxyl moiety of the amino acid or substituted amino acid;

provided that both $R_1$ and $R_2$ are not H at the same time; or a pharmaceutically acceptable salt thereof.

In particular aspects, the presently disclosed prodrugs were obtained as a mixture of their $N^1$ and $N^3$ positional isomers resulting from the undifferentiated substitution of both benzimidazole nitrogen atoms. For simplicity, however, representative structures are shown with promoieties on the $N^1$-position.

As provided herein below, in some embodiments, alkyl can be $C_1$-$C_{12}$ straight-chain alkyl ($C_1$, $C_2$, $C_3$, $C_4$, $C_5$, $C_6$, $C_7$, $C_8$, $C_9$, $C_{10}$, $C_{11}$, or $C_{12}$ straight-chain alkyl), including $C_1$-$C_6$ straight-chain alkyl ($C_1$, $C_2$, $C_3$, $C_4$, $C_5$, or $C_6$ straight-chain alkyl), or, in other embodiments, can be $C_3$-$C_{12}$ branched alkyl ($C_3$, $C_4$, $C_5$, $C_6$, $C_7$, $C_8$, $C_9$, $C_{10}$, $C_{11}$, or $C_{12}$ branched alkyl), or $C_1$-$C_6$ branched alkyl ($C_1$, $C_2$, $C_3$, $C_4$, $C_5$, or $C_6$ branched alkyl). Accordingly, alkyl includes, but is not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, and dodecyl. In particular embodiments, straight-chain alkyl includes methyl, ethyl, n-propyl, n-butyl, n-pentyl, 1, n-hexyl, n-heptyl, n-octyl, n-decyl, n-undecyl, and dodecyl, which can optionally be substituted. In other embodiments, branched alkyl includes isopropyl, isobutyl, sec-butyl, tert-butyl, sec-pentyl, and isopentyl, which optionally can be substituted.

As also provided herein below, substituted alkyl can include $C_1$-$C_{12}$ straight-chain or $C_3$-$C_{12}$ branched alkyl, as defined hereinabove, substituted with one of more substituent groups. In some embodiments, the substituent group is selected from the group consisting of halogen, —OH, —SH, aryl, e.g., phenyl, $C_3$-$C_7$ cycloalkyl (including $C_3$, $C_4$, $C_5$, $C_6$, and $C_7$ cycloalkyl), —O—$C_1$-$C_4$ alkyl (including —O—$C_1$ alkyl, —O—$C_2$ alkyl, —O—$C_3$ alkyl, and —O—$C_4$ alkyl), —S—$C_1$-$C_4$ alkyl (including —S—$C_1$ alkyl, —S—$C_2$ alkyl, —S—$C_3$ alkyl, and —S—$C_4$ alkyl), and the like.

Further, one of ordinary skill in the art would appreciate upon reading the current disclosure that $R_2$ cannot be a N-alkoxycarbonyl substituent group disclosed in Nielsen et al., 1994, including —C(=O)—$CH_3$, —C(=O)—$CH_2CH_3$, or —C(=O)—$CH_2CH_2CH_3$.

In some embodiments, $R_2$ is H and $R_1$ is:

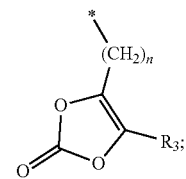

wherein $R_3$ is $C_1$-$C_6$ straight-chain or branched alkyl. In one embodiment, the compound of formula (I) has the following structure:

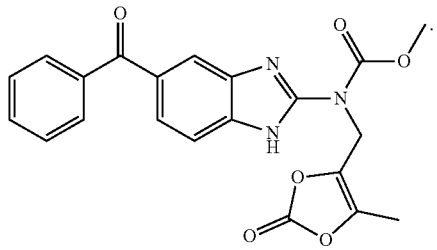 [SMILES: COC(=O)N(Cc1oc(=O)oc1C)c1nc2cc(C(=O)c3ccccc3)ccc2[nH]1]

In other embodiments, $R_1$ is H and —$(CR_4R_5)_m$—$R_y$ is —$(CR_4R_5)_m$—O—(C=O)—$R_6$, wherein $C_4$ and $C_5$ are each H or $C_1$-$C_6$ straight-chain or branched alkyl and $R_6$ is $C_1$-$C_6$ straight-chain or branched alkyl. In particular embodiments, the compound of formula (I) is selected from the group consisting of:

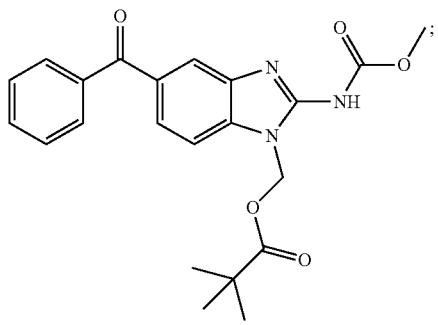

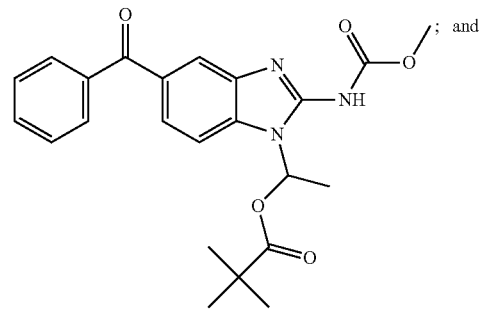

-continued

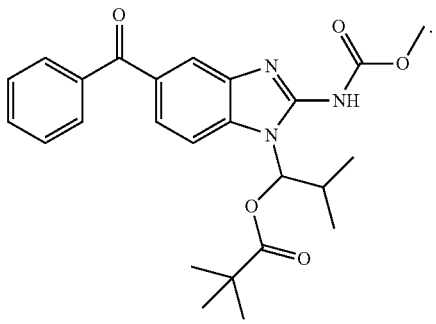

In some embodiments, $R_1$ is H and —$(CR_4R_5)_m$—$R_y$ is —$(CR_4R_5)_m$—O—(C=O)—O—$R_6$, wherein $C_4$ and $C_5$ are each H and $R_6$ is $C_1$-$C_6$ straight-chain or branched alkyl. In one embodiment, the compound of formula (I) has the following structure:

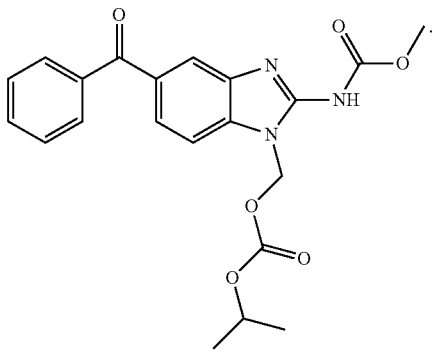 [SMILES: COC(=O)Nc1nc2cc(C(=O)c3ccccc3)ccc2n1COC(=O)OC(C)C]

In other embodiments, $R_1$ is H and —$(CR_4R_5)_m$—$R_y$ is —$(CR_4R_5)_m$—O—(C=O)—$(CR_7R_8)_p$—C(=O)—$OR_9$, wherein $R_4$, $R_5$, $R_7$, $R_8$, and $R_9$ are each H. In one embodiment, the compound of formula (I) has the following structure:

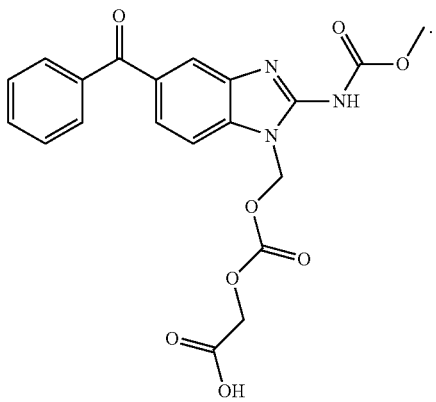 [SMILES: COC(=O)Nc1nc2cc(C(=O)c3ccccc3)ccc2n1COC(=O)OCC(=O)O]

In yet other embodiments, $R_1$ is H and —$(CR_4R_5)_m$—$R_y$ is —$(CR_4R_5)_m$—O—(C=O)—O—$(CR_7R_8)_p$—$R_{10}$ or —$(CR_4R_5)_m$—O—(C=O)—$R_{10}$ wherein $R_4$, $R_5$, $R_7$, $R_8$, and $R_9$ are each H, and $R_{10}$ is a monosaccharide. In one embodiment, the compound of formula (I) has the following structure:

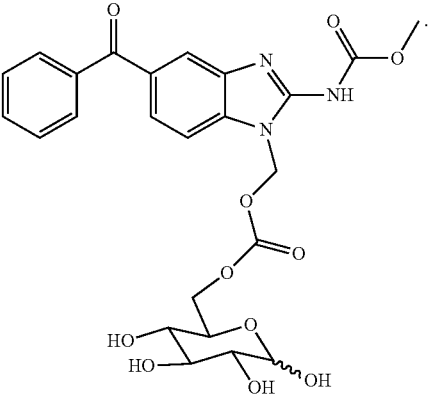 [SMILES: COC(=O)Nc1nc2cc(C(=O)c3ccccc3)ccc2n1COC(=O)OCC1OC(O)C(O)C(O)C1O]

One of ordinary skill in the art would appreciate that other monosaccharides, or derivatives thereof, are suitable for use with the presently disclosed subject matter. In some embodiments, the monosaccharide comprises an aldohexose, or a derivative thereof, including, but not limited to, D-glucose, L-glucose, D-allose, L-allose, D-altrose, L-altrose, D-mannose, L-mannose, D-gulose, L-gulose, D-idose, L-idose, D-galactose, L-galactose, D-talose, and L-talose. In other embodiments, the monosaccharide comprises a deoxyaldohexose, i.e., an aldohexose having one or more hydroxyl groups replaced by a hydrogen, including, but not limited to, D-fucose, L-fucose, D-rhamnose, L-rhamnose, D-quinovose, L-quinovose, D-pneumose, and L-pneumose. Other monosaccharides suitable for use with the presently disclosed subject matter include, but are not limited to, D-xylose, L-xylose, D-ribose, L-ribose, D-arabinose, L-arabinose, D-lyxose, and L-lyxose.

One of ordinary skill in the art upon review of the presently disclosed subject matter, in particular, Example 1 provided herein below, which discloses the synthesis of representative compound 9, that the monosaccharide can include the —O—$(CR_7R_8)_p$— group. In other words, the —O—$(CR_7R_8)_p$— group forms a part of the monosaccharide as defined by $R_{10}$. In such embodiments, —$(CR_4R_5)_m$—$R_y$ can be defined as —$(CR_4R_5)_m$—O—(C=O)—$R_{10}$. For example, if $R_{10}$ is D-glucose, then the monosaccharide includes the —O—$(CR_7R_8)_p$— group:

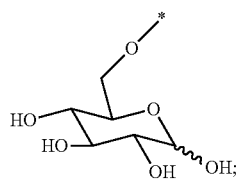 [SMILES: *OCC1OC(O)C(O)C(O)C1O]

wherein the * indicates the point of attachment to the carbonyl group of $R_y$. In other embodiments, for example, if $R_{10}$ is D-xylose, then the monosaccharide does not include the —O—$(CR_7R_8)_p$— group, and the —O—$(CR_7R_8)_p$— group is required to be a part of the definition of $R_y$:

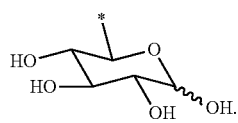

In other embodiments, $R_1$ is H and —$(CR_4R_5)_m$—$R_y$ is —$(CR_4R_5)_m$—P(=O)(O⁻)—O—$(CR_7R_8)_p$—O—(C=O)—O—$R_6$, wherein $R_4$ and $R_5$ are each H; $R_7$ and $R_8$ are each H or $C_1$-$C_6$ substituted or unsubstituted alkyl; and $R_6$ is $C_1$-$C_6$ straight-chain or branched alkyl. In particular embodiments, the compound of formula (I) has a structure selected from the group consisting of:

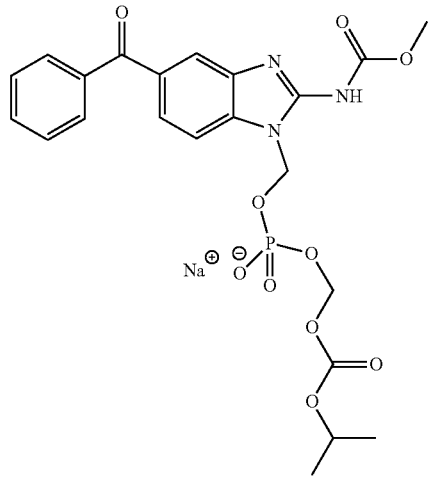

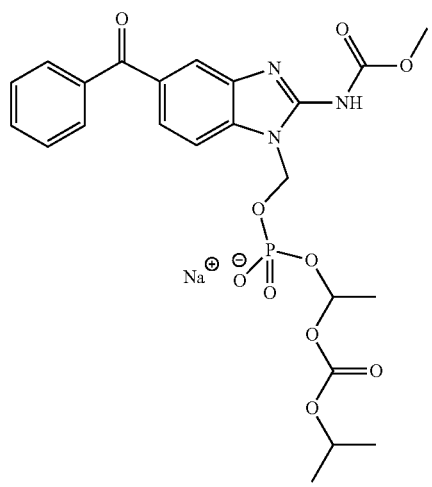

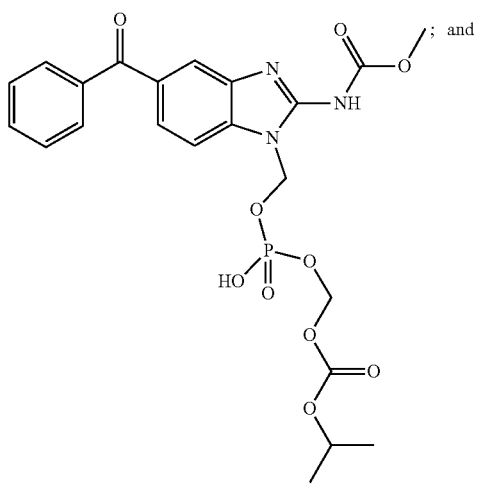

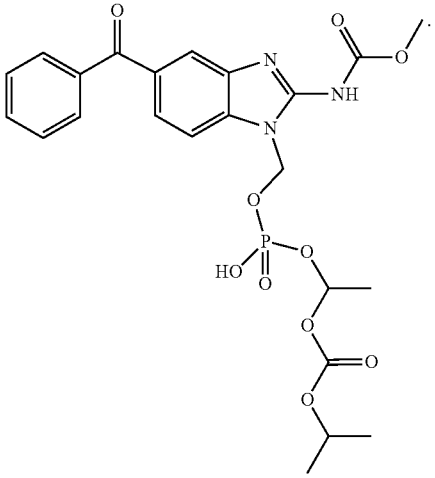 [SMILES: COC(=O)Nc1nc2cc(C(=O)c3ccccc3)ccc2n1COP(=O)(O)OC(C)OC(=O)OC(C)C]

In one embodiment, the compound of formula (I) is:

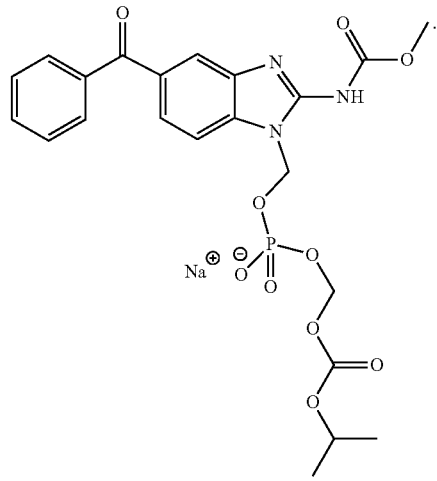 [SMILES: COC(=O)Nc1nc2cc(C(=O)c3ccccc3)ccc2n1COP(=O)([O-])OCOC(=O)OC(C)C ; [Na+]]

In yet other embodiments, $R_1$ is H and —$(CR_4R_5)_m$—$R_y$ is selected from the group consisting of: —$(CR_4R_5)_m$—O—(C=O)—$(CR_7R_8)_p$—$CR_{11}R_{12}$—C(=O)—$OR_9$; —$(CR_4R_5)_m$—O—(C=O)—$(CR_7R_8)_p$—$NR_{15}$—(C=O)—$CR_{16}R_{17}(NR_{15}$—C(=O)—$R_{19})$; and —$(CR_4R_5)_m$—$R_{20}$, wherein each $R_4$, $R_5$, $R_7$, and $R_8$ is H; $R_9$, $R_{11}$, $R_{15}$, $R_{16}$, and $R_{18}$ are each H; $R_{12}$ is —$NR_{13}R_{14}$, wherein $R_{13}$ and $R_{14}$ are each H; and $R_{17}$ and $R_{19}$ are each $C_1$-$C_6$ straight-chain or branched alkyl; and $R_{20}$ is an amino acid or a substituted amino acid.

In particular embodiments, the compound of formula (I) is selected from the group consisting of:

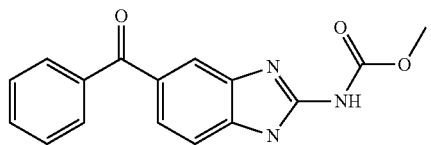

and

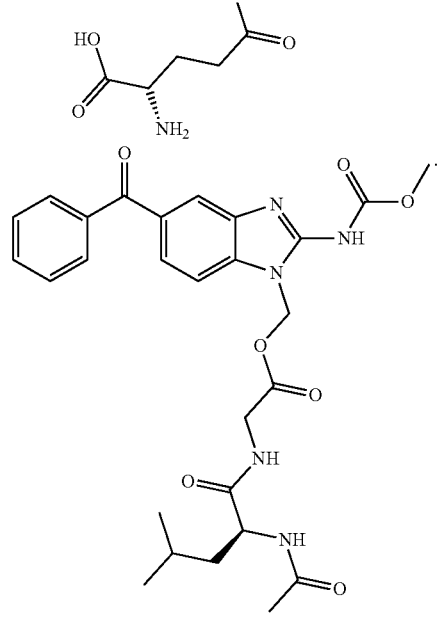

In such embodiments, the amino acid or substituted amino acid is L-glutamic acid and acetyl-L-leucylglycinate, respectively.

As used herein, the term "amino acid" includes moieties having a carboxylic acid group and an amino group. The term amino acid thus includes both natural amino acids (including proteinogenic amino acids) and non-natural amino acids. The term "natural amino acid" also includes other amino acids that can be incorporated into proteins during translation (including pyrrolysine and selenocysteine). Additionally, the term "natural amino acid" also includes other amino acids, which are formed during intermediary metabolism, e.g., ornithine generated from arginine in the urea cycle. The natural amino acids are summarized immediately herein below:

| Natural Amino Acids (Used For Protein Biosynthesis) | | |
|---|---|---|
| Amino acid | 3 letter code | 1-letter code |
| Alanine | ALA | A |
| Cysteine | CYS | C |
| Aspartic Acid | ASP | D |
| Glutamic Acid | GLU | E |
| Phenylalanine | PHE | F |
| Glycine | GLY | G |
| Histidine | HIS | H |
| Isoleucine | ILE | I |
| Lysine | LYS | K |
| Leucine | LEU | L |
| Methionine | MET | M |
| Asparagine | ASN | N |
| Proline | PRO | P |
| Glutamine | GLN | Q |
| Arginine | ARG | R |

| Natural Amino Acids (Used For Protein Biosynthesis) | | |
|---|---|---|
| Amino acid | 3 letter code | 1-letter code |
| Serine | SER | S |
| Threonine | THR | T |
| Valine | VAL | V |
| Tryptophan | TRP | W |
| Tyrosine | TYR | Y |

The natural or non-natural amino acid may be optionally substituted. In one embodiment, the amino acid is selected from proteinogenic amino acids. Proteinogenic amino acids include glycine, alanine, valine, leucine, isoleucine, aspartic acid, glutamic acid, serine, threonine, glutamine, asparagine, arginine, lysine, proline, phenylalanine, tyrosine, tryptophan, cysteine, methionine and histidine. The term amino acid includes alpha amino acids and beta amino acids, such as, but not limited to, beta alanine and 2-methyl beta alanine. The term amino acid also includes certain lactam analogues of natural amino acids, such as, but not limited to, pyroglutamine. The term amino acid also includes amino acids homologues including homocitrulline, homoarginine, homoserine, homotyrosine, homoproline and homophenylalanine.

The terminal portion of the amino acid residue or peptide may be in the form of the free acid i.e., terminating in a —COOH group or may be in a masked (protected) form, such as in the form of a carboxylate ester or carboxamide. In certain embodiments, the amino acid or peptide residue terminates with an amino group. In an embodiment, the residue terminates with a carboxylic acid group —COOH or an amino group —NH$_2$. In another embodiment, the residue terminates with a carboxamide group. In yet another embodiment, the residue terminates with a carboxylate ester.

As disclosed hereinabove, the term "amino acid" includes compounds having a —COOH group and an —NH$_2$ group. A substituted amino acid includes an amino acid which has an amino group which is mono- or di-substituted. In particular embodiments, the amino group may be mono-substituted. (A proteinogenic amino acid may be substituted at another site from its amino group to form an amino acid which is a substituted proteinogenic amino acid). The term substituted amino acid thus includes N-substituted metabolites of the natural amino acids including, but not limited to, N-acetyl cysteine, N-acetyl serine, and N-acetyl threonine. The term substituted amino acid also includes acetyl-L-leucylglycine.

For example, the term "N-substituted amino acid" includes N-alkyl amino acids (e.g., $C_{1-6}$N-alkyl amino acids, such as sarcosine, N-methyl-alanine, N-methyl-glutamic acid and N-tert-butylglycine), which can include $C_{1-6}$ N-substituted alkyl amino acids (e.g., N-(carboxy alkyl) amino acids (e.g., N-(carboxymethyl)amino acids) and N-methylcycloalkyl amino acids (e.g., N-methylcyclopropyl amino acids)); N,N-di-alkyl amino acids (e.g., N,N-di-$C_{1-6}$ alkyl amino acids (e.g., N,N-dimethyl amino acid)); N,N,N-tri-alkyl amino acids (e.g., N,N,N-tri-$C_{1-6}$ alkyl amino acids (e.g., N,N,N-trimethyl amino acid)); N-acyl amino acids (e.g., $C_{1-6}$ N-acyl amino acid); N-aryl amino acids (e.g., N-phenyl amino acids, such as N-phenylglycine); N-amidinyl amino acids (e.g., an N-amidine amino acid, i.e., an amino acid in which an amine group is replaced by a guanidino group).

The term "amino acid" also includes amino acid alkyl esters (e.g., amino acid $C_{1-6}$ alkyl esters); and amino acid aryl esters (e.g., amino acid phenyl esters).

For amino acids having a hydroxy group present on the side chain, the term "amino acid" also includes O-alkyl amino acids (e.g., $C_{1-6}$ O-alkyl amino acid ethers); O-aryl amino acids (e.g., O-phenyl amino acid ethers); O-acyl amino acid esters; and O-carbamoyl amino acids.

For amino acids having a thiol group present on the side chain, the term "amino acid" also includes S-alkyl amino acids (e.g., $C_{1-6}$ S-alkyl amino acids, such as S-methyl methionine, which can include $C_{1-6}$ S-substituted alkyl amino acids and S-methylcycloalkyl amino acids (e.g., S-methylcyclopropyl amino acids)); S-acyl amino acids (e.g., a $C_{1-6}$ S-acyl amino acid); S-aryl amino acid (e.g., a S-phenyl amino acid); a sulfoxide analogue of a sulfur-containing amino acid (e.g., methionine sulfoxide) or a sulfoxide analogue of an S-alkyl amino acid (e.g., S-methyl cysteine sulfoxide) or an S-aryl amino acid.

In other words, the presently disclosed subject matter also includes derivatives of natural amino acids, such as those mentioned above which have been functionalized by simple synthetic transformations known in the art (e.g., as described in "Protective Groups in Organic Synthesis" by T W Greene and P G M Wuts, John Wiley & Sons Inc. (1999)), and references therein.

Examples of non-proteinogenic amino acids include, but are not limited to: citrulline, hydroxyproline, 4-hydroxyproline, β-hydroxyvaline, ornithine, β-amino alanine, albizziin, 4-amino-phenylalanine, biphenylalanine, 4-nitro-phenylalanine, 4-fluoro-phenylalanine, 2,3,4,5,6-pentafluoro-phenylalanine, norleucine, cyclohexylalanine, α-aminoisobutyric acid, α-aminobutyric acid, α-aminoisobutyric acid, 2-aminoisobutyric acid, 2-aminoindane-2-carboxylic acid, selenomethionine, lanthionine, dehydroalanine, γ-amino butyric acid, naphthylalanine, aminohexanoic acid, pipecolic acid, 2,3-diaminoproprionic acid, tetrahydroisoquinoline-3-carboxylic acid, tert-leucine, tert-butylalanine, cyclopropylglycine, cyclohexylglycine, 4-aminopiperidine-4-carboxylic acid, diethylglycine, dipropylglycine and derivatives thereof wherein the amine nitrogen has been mono- or di-alkylated.

II. Pharmaceutical Compositions and Administration

In another embodiment, the present disclosure provides a pharmaceutical composition including one prodrug compound of formula (I), alone or in combination with one or more additional therapeutic agents in admixture with a pharmaceutically acceptable carrier, diluent, or excipient. In particular embodiments, the pharmaceutical composition further comprises one or more therapeutic agents selected from the group consisting of a chemotherapeutic agent, a radiotherapeutic agent, an immunotherapeutic agent, and combinations thereof. One of skill in the art will recognize that the pharmaceutical compositions include pharmaceutically acceptable salts of the compounds described above.

Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids, such as arginate, glutamate, and the like, and salts of organic acids like glucuronic or galactunoric acids and the like (see, for example, Berge et al, "Pharmaceutical Salts," Journal of Pharmaceutical Science, 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methanesulfonate, mucate, napsylate, nitrate, pamoate (embonate), pantothenate, phosphate/diphosphate, polygalacturonate, salicylate, stearate, subacetate, succinate, sulfate, tannate, tartrate, (e.g., (+)-tartrates, (−)-tartrates or mixtures thereof), or teoclate. Other pharmaceutically acceptable salts may be found in, for example, Remington: The Science and Practice of Pharmacy (20th ed.) Lippincott, Williams & Wilkins (2000).

In particular embodiments, the salt is a tri(hydrocarbyl) ammonium or tetra(hydrocarbyl)ammonium salt. In yet more particular embodiments, the salt is selected from the group consisting of a tri($C_1$-$C_8$-alkyl)ammonium, tetra($C_1$-$C_8$-alkyl)ammonium, triphenylammonium, tri(hydroxy-$C_1$-$C_8$-alkyl)ammonium, and tetra(hydroxy-$C_1$-$C_8$-alkyl)ammonium salt. In even more particular embodiments, the salt is selected from the group consisting of a trimethylammonium, triethylammonium, tri(hydroxyethyl)ammonium, tripropylammonium, and tri(hydroxypropyl)ammonium salt.

In therapeutic and/or diagnostic applications, the compounds of the disclosure can be formulated for a variety of modes of administration, including oral (sublingual, buccal), peroral, sublingual, systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid (e.g., solutions, suspensions, or emulsions) or solid dosage forms (capsules or tablets) and administered systemically or locally. The agents may be delivered, for example, in a timed-, controlled-, or sustained-slow release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery. In some embodiments, the pharmaceutical composition is administered orally. In some embodiments, the pharmaceutical composition is administered intravenously. In some embodiments, the pharmaceutical composition is administered intramuscularly. In some embodiments, the pharmaceutical composition is administered intrathecally. In some embodiments, the pharmaceutical composition is administered subcutaneously.

For injection, the agents of the disclosure may be formulated and diluted in aqueous solutions, such as in physiologically compatible buffers, such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers, such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof, such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler, such as lactose, binders, such as starches, and/or lubricants such, as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

III. Methods for Treating a Disease, Disorder, or Condition

The presently disclosed prodrug compounds of formula (I) allow a clinically acceptable dosing paradigm for diseases, disorders, or conditions treatable by MBZ, including cancer, which otherwise might not be possible due to the physicochemical properties of MBZ, e.g., low aqueous solubility, leading to poor oral bioavailability.

Accordingly, in some embodiments, the presently disclosed subject matter provides a method for treating a disease, disorder, or condition, the method comprising administering to a subject in need of treatment thereof a therapeutically effective amount of a compound of formula (I) or a pharmaceutical composition thereof. In some embodiments, the disease, disorder, or condition is cancer.

In general, the presently disclosed methods result in a decrease in the severity of a disease, disorder, or condition in a subject. The term "decrease" is meant to inhibit, suppress, attenuate, diminish, arrest, or stabilize a symptom of a disease, disorder, or condition.

As used herein, the terms "treat," "treating," "treatment," and the like refer to reducing or ameliorating a disease, disorder, or condition, and/or symptoms associated therewith. It will be appreciated that, although not precluded, treating a disease, disorder, or condition does not require that the disease, disorder, condition or symptoms associated therewith be completely eliminated.

In general, the "effective amount" or "therapeutically effective amount" of an active agent refers to the amount necessary to elicit the desired biological response. As will be appreciated by those of ordinary skill in this art, the effective amount of an agent may vary depending on such factors as the desired biological endpoint, the agent to be delivered, the target tissue, the age, weight and gender of the subject, and the like.

In further embodiments, the presently disclosed subject matter includes using a prodrug of formula (I), or a pharmaceutical composition comprising the prodrug of formula (I), optionally in combination with at least one chemotherapeutic agent, at least one radiotherapeutic agent, at least one immunotherapeutic agent, or combinations thereof, to treat cancer. In some embodiments, such treatment includes treatment with any combination of radiotherapy, immunotherapy, photodynamic therapy, proton therapy, and/or surgery.

The term "combination" is used in its broadest sense and means that a subject is administered at least two agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

The timing of administration of the two or more active agents can be varied so long as the beneficial effects of the combination of these agents are achieved. Accordingly, the phrase "in combination with" refers to the administration of at least two active agents, and optionally additional agents either simultaneously, sequentially, or a combination thereof. Therefore, a subject administered a combination of at least two active agents, and optionally additional agents can receive at least two active agents, and optionally additional agents at the same time (i.e., simultaneously) or at different times (i.e., sequentially, in either order, on the same day or on different days), so long as the effect of the combination of all agents is achieved in the subject.

When administered sequentially, the agents can be administered within 1, 5, 10, 30, 60, 120, 180, 240 minutes or longer of one another. In other embodiments, agents administered sequentially, can be administered within 1, 2, 3, 4, 5, 10, 15, 20 or more days of one another. Where the agents are administered simultaneously, they can be administered to the subject as separate pharmaceutical compositions, each comprising either at least one active agent, and optionally additional agents, or they can be administered to a subject as a single pharmaceutical composition comprising all agents. The agents may be administered multiple times.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_a Q_A + Q_b Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

A "chemotherapeutic agent" is used to connote a compound or composition that is administered in the treatment of cancer. Chemotherapeutic agents suitable for use in combination with a prodrug of formula (I), or a pharmaceutical composition comprising a prodrug of formula (I) include, but are not limited to, alkylating agents, such as thiotepa and cyclophosphamide; alkyl sulfonates, such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas, such as carmustine, chlorozotocin, fotemustine, lomustine, nimustine, ranimustine; antibiotics, such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs, such as ancitabine, azacitidine, 6-azauridine, carmofur, cytosine arabinoside, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenishers, such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside (Ara-C); taxoids, e.g., paclitaxel and docetaxel; chlorambucil; gemcitabine; 6-thioguanine; mercaptopurine; platinum analogs, such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine; retinoic acid; esperamicins; capecitabine; and pharmaceutically acceptable salts, acids or derivatives of any of the above. Chemotherapeutic agents also include anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; and pharmaceutically acceptable salts, acids or derivatives of any of the above.

In some embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide, and irinotecan, as well as pharmaceutically acceptable salts, acids, or derivatives of any of these.

In some embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain alternative embodiments, the antimitotic agent comprises a *vinca* alkaloid, such as vincristine, binblastine, vinorelbine, or vindesine, or pharmaceutically acceptable salts, acids, or derivatives thereof.

As used herein, the term "immunotherapeutic agent" refers to a molecule that can aid in the treatment of a disease by inducing, enhancing, or suppressing an immune response in a cell, tissue, organ or subject. Examples of immunotherapeutic agents suitable for use in combination with a prodrug of formula (I), or a pharmaceutical composition comprising a prodrug of formula (I) include, but are not limited to, immune checkpoint molecules (e.g., antibodies to immune checkpoint proteins), interleukins (e.g., IL-2, IL-7, IL-12, IL-15), cytokines (e.g., interferons, G-CSF, imiquimod), chemokines (e.g., CCL3, CCL26, CXCL7), vaccines (e.g., peptide vaccines, dendritic cell (DC) vaccines, EGFRvIII vaccines, mesothilin vaccine, G-VAX, *listeria* vaccines), and adoptive T cell therapy including chimeric antigen receptor T cells (CAR T cells).

As used herein, "radiotherapeutic agent" means an agent which may be used in radiotherapy that acts through damaging cells (e.g., malignant cells) as a target through radiation irradiation. An exemplary radiotherapeutic agent suitable for use in combination with a prodrug of formula (I), or a pharmaceutical composition comprising a prodrug of formula (I) is the titanium peroxide contained in the substrate particle which generates a hydroxyl radial through radiation irradiation, and the hydroxyl radial exerts an action of attacking a target, as described in U.S. Publication No. 2013/0017266, which is incorporated by reference herein in its entirety.

As used herein, a "cancer" in a patient refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. A "tumor," as used herein, refers to all neoplastic cell growth and proliferation, whether malignant or benign, and all precancerous and cancerous cells and tissues. A "solid tumor," as used herein, is an abnormal mass of tissue that generally does not contain cysts or liquid areas. A solid tumor may be in the brain, colon, breasts, prostate, liver, kidneys, lungs, esophagus, head and neck, ovaries, cervix, stomach, colon, rectum, bladder, uterus, testes, and pancreas, as non-limiting examples. In some embodiments, the solid tumor regresses or its growth is slowed or arrested after the solid tumor is treated with the presently disclosed methods. In other embodiments, the solid tumor is malignant. In some embodiments, the cancer comprises Stage 0 cancer. In some embodiments, the cancer comprises Stage I cancer. In some embodiments, the cancer comprises Stage II cancer. In some embodiments, the cancer comprises Stage III cancer. In some embodiments, the cancer comprises Stage IV cancer. In some embodiments, the cancer is refractory and/or metastatic. For example, the cancer may be refractory to treatment with radiotherapy, chemotherapy or monotreatment with immunotherapy. Cancer as used herein includes newly diagnosed or recurrent cancers, including without limitation, acute lymphoblastic leukemia, acute myelogenous leukemia, advanced soft tissue sarcoma, brain cancer, metastatic or aggressive breast cancer, breast carcinoma, bronchogenic carcinoma, choriocarcinoma, chronic myelocytic leukemia, colon carcinoma, colorectal carcinoma, Ewing's sarcoma, gastrointestinal tract carcinoma, glioma, glioblastoma multiforme, head and neck squamous cell carcinoma, hepatocellular carcinoma, Hodgkin's disease, intracranial ependymoblastoma, large bowel cancer, leukemia, liver cancer, lung carcinoma, Lewis lung carcinoma, lymphoma, malignant fibrous histiocytoma, a mammary tumor, melanoma, mesothelioma, neuroblastoma, osteosarcoma, ovarian cancer, pancreatic cancer, a pontine tumor, premenopausal breast cancer, prostate cancer, rhabdomyosarcoma, reticulum cell sarcoma, sarcoma, small cell lung cancer, a solid tumor, stomach cancer, testicular cancer, and uterine carcinoma.

In some embodiments, the cancer is acute leukemia. In some embodiments, the cancer is acute lymphoblastic leukemia. In some embodiments, the cancer is acute myelogenous leukemia. In some embodiments, the cancer is advanced soft tissue sarcoma. In some embodiments, the cancer is a brain cancer. In some embodiments, the cancer is breast cancer (e.g., metastatic or aggressive breast cancer). In some embodiments, the cancer is breast carcinoma. In some embodiments, the cancer is bronchogenic carcinoma. In some embodiments, the cancer is choriocarcinoma. In some embodiments, the cancer is chronic myelocytic leukemia. In some embodiments, the cancer is a colon carcinoma (e.g., adenocarcinoma). In some embodiments, the cancer is colorectal cancer (e.g., colorectal carcinoma). In some embodiments, the cancer is Ewing's sarcoma. In some embodiments, the cancer is gastrointestinal tract carcinoma. In some embodiments, the cancer is a glioma. In some embodiments, the cancer is glioblastoma multiforme. In some embodiments, the cancer is head and neck squamous cell carcinoma. In some embodiments, the cancer is hepatocellular carcinoma. In some embodiments, the cancer is Hodgkin's disease. In some embodiments, the cancer is intracranial ependymoblastoma. In some embodiments, the cancer is large bowel cancer. In some embodiments, the cancer is leukemia. In some embodiments, the cancer is liver cancer. In some embodiments, the cancer is lung cancer (e.g., lung carcinoma). In some embodiments, the cancer is Lewis lung carcinoma. In some embodiments, the cancer is lymphoma. In some embodiments, the cancer is malignant fibrous histiocytoma. In some embodiments, the cancer comprises a mammary tumor. In some embodiments, the cancer is melanoma. In some embodiments, the cancer is mesothelioma. In some embodiments, the cancer is neuroblastoma. In some embodiments, the cancer is osteosarcoma. In some embodiments, the cancer is ovarian cancer. In some embodiments, the cancer is pancreatic cancer. In some embodiments, the cancer comprises a pontine tumor. In some embodiments, the cancer is premenopausal breast cancer. In some embodiments, the cancer is prostate cancer. In some embodiments, the cancer is rhabdomyosarcoma. In some embodiments, the cancer is reticulum cell sarcoma. In some embodiments, the cancer is sarcoma. In some embodiments, the cancer is small cell lung cancer. In other embodiments, the cancer is non-small cell lung cancer. In some embodiments, the cancer comprises a solid tumor. In some embodiments, the cancer is stomach cancer. In some embodiments, the cancer is testicular cancer. In some embodiments, the cancer is uterine carcinoma.

In some embodiments, the cancer is selected from the group consisting of melanoma, non-small cell lung cancer, adrenocortical cancer, colon cancer, including refractory metastatic colon cancer, breast cancer, leukemia, osteosarcoma, medulloblastomas, and gliomas, such as glioblastoma multiforme and pediatric gliomas.

IV. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_{1-10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls. In other embodiments, "alkyl" refers, in particular, to $C_1$-$C_6$ straight-chain alkyls, including $C_1$, $C_2$, $C_3$, $C_4$, $C_5$, and $C_6$ straight-chain alkyls. In yet other embodiments, "alkyl" refers, in particular, to $C_1$-$C_6$ branched-chain alkyls, including $C_1$, $C_2$, $C_3$, $C_4$, $C_5$, and $C_6$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, acylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term "heteroalkyl," by itself or in combination with another term, means, unless otherwise stated, a stable straight or branched chain having from 1 to 20 carbon atoms, including 1, 2, 3, 4, 5, 6, 7, 8, 9, 10, 11, 12, 13, 14, 15, 16, 17, 18, 19, and 20 carbon atoms) or heteroatoms or a cyclic hydrocarbon group having from 3 to 10 carbon atoms or heteroatoms (including 3, 4, 5, 6, 7, 8, 9, and 10 carbon or heteroatoms), or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—O$CH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic monoor multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkylene moiety, also as defined above, e.g., a $C_{1-20}$ alkylene moiety. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system (e.g., 3, 4, 5, 6, 7, 8, 9, or 10 member ring system), including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidinyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated hydrocarbon has one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{2-20}$ (including 2, 3, 4, 5, 6, 7, 8, 9, 10, 11, 12, 13, 14, 15, 16, 17, 18, 19, and 20 carbons, referred to herein as $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, C18, $C_{19}$, and $C_{20}$) inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{2-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—($CH_2$)$_3$—); cyclohexylene (—$C_6H_{10}$—); —CH═CH—CH═CH; —CH═CH—$CH_2$—; —$CH_2CH_2CH_2CH_2$—, —$CH_2$CH═$CHCH_2$—, —$CH_2$CsC$CH_2$—, —$CH_2CH_2$CH($CH_2CH_2CH_3$)$CH_2$—, —($CH_2$)$_q$—N(R)—($CH_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—($CH_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

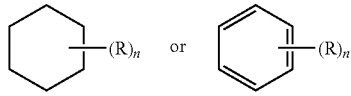

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

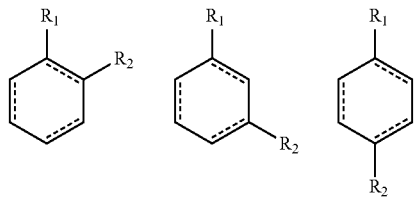

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( $\sim\!\!\sim\!\!\sim\!\!\sim$ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN, CF$_3$, fluorinated C$_{1-4}$ alkyl, and —NO$_2$ in a number ranging from zero to (2m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro(C$_{1-4}$)alkoxo, and fluoro(C$_{1-4}$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The term "cyano" refers to the —C≡N group.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_{1-4}$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —$S(O_2)R$.

The term "sulfoxide" refers to a compound having a sulfinyl group —S(O)R

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)— catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

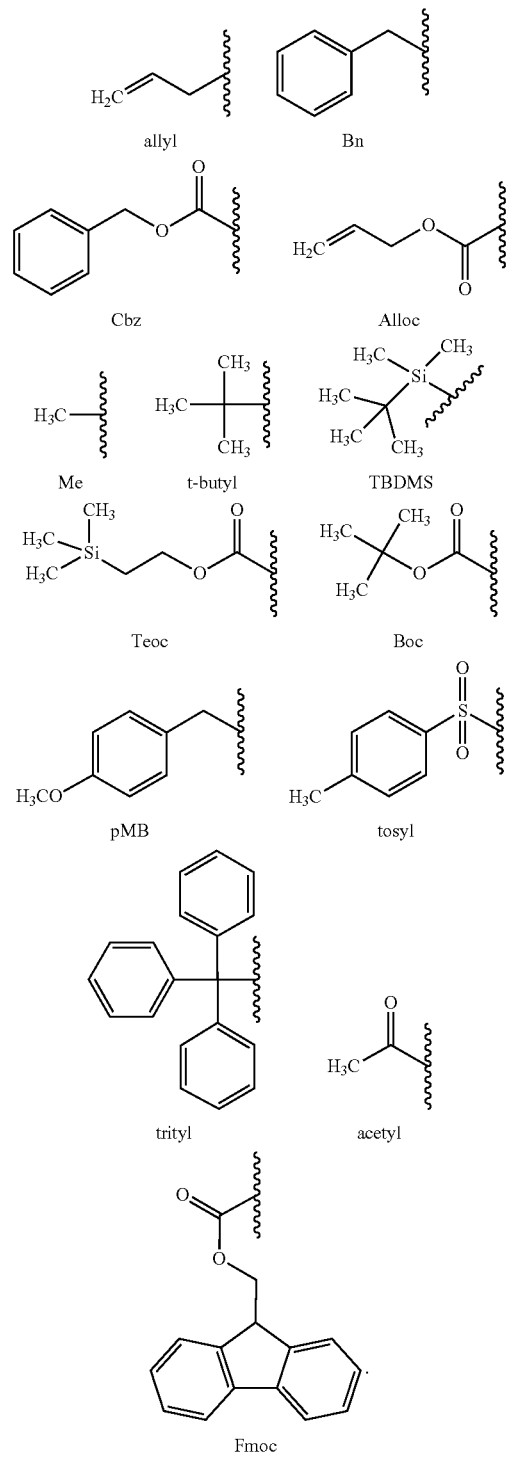

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

N-Substituted Prodrugs of Mebendazole Provide Improved Aqueous Solubility and Oral Bioavailability in Mice and Dogs 1.1 Overview Mebendazole (MBZ) was originally developed as a broad-spectrum anthelmintic for human and veterinary use more than 20 years ago. (Dayan, 2003). More recently, MBZ has been shown to possess anti-cancer properties in a broad range of pre-clinical studies across various cancer types, such as adrenocortical carcinoma, (Martarelli, et al., 2008) non-small cell lung cancer, (Sasaki, et al., 2002; Mukhopadhyay, et al., 2002) gastric cancer, (Pinto, et al., 2015) colon cancer, (Nygren, et al., 2013) melanoma, (Doudican, et al., 2008) glioblastoma, (De Witt, et al., 2017) medulloblastoma (Bai, et al., Neuro-Oncology, 2015), and glioblastoma multiforme (Bai, et al., 2011). MBZ's anticancer efficacy is thought to be due to its polypharmacology, including its ability to inhibit microtubule formation, (De Witt, et al., 2017) VEGFR2 kinase, (Bai, et al., Neuro-Oncology, 2015) the hedgehog pathway, (Larsen, et al., 2015) and other kinases implicated in cancers including BCR-ABL and BRAF (Nygren, et al., 2013). Recently, MBZ-C, the most bioavailable MBZ polymorph, has been used in exploratory clinical studies for brain cancer. (NCT01729260; NCT01837862; NCT02644291; NCT02201381).

Despite these encouraging results, the development of MBZ for indications requiring systemic availability remains challenging. MBZ is a Biopharmaceutics Classification System (BCS) class II drug (Carlert, et al., 2012), which displays poor physicochemical properties including low aqueous solubility and poor oral bioavailability, (Dayan, 2003), despite its optimal partition coefficient (c Log P=3.1). MBZ's low solubility is hypothesized to be due to its planar structure causing strong stacking interactions in the crystal lattice, which are reinforced by intermolecular hydrogen bonds. (Martins, et al., 2009). In a pilot human pharmacokinetic study with one subject using intravenous and oral administration of [$^3$H]-mebendazole, the oral bioavailability of MBZ was found to be 17%. (Dawson, et al., 1982). A second study in five subjects, confirmed these results calculating the bioavailability as 22%, with a variable range of 12-35%. (Dawson, et al., 1985).

Multiple strategies have been investigated to improve the bioavailability of MBZ. MBZ exists in three polymorphic forms, A, B, and C, (MBZ-A, MBZ-B and MBZ-C, respectively), which have been investigated for their differences in physicochemical properties including solubility, (Himmelreich, et al., 1971) dissolution rate, and therapeutic effects. (Bai, et al., 2015; Rodriguez-Caabeiro, et al., 1987). MBZ-C is the clinically preferred polymorph (Brits, et al., 2010) due to its improved solubility over MBZ-A (Honorato, et al., 2012; Swanepoel, et al., 2003). Furthermore, MBZ-C displayed less toxicity than MBZ-B (Rodriguez-Caabeiro, et al., 1987; Charoenlarp, et al., 1993) and was found to exhibit higher plasma AUC levels and brain to plasma (B/P) ratios as compared to MBZ-A and MBZ-B. (Bai, et al., 2015). In addition to characterizing the different polymorphic forms, salt forms and co-solvent strategies have been investigated for enhancing its solubility. Specifically, the MBZ mesylate salt was shown to improve solubility, (de Paula, et al., 2013), whereas MBZ oil and co-solvent based formulations (e.g., with oleic acid, glycerol trioleate, span 80, tween 80, soybean oil, olive oil, polyethylene glycol) (Liu, et al., 2012; Liu, et al., 2014; Daniel-Mwuambete, et al., 2003; Dawson, et al., Br J Clin Pharmacol, 1985, 19, 87-90; Chiba, et al., 1991) were shown to improve MBZ's plasma exposures following oral administration. These latter methods, however, were limited to administration as oral suspensions leading to increased variability in exposure.

Prodrug approaches to improve MBZ's aqueous solubility also have been investigated focusing on 4-amino-3-(3'-methoxycarbonyl-2'-thioureido)benzophonone (Dawson, et al., 1983) or N-alkoxycarbonyl MBZ. (Nielsen, et al., 1994). These reports, however, profiled limited chemistry focusing on simple acylations of the benzimidazole nitrogens and a single 4-amino-3-(3'-methoxycarbonyl-2'-thioureido)benzophonone analog. Moreover, while the N-alkoxycarbonyl prodrugs did show increased solubility compared to MBZ, they were only evaluated in vitro, with no systematic testing in vivo to confirm improvements over MBZ. (Nielsen, et al., 1994). The 4-amino-3-(3'-methoxycarbonyl-2'-thioureido) benzophonone was evaluated in an oral pharmacokinetic study in rats and showed a 2-fold improvement in plasma exposure versus equimolar oral MBZ; oral bioavailability was not reported as reference intravenous MBZ studies were not performed. Moreover, information regarding which MBZ polymorph was used for comparative analysis was not provided. (Dawson, et al., 1983).

The presently disclosed subject matter provides a prodrug approach to improve the aqueous solubility of MBZ by making N-acyloxy methyl and N-phosphono-oxymethyl prodrugs. In particular embodiments, eight representative MBZ prodrugs with improved aqueous solubility compared to MBZ-C, of which seven were evaluated in mice and showed increased plasma exposure following oral administration. When compared to equimolar MBZ-C, one prodrug, with a phosphono-oxomethyl alkyl promoiety, showed a >10,000-fold improvement in solubility and a 2.2- and 3.8-fold improvement in oral bioavailability in mice and dogs, respectively.

1.2 Results

1.2.1 Chemistry

A selection of representative was used to derivatize MBZ. Pivaloyloxymethyl (POM, 1) and isopropyloxycarbonyloxymethyl (POC, 2) promoieties, which have shown previous success for phosphate containing compounds (Majer, et al., 2016; Dando, et al., 2003; Kearney, et al., 2004; Chanteux, et al., 2005) were used to prepare prodrugs 1, 2. MBZ was alkylated (Scheme 1) in DMSO with the requisite chlorides, chloromethyl pivalate for 1 and chloromethyl isopropyl carbonate for 2, leading to final prodrugs with the POM (1) and POC (2) promoieties. To further increase solubility of MBZ prodrugs, the pivalic acid in 1 was replaced by several amino acids or dipeptides. Unfortunately, all prodrugs with a free amino group (e.g., 14, Scheme 2) were too unstable in aqueous environment, even at neutral or mildly acidic conditions, making characterization and an in vitro assessment challenging.

When the free amino group, however, was acetylated as in acetyl-L-leucinyl-glycinyloxy methyl compound 7, the prodrug was sufficiently stable to be tested. Prodrug 7 (Scheme 1) was prepared in a similar fashion as discussed above, by reacting MBZ with chloromethyl (tert-butoxycarbonyl)glycinate to yield 3. Intermediate 3 was then deprotected in acidic conditions and its peptide chain extended by standard method using a BOC protection to form 6. The amine was then deprotected and acetylated to obtain prodrug 7, predominately composed of the $N^1$ isomer. The succinyloxy methyl promoiety with a free carboxylate was used in prodrug 8. The succinic acid was introduced in a similar manner, by alkylating MBZ using tert-butyl (chloromethyl) succinate to produce intermediate 4, which was hydrolyzed to 8 using TFA.

Another strategy employed to increase the solubility of MBZ was to introduce a glucose moiety attached via the primary 6-hydroxy group (9), which could then be hydrolyzed in vivo to MBZ. Prodrug 9 (Scheme 1) was prepared by alkylation of MBZ with chloromethyl (((2R,3R,4S,5R,6R)-3,4,5,6-tetrakis((trimethylsilyl)oxy)tetrahydro-2H-pyran-2-yl)methyl) carbonate to yield intermediate 5, which was hydrolyzed by TFA to 9. (Fan, et al., 2011).

The phosphonooxomethyl promoiety which has been successfully employed to improve aqueous solubility and bioavailability of water insoluble drugs (Ueda, et al., 2003; Chassaing, et al., 2008; DeGoey, et al., 2009) was used for the synthesis of Compound 11. Compound 11 was further modified with an additional POC by masking the phosphate to obtain 12. The POC was found to compensate for the highly hydrophilic nature of the phosphonooxymethyl, which led to an increase in the c Log P to a more favorable value of 3.9 for 12, as compared to a value of 0.79 for the free phosphate 11. To prepare 11 and 12 (Scheme 2), MBZ was first reacted with di-tert-butyl (chloromethyl) phosphate to produce intermediate 10. Prodrug 11 was then synthesized by deprotection of 10 with TFA to the free phosphate. 11 was then alkylated by chloromethyl isopropyl carbonate to yield 12. Compound 14 was synthesized by reaction MBZ with N-Boc-glutamic acid-α-t-butyl-γ-chloromethyl ester and removal of the protecting groups from the intermediate 13 by TFA.

All prodrugs were obtained as a mixture of their $N^1$ and $N^3$ positional isomers resulting from the undifferentiated substitution of both benzimidazole nitrogen atoms. For simplicity, however, all figures are shown with promoeities on the $N^1$ position. The formation of positional isomer ($N^2$) was not observed in any prodrug. The ratios of the positional isomers differed for individual prodrugs and are detailed in the Experimental Section herein below. Since the hydrolysis of either $N^1$ and $N^3$ positional isomers results in the release of the same active product (i.e., MBZ), all the biological data was performed on the mixtures. This approach is somewhat analogous to the situation of prodrugs containing chiral center in the promoiety (fosinopril, cefuroxime axetil, cefpodoxime proxetil) (Beaumont, et al., 2003; Klepser, et al., 1995) that are marketed as mixtures of diastereomers.

1.2.2 Solubility and Chemical Stability Assessment

The prodrugs were screened for aqueous solubility in 0.01 M PBS using a modified form of the shake flask method (Zhou, et al., 2007). All of the prodrugs displayed increased solubility (as shown in FIG. 1 and Table 2) compared to MBZ-C, with 7, 8, and 9 showing greater than 200-fold improvement. Compounds 11 and 12 with the charged phosphonooxomethyl and POC substituted phosphonooxomethyl promoiety, respectively, showed the highest increase, with 12 displaying a >10,000-fold improvement over MBZ-C (solubility of 0.4 µg/mL versus 14,000 µg/mL, respectively).

TABLE 2

Aqueous Stability of MBZ Prodrugs in PBS Buffer

| Compound | Solubility (µg/mL) |
|---|---|
| MBZ-C | 0.4 |
| 1 | 1.4 |
| 2 | 2.8 |
| 18 | 0.1 |
| 12 | 14003.4 |
| 7 | 85.5 |
| 8 | 386.1 |
| 9 | 220.0 |

TABLE 2-continued

Aqueous Stability of MBZ Prodrugs in PBS Buffer

| Compound | Solubility (μg/mL) |
|---|---|
| 14 | 450.6* |
| 15 | 0.5 |
| 16 | nd** |
| 17 | nd** |

*The solubility of analog 14 was determined in water due to chemical instability in PBS at pH 7.4.
**nd = no data.

Prodrugs were also tested for chemical stability in 0.01 M PBS for 60 min at 37° C. by monitoring intact prodrug using LC-MS. All prodrugs were stable over the assay conditions except 14 which showed high instability with 0% remaining at 60 min, respectively. Thus prodrug 14 was not assessed in assays due to its significant instability in PBS at pH 7.4.

1.2.3 Metabolic Stability Assessment

In addition to solubility, all prodrugs were screened for in vitro metabolic stability in mouse jejunum homogenate, liver microsomes and plasma (see Table 3) to characterize their bioconversion to MBZ. The screening paradigm was designed to confirm activation of prodrugs to MBZ following oral administration in these highly metabolic sites. Initial screening was done in mouse jejunum homogenate by incubating the compounds for 60 min. The results showed that 2, 9 and 12 were completely metabolized (>95%) and 1, 7, 11 and 8 were highly metabolized (63-82%). Following jejunum stability, the prodrugs were screened in mouse liver microsomes. After a 60 min incubation, 1 and 2 showed complete metabolism (>95%), 7, 8, 9, and 12 were highly metabolized (71-86%) and 11 was stable in liver microsomes. Lastly, screening in mouse plasma showed that after a 60 min incubation, prodrugs containing the POM (1), the POC (2), and the methyl acetyl-L-leucylglycinate (7) promoieties were completely metabolized (>95%), prodrug 9, containing a methyl (glucosyl)methyl carbonate promoiety was highly metabolized (82%), while prodrugs containing the methyl 4-oxobutanoic acid (8) and methyl (isopropoxycarbonyloxy)methyl phosphate (12) promoieties showed the least metabolism (<30%) in mouse plasma.

TABLE 3

In vitro metabolic stability of MBZ Prodrugs

| Compound | R | Intestinal homogenate | Liver microsomes | Plasma |
|---|---|---|---|---|
| MBZ-C | H | 100 ± 2 | 100 ± 5 | 100 ± 5 |
| 1 | 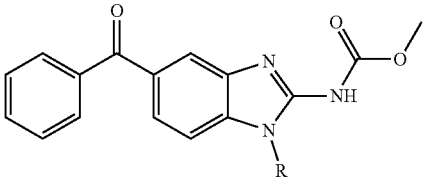 | 37 ± 2 | 0 ± 0 | 4 ± 0 |
| 2 | 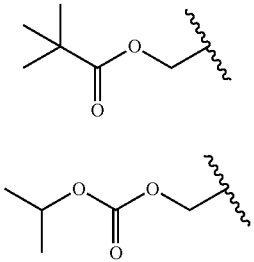 | 0 ± 0 | 0 ± 0 | 0 ± 0 |
| 7 | 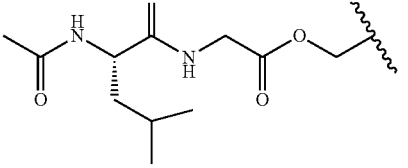 | 18 ± 1 | 29 ± 1 | 0 ± 0 |
| 8 | 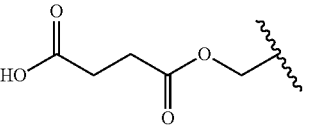 [SMILES: *COC(=O)CCC(=O)O] | 30 ± 2 | 24 ± 0 | 78 ± 1 |

TABLE 3-continued

In vitro metabolic stability of MBZ Prodrugs

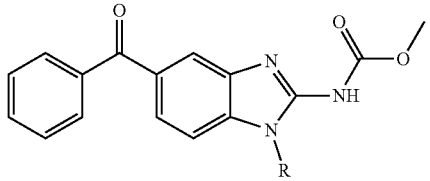

| Compound | R | In vitro stability in mouse (% remaining at 60 min) | | |
| --- | --- | --- | --- | --- |
| | | Intestinal homogenate | Liver microsomes | Plasma |
| 9 | 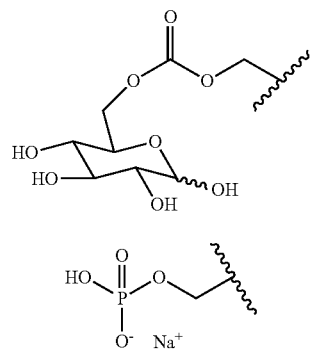 | 4 ± 0 | 27 ± 0 | 18 + 0 |
| 11 | 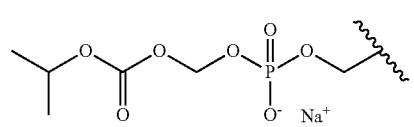 [SMILES: *COP(=O)([O-])OCOC(=O)OC(C)C ; [Na+]] | 35 ± 4 | 100 ± 2 | 62 ± 1 |
| 12 | 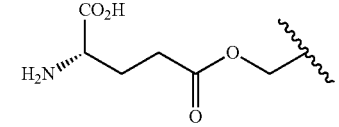 [SMILES: *COC(=O)CC[C@H](N)C(=O)O] | 1 ± 0 | 14 ± 0 | 73 ± 3 |
| 14 | 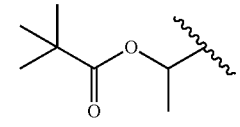 [SMILES: *C(C)OC(=O)C(C)(C)C] | n/a[#] | n/a[#] | n/a[#] |
| 15 | 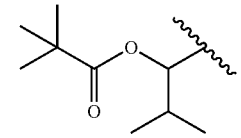 [SMILES: *C(OC(=O)C(C)(C)C)C(C)C] | 60 | 38 | 85 |
| 16 | 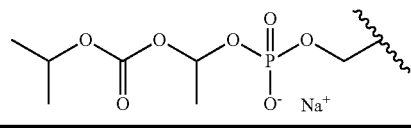 | 100 | 90 | 96 |
| 17 |  | 46 | 82 | 89 |

[#]n/a: Data were not attainable due to chemical instability

1.2.4 Single Time Point Oral Pharmacokinetic Comparison of MBZ-C and Prodrugs in Mice All prodrugs were screened in a single time-point mouse pharmacokinetic study in comparison to MBZ-C (FIG. 2). MBZ-C and the prodrugs were administered via oral gavage at equivalent doses and MBZ levels in plasma were analyzed by LC-MS at 1 h post drug administration. When directly compared to MBZ-C (2.86±0.25 nmol/mL), oral administration of 7 (8.72±0.63 nmol/mL), 11 (8.53±2.33 nmol/mL) and 12 (10.35±2.57 nmol/mL) showed statistically significant improvement in the exposure of plasma MBZ, with 12 showing the best profile with a 3.6-fold improvement over MBZ-C. Given this, 12 was further characterized for full pharmacokinetic time course studies in both mice and dogs as described.

1.2.5 Pharmacokinetic Profile of Intravenous (IV) MBZ-C in Mice and Dogs

Referring now to FIG. 3A, FIG. 3B, and Table 4, to calculate exact pharmacokinetic parameters (specifically oral bioavailability) of MBZ from 12, it was imperative to conduct intravenous (IV) pharmacokinetic analysis of MBZ. To the inventors' knowledge, IV pharmacokinetics of MBZ-C in preclinical studies has not been previously reported, likely due to its poor aqueous solubility. Using a co-solvent system comprising of 1% DMSO and 10% CremophorEL formulation, however, MBZ was successfully administered via IV at a dose of 1.5 mg/kg in mice (FIG. 3A) and a dose of 0.3 mg/kg in dog (FIG. 3B). In mice, IV MBZ-C administration at 1.5 mg/kg led to a $C_{max}$ of 5.3 nmol/mL at 5 min post-dose, with an $AUC_{0-t}$ of 2.7 nmol·h/mL. In beagle dogs, IV MBZ-C administration at 0.3 mg/kg with the same formulation resulted in a $C_{max}$ of 2.2 nmol/mL at 5 min and an $AUC_{0-t}$ of 0.9 nmol·h/mL. The half-lives for MBZ-C were short following IV administration with a value of 0.73 h and 0.72 h in mice and dog respectively. The volume of distribution (Vd) in mice was calculated to be 1.4 L/kg and in dog 1.3 L/kg suggesting low to moderate distribution to tissue components. Lastly, the clearance values were 27 ml/min/kg and 22 ml/min/kg in mice and dog, respectively, suggesting low systemic clearance.

TABLE 4

MBZ Pharmacokinetics in Mice and Dogs Following IV Administration

| Treatment | Species | Dose (mg/kg) | $C_{max}$ (nmol/mL) | $t_{1/2}$ (h) | $T_{max}$ (h) | $AUC_{0-t}$ (nmol·h/mL) | Cl (ml/min/kg) | Vd (L/kg) |
|---|---|---|---|---|---|---|---|---|
| MBZ-C | Mouse | 1.5 | 5.3 ± 0.2 | 0.73 | 0.083 | 2.7 ± 0.1 | 27.4 ± 1.4 | 1.4 ± 0.25 |
| MBZ-C | Dog | 0.3 | 2.2 | 0.72 | 0.083 | 0.9 | 22.2 | 1.3 |

1.2.6 Pharmacokinetic Profile of Oral MBZ-C and Prodrug 12 in Mice and Dog

Referring now to FIG. 4A, FIG. 4B, Table 5, and Table 6, to determine the oral bioavailability in mice, MBZ-C and 12 were dosed at an equivalent 30 mg/kg peroral (PO) dose in 5% ethanol, 5% polysorbate 80 in 90% saline. 12 showed a 2.4-fold enhancement in $C_{max}$ compared to MBZ-C (12.2 nmol/mL at 0.5 h for 12 versus 5.1 nmol/mL at 1 h for MBZ-C). Prodrug 12 also displayed a 2.2-fold enhanced $AUC_{0-t}$ (27.9 nmol·h/mL for 12 versus 12.9 nmol·h/mL for MBZ-C), with calculated oral bioavailability (% F) of 24% and 52% MBZ from MBZ-C or 12 administration, respectively (FIG. 4A). Brain concentrations of MBZ were also measured in tandem. In mouse brain (FIG. 4B), 12 showed a 2.3-fold improvement in $C_{max}$ over MBZ-C (11.7 nmol/mL at 0.5 h for 12 versus 5.1 nmol/mL at 1 h for MBZ-C) and a 1.7-fold increase in brain $AUC_{0-t}$ (21.9 nmol·h/mL for 12 versus 13.1 nmol·h/mL for MBZ-C). The brain to plasma (B/P) ratio of MBZ stayed consistent with a B/P ratio of 1 for MBZ-C and 0.8 for 12 as shown in FIG. 4C. Further, no intact prodrug was detected in either brain or plasma samples at any time point suggesting complete conversion to MBZ prior to systemic absorption. These pharmacokinetic results also corroborated the in vitro metabolism studies as 12 was unstable in intestinal tissue homogenate.

TABLE 5

MBZ Plasma Pharmacokinetic Parameters in Mice after Oral Administration

| Treatment | Route | Dose (mg/kg) | $C_{max}$ (nmol/mL) | $T_{max}$ (h) | $AUC_{0-t}$ (nmol·h/mL) | % F |
|---|---|---|---|---|---|---|
| MBZ-C | PO | 30.0 | 5.1 ± 0.9 | 1 | 12.9 ± 2.1 | 24 |
| 12 | PO | 30.0 eq. | 12.2 ± 0.5 | 0.5 | 27.9 ± 0.8 | 52 |

TABLE 6

Brain Pharmacokinetic Parameters in Mice after Oral Administration

| Treatment | Route | Dose (mg/kg) | $C_{max}$ (nmol/g) | $T_{max}$ (h) | $AUC_{0-t}$ (nmol·h/g) | B/P |
|---|---|---|---|---|---|---|
| MBZ-C | PO | 30.0 | 5.1 ± 0.8 | 1 | 13.1 ± 4.2 | 1 |
| 12 | PO | 30.0 eq. | 11.7 ± 0.8 | 0.5 | 21.9 ± 2.0 | 0.8 |

Referring now to FIG. 5 and Table 7, MBZ-C and 12 also were administered to male beagle dogs (FIG. 5) as a single PO dose of 2.5 mg/kg equivalent MBZ in a formulation of 5% ethanol, 5% polysorbate 80 in 90% saline. Compared to MBZ-C, 12 showed a 3.5-fold higher $C_{max}$ (0.7 nmol/mL at 2 h for 12 versus 0.2 nmol/mL at 2 h for MBZ-C) and 3.8-fold higher $AUC_{0-t}$ (3.0 nmol·h/mL for 12 versus 0.8 nmol·h/mL for MBZ-C). The calculated oral bioavailability was 11% and 41% of MBZ from MBZ-C or 12 administration, respectively, suggesting almost a 4-fold improvement in dogs from 12. Similar to mouse no intact prodrug was observed in human plasma following oral administration of 12.

TABLE 7

MBZ Plasma Exposure in Male Beagle Dogs after Oral Administration

| Treatment | Route | Dose (mg/kg) | $C_{max}$ (nmol/mL) | $T_{max}$ (h) | $AUC_{0-t}$ (nmol·h/mL) | % F |
|---|---|---|---|---|---|---|
| MBZ-C | PO | 2.5 | 0.2 | 2 | 0.8 | 11 |
| 12 | PO | 2.5 eq. | 0.7 | 2 | 3.0 | 41 |

1.2.7 Solubility and Stability Assessment

The aqueous solubility was determined as previously reported using the shake-flask procedure published by Zhou, et al., 2007. The compound was added to PBS buffer (0.01 M) and shaken for 24 h at 37° C. to ensure saturation. After 24 h, the solution was centrifuged (10,000 rpm, 2 min, RT) filtered (0.45 μm PTFE) and the filtrate was diluted appropriately (i.e. neat, 1/10, 1/100, 1/1000) and the concentration of compound was determined using LC/MS.

Prodrug chemical stability was measured by the addition of 1 μL, of 10 mM DMSO stock solution to 1 mL of preheated (37° C.) 0.1 M PBS, resulting in a final concentration of 10 μM. The mixture was vortex mixed for 30 sec, and then incubated at 37° C. At specified time points 100 μL of the mixture was removed and extracted with 300 μL of cold acetonitrile (0° C.) with internal standard. This mixture was further diluted with 400 μL of water and the resulting solution was analyzed by LC-MS.

1.2.8 In Vitro Stability Assessment

In vitro stability studies were done using mouse jejunum homogenate, mouse liver microsomes or naïve mouse plasma. For mouse jejunum homogenate stability study, washed mouse jejunum was diluted 10-fold in 0.1 M potassium phosphate buffer, and homogenized using probe sonication. Crude homogenate was then aliquoted to 1 mL and the homogenate was spiked with 10 μM of compound. Liver microsome stability assay was performed in 100 mM potassium phosphate buffer, pH 7.4, and reactions were initiated by addition of the liver microsomes to the incubation mixture (compound final concentration was 10 μM; 0.5 mg/mL microsomes). The plasma stability of the prodrugs was determined by spiking (10 μM) of prodrugs in 1 mL of plasma and incubating in an orbital shaker at 37° C. All the stability studies were conducted at predetermined times (0 and 60 min), where 100 μL aliquots of the mixture in triplicate were removed and the reaction was quenched by addition of three times the volume of ice cold acetonitrile spiked with the internal standard (losartan: 0.5 μM). The samples were vortex mixed for 30 sec and centrifuged at 10000×g for 10 min at 4° C. Fifty microliter of the supernatant was diluted with 50 μL water and transferred to a 2504 polypropylene vial sealed with a Teflon cap. Prodrug disappearance was monitored over time using liquid chromatography and tandem mass spectrometry (LC-MS/MS).

1.2.9 Bioanalysis

Briefly, prodrugs were analyzed on a Thermo Scientific Accela UPLC system coupled to Accela open autosampler at ambient temperature with an Agilent Eclipse Plus column (100×2.1 mm i.d.) packed with a 1.8 μm C18 stationary phase. The autosampler was temperature controlled and operated at 10° C. The mobile phase used for the chromatographic separation was composed of acetonitrile/water containing 0.1% formic acid and with a flow rate of 0.4 mL/min for 4.5 min using gradient elution. The column effluent was monitored using TSQ Vantage triple-quadrupole mass-spectrometric detector, equipped with an electrospray probe set in the positive ionization mode. Samples were introduced into the ionization source through a heated nebulized probe (350° C.). Disappearance of prodrugs was measured from ratio of peak areas of analyte to IS.

1.2.10 Pharmacokinetic Studies in Mice

All pharmacokinetic studies in mice were conducted according to protocols approved by the Animal Care and Use Committee at Johns Hopkins University. Male CD-1 mice between 25 and 30 g were obtained from Harlan, and maintained on a 12-h light-dark cycle with ad libitum access to food and water. For PO administration, prodrugs or MBZ-C were prepared immediately prior to dosing in 5% ethanol, 5% polysorbate 80, 90% water and administered to male mice as a single PO dose by oral gavage of 30 mg/kg MBZ equivalent. For IV administration, MBZ-C was dissolved immediately prior to dosing in 1% DMSO, 10% Cremophor EL, 89% saline and was administered to mice as a single IV dose of 1.5 mg/kg. The mice were sacrificed at specified time points post drug administration. For collection of plasma and brain tissue, animals were euthanized with $CO_2$, and blood samples were collected in heparinized microtubes by cardiac puncture. Tissues were dissected and immediately flash frozen (−80° C.). Blood samples were spun at 2,000×g for 15 min, plasma was removed and stored at −80° C. until LC/MS analysis. Prior to extraction, frozen samples were thawed on ice. The calibration curves were developed using plasma and brain from naïve animals as a matrix. Plasma samples (50 μL), were processed using a single liquid extraction method by addition of 3004 of acetonitrile as with internal standard (losartan: 0.5 μM), followed by vortex mixing for 30 sec and then centrifugation at 10,000×g for 10 min at 4° C. For brain tissue, homogenized samples were vortex mixed and centrifuged as above. A 104 aliquot of supernatant was diluted with 354 of acetonitrile and mixed with 50 μL water containing 0.5 μM losartan as internal standard. Extracts were centrifuged at 10,000×g for 10 min at 4° C. Supernatants were transferred to 2504 polypropylene autosampler vials sealed with a Teflon cap. A volume of 34 was injected onto the ultra-performance liquid chromatography (UPLC) instrument for quantitative analysis by LC-MS/MS.

1.2.11 Pharmacokinetics Studies in Beagle Dogs

The dog pharmacokinetic study was conducted in accordance with the guidelines recommended in Guide for the Care and Use of Laboratory Animals and was approved by the Absorption Systems (San Diego, Calif.) Institutional Animal Care and Use Committee. MBZ-C and 12 were administered to male beagle dogs (n=2 group) as a single PO dose of 2.5 mg/kg equivalent (5.4 mg/kg for 12). Additionally, MBZ-C was administered to male beagle dogs (n=2) as a single IV dose at 0.3 mg/kg. Blood samples were collected from the jugular vein (~1 mL) via direct vein puncture at specified time points, placed into sodium heparin tubes, and maintained on wet ice until processing. Blood samples were centrifuged at 3,000×g, for 5 min at 4° C. Plasma samples was collected in tubes and stored at −80° C. until bioanalysis.

1.2.12 Bioanalysis

Calibration curves over the range 0.001-50 nmol/g [MBZ] in plasma and brain were constructed from the peak area ratio of the analyte to the internal standard using linear regression with a weighing factor of 1/(nominal concentration). Correlation coefficient of greater than 0.99 was considered to be acceptable in the analytical runs for all analytes.

Briefly, chromatographic analysis was performed using an Accela™ ultra high-performance system consisting of an analytical pump, and an autosampler coupled with TSQ Vantage mass spectrometer (Thermo Fisher Scientific Inc., Waltham, Mass.). Separation of the analyte was achieved using Agilent Eclipse Plus column (100×2.1 mm i.d.) packed with a 1.8 μm C18 stationary phase. The mobile phase consisted of 0.1% formic acid in acetonitrile and 0.1% formic acid in water with gradient elution, starting with 10% (acetonitrile) linearly increasing to 99% up to 2.5 min, maintaining at 99% (2.5-3.5 min) and re-equilibrating to 10% by 4.5 min. The $[M+H]^+$ ion transition of MBZ (m/z 295.966→264.096) and losartan (IS) (m/z 423.200→207.107, 180.880).

1.2.13 Pharmacokinetic Analysis of MBZ

The pharmacokinetic parameters of MBZ were calculated using non-compartmental method as implemented in the computer software program Phoenix WinNonlin version 6.4 (Certara USA, Inc., Princeton, N.J.). The maximum plasma concentration ($C_{max}$) and time to $C_{max}$ ($T_{max}$) were the observed values. The area under the plasma concentration time curve (AUC) value was calculated to the last quantifiable sample ($AUC_{last}$) by use of the log-linear trapezoidal rule. The brain to plasma partition coefficients were calculated as a ratio of mean AUCs ($AUC_{0-t,brain}/AUC_{0-t,plasma}$).

1.2.14 Statistical Analysis

For single time point study where mice were dosed with either MBZ-C and other prodrugs, MBZ plasma concentrations were statistically compared by one-way ANOVA with Dunnett's post hoc test. The a priori level of significance for all analyses was defined as $p<0.05$.

1.2.15 Summary

The anthelmintic MBZ has been used since the 1970s for the treatment of parasitic worm infections, and has more recently shown potential for strong effectiveness against a variety of cancers supported by both preclinical and clinical studies. The main challenges with MBZ have been its poor oral bioavailability due to poor physicochemical properties. Previous studies have attempted to increase MBZ's bioavailability using oil-based formulations and prodrug strategies, although with limited success. The presently disclosed subject matter explores alternative N-linked substituents, including acyloxy methyl, aminoacyloxy methyl, and substituted phosphonooxy methyl promoeities. Employing a comprehensive evaluation paradigm with aqueous solubility, jejunum, liver and plasma stability, and oral and IV in vivo pharmacokinetic analyses in two species, several prodrugs with improved solubility and pharmacokinetics as compared to MBZ-C were identified. Of the seven prodrugs evaluated, prodrug 12 containing the ((isopropoxycarbonyl) oxy)methoxy)phosphoryl) oxy)methyl promoiety, displayed the largest increase in aqueous solubility (>10,000-fold) and significant improvement in MBZ plasma exposure following oral administration in mouse and dog (2.2-fold and 3.8 higher plasma $AUC_{0-t}$ respectively). The presently disclosed results are consistent with other prodrugs containing N-phosphonooxymethyl promoeities that have also shown enhanced solubility and bioavailability (Ueda, et al., 2003; Chassaing, et al., 2008; DeGoey, et al., 2009).

Future efforts will focus on obtaining and characterizing the $N^1$ and $N^3$ positional isomers of 12 to evaluate any differences in their metabolic rate of MBZ liberation. Because no intact 12 was observed in plasma, however, it is likely that both isomers underwent complete hydrolysis prior to systemic absorption. Given this, the two isomers may not have differential impact on MBZ bioavailability and distribution. Overall, the presently disclosed findings show that a prodrug approach can improve the solubility and pharmacokinetic parameters of MBZ, improving MBZ as a therapeutic agent for systemic applications.

Example 2

Chemical Synthesis

Scheme 1. Synthesis of Prodrugs 1-2, 7-9, 15, 16, and 18.

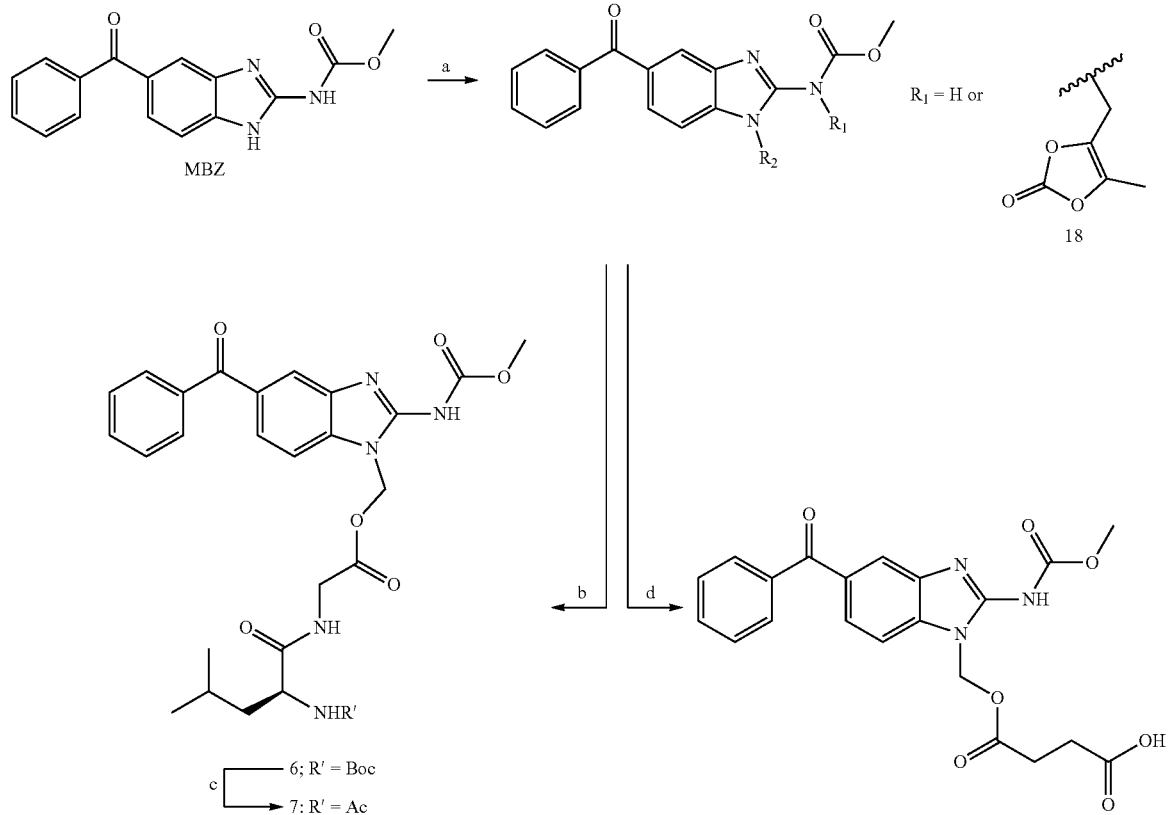

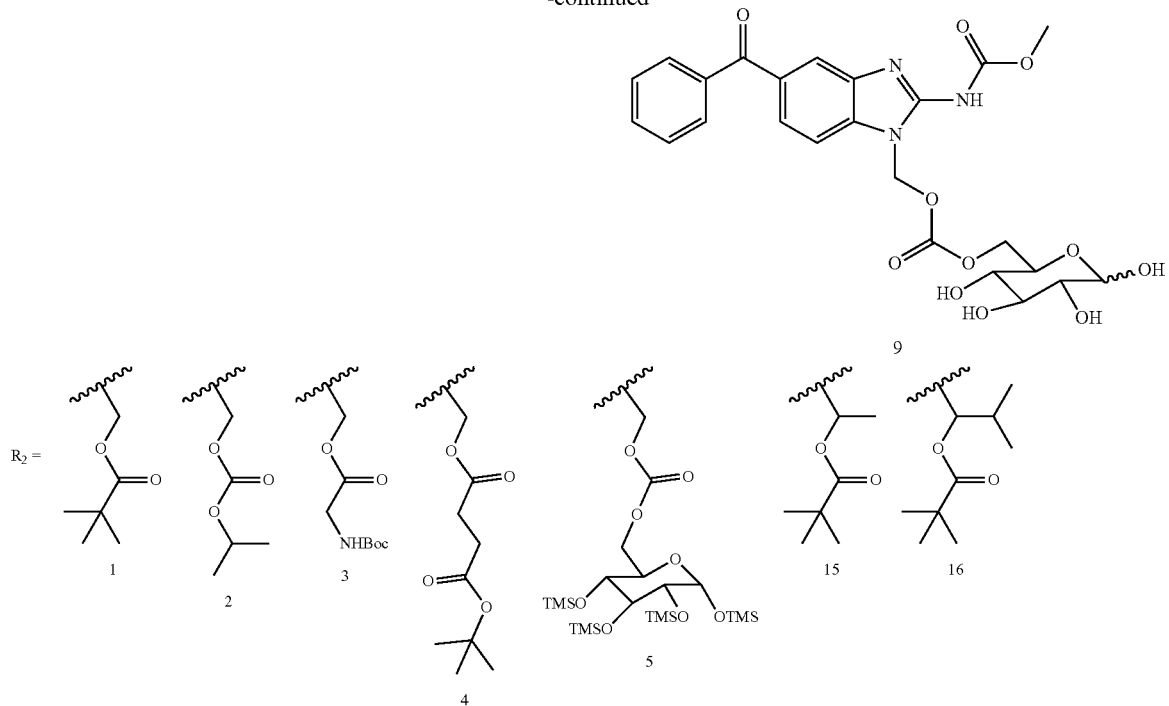
Reagents and Conditions: a) i. tBuOK, DMSO, rt, 15 min; ii. Cl-R, rt, 1 h; b) i. 3, HCl, dioxane, 0° C., 1 h; ii. Boc-L-Leu-OH, HOBt, EDC, DIPEA, DMF, rt, overnight; c) i. 6, HCl, dioxane, 0° C.; ii. AcOH, HOBt, EDC, DIPEA, DMF, 0° C. to rt, overnight; d) 4 or 5, TFA, DCM, 0° C. to rt, 3.5 h or 2 h; Cl-R$_2$ for 18, 1 h, rt.
Scheme 2. Synthesis of Prodrugs 11, 12, 14, and 17.
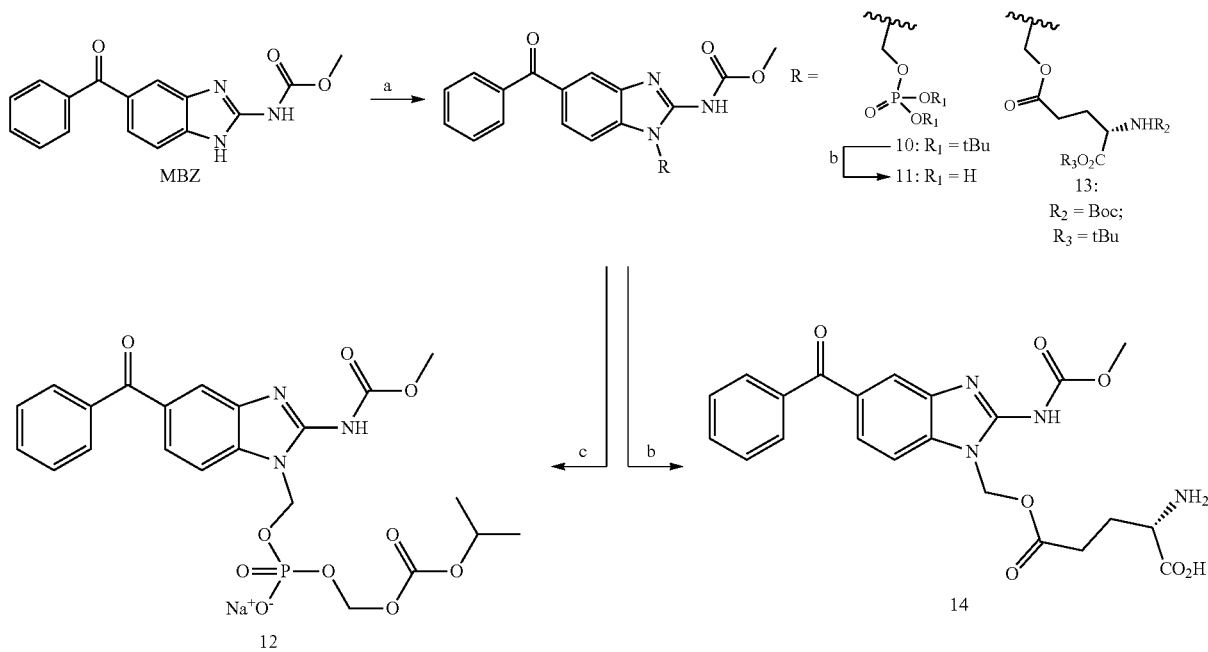

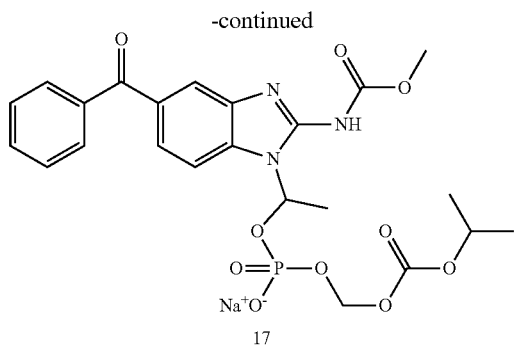

17

Reagents and Conditions: a) i. NaH, DMF, 0° C., 1 h; ii. Cl-R, DMF, 0° C. to rt, 16 h; b) 10 or 13, TFA, DCM, rt, 16 h; c) 12, N,N'-dicyclohexyl-4-morpholinecarboxamidine, DMF, chloromethyl isopropyl carbonate, rt, 24 h, 1 chloroethyl isopropyl carbonate for 17.

Example 3

Experimental

3.1 General Experimental

The $^1$H NMR spectra were measured at 400.1, or 500.1 MHz, $^{13}$C NMR spectra at 100.8, or 125.7 MHz (as specified in the individual compound characterization) in CDCl$_3$, CD$_3$COCD$_3$, CD$_3$SOCD$_3$, or CD$_3$OD as indicated in 5 mm PFG probe. For standardization of $^1$H NMR spectra the internal signal of TMS (δ 0.0, CDCl$_3$) or residual signals of solvents (δ 7.26 for CDCl$_3$, δ 2.05 for CD$_3$COCD$_3$, δ 2.50 for CD$_3$SOCD$_3$, and δ 3.31 for CD$_3$OD) were used. In the case of $^{13}$C NMR spectra the residual signals of solvents (δ 77.0 for CDCl$_3$, δ 29.8 and δ 206.3 for CD$_3$COCD$_3$, δ 39.5 for CD$_3$SOCD$_3$, and δ 49.0 for CD$_3$OD) were used. The chemical shifts are given in δ-scale, and the coupling constants J are given in Hz. Low and high resolution CI mass spectra were measured using an orthogonal acceleration time-of-flight (OA-TOF) mass spectrometer (GCT premier, Waters) at an ionizing voltage of 70 eV, the m/z values are given with their relative intensities (%). The spectra were recorded in positive mode and the source temperature was 150° C. Methane was present as a reagent gas in the CI source. For exact measurements, the spectra were internally calibrated using Heptacosa or 2,4,6-tris(trifluoromethyl)-1,3,5-triazine (Metri). The ESI mass spectra were recorded with a ZQ micromass mass spectrometer (Waters) equipped with an ESCi multi-mode ion source and controlled by MassLynx software. THF was freshly distilled from sodium/benzophenone under nitrogen. The flash chromatography was performed on Silica gel 60 (0.040-0.063 mm, Fluka). All chemicals were purchased from Sigma-Aldrich. Dichloromethane was freshly distilled from calcium hydride under nitrogen. YMC-Pack, ODS-AM column 250×20 mm, 5 μm was used for RP-HPLC purifications. Purity of all final compounds was assessed by RP-HPLC (UV detector, 210 nm), and found to be over 95% unless otherwise noted. MBZ was supplied from TCI Europe.

(5-Benzoyl-2-((methoxycarbonyl)amino)-1H-benzo[d]imidazol-1-yl)methyl pivalate (1)

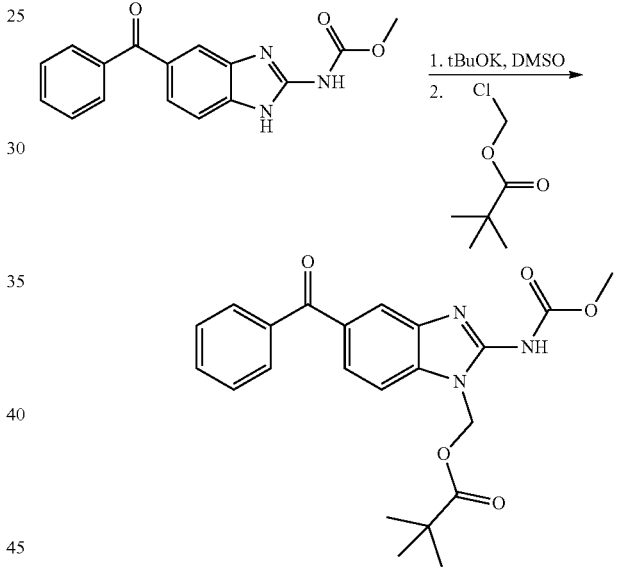

A suspension of MBZ (590 mg, 2.0 mmol, 1 equiv) and t-BuOK (495 mg, 4.4 mmol, 2.2 equiv) in anhydrous DMSO (10 mL) was sonicated until complete dissolution and then the solution was stirred for 15 min at rt. Chloromethyl pivalate (288 μL, 2.0 mmol, 1 equiv) was added, the solution was stirred for 1 h at rt and the solvent was evaporated (60° C.). The residue was chromatographed on a silica gel column (acetone/hexanes 2:3). The product 1 was finally crystallized from EtOAc/hexane mixture gave 410 mg of colorless solid (50% yield, mixture of N$^1$ and N$^3$ isomers). $^1$H NMR (500.1 MHz, DMSO-d$_6$): δ 1.11, 1.13 (2×s, 9H), 3.67, 3.68 (2×s, 3H), 6.11 (bs, 2H), 7.53-7.87 (m, 8H), 12.32 (bs, 1H). $^{13}$C NMR (125.7 MHz, DMSO-d$_6$): δ 26.6, 26.6, 38.3, 38.3, 52.0, 64.9 (bs), 109.6, 111.5, 125.1, 125.7, 128.4, 129.3, 129.4, 131.5, 132.0, 132.1, 132.2, 137.6, 137.7, 163.2, 176.7, 176.7, 194.8, 194.9. MS (ESI) m/z (%): 410 (100, [M+H]$^+$), 432 (44, [M+Na]$^+$), 841 (25, [2M+Na]$^+$). HRMS (ESI): [M+H] (C$_{22}$H$_{24}$O$_5$N$_3$) calcd. 410.17105, found 410.17120.

Methyl (5-benzoyl-1-(((isopropoxycarbonyl)oxy)methyl)-1H-benzo[d]imidazol-2-yl)carbamate (2)

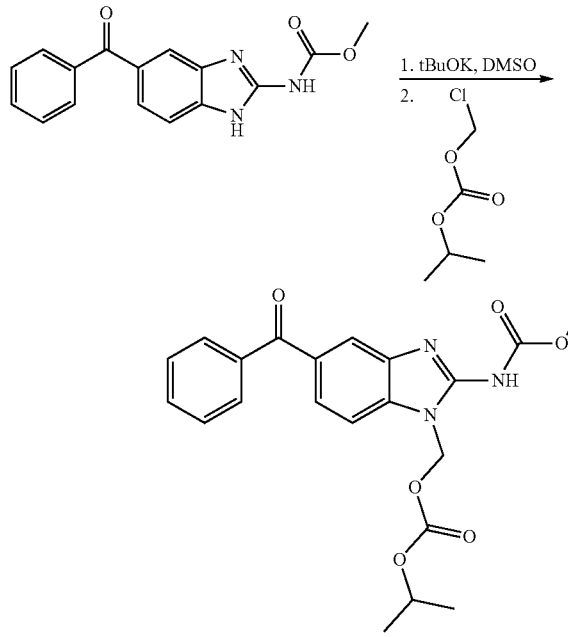

A suspension of MBZ (295 mg, 1.0 mmol, 1 equiv) and t-BuOK (123 mg, 1.1 mmol, 1.1 equiv) in anhydrous DMSO (5 mL) was sonicated until complete dissolution and then the solution was stirred for 15 min at rt. Chloromethyl isopropyl carbonate (268 μL, 2.0 mmol, 2 equiv) was added and the resulting solution was stirred for further 1 h at rt. Solvent was evaporated (60° C.) and the residue was chromatographed on a silica gel column (acetone/hexanes 2:3). The predominant product was purified again in the same way giving 180 mg of colorless solid (44% yield, mixture of $N^1$ and $N^3$ isomers). $^1$H NMR (500.1 MHz, DMSO-$d_6$): δ 1.20-1.23 (m, 6H), 3.65 and 3.66 (2×s, 3H), 4.75-4.84 (m, 1H), 6.10 (bs, 2H), 7.53-7.99 (m, 8H), 12.35 and 12.50 (2×bs, 1H). $^{13}$C NMR (125.7 MHz, DMSO-$d_6$): δ 21.5, 21.6, 52.3, 67.2, 67.4, 72.7, 72.7, 110.0, 111.4, 111.8, 113.5, 125.5, 126.4, 128.7, 129.7, 129.8, 131.7, 132.2, 132.5, 132.6, 137.7, 137.8, 153.2, 153.3, 154.5 (bs), 162.4 (bs), 195.0, 195.1. MS (ESI) m/z (%): 412 (100, [M+H]$^+$), 434 (32, [M+Na]$^+$), 845 (27, [2M+Na]+). HRMS (ESI): [M+H] ($C_{21}H_{22}O_6N_3$) calcd. 412.15031, found 412.15045.

(5-Benzoyl-2-((methoxycarbonyl)amino)-1H-benzo[d]imidazol-1-yl)methyl (tert-butoxycarbonyl)glycinate (3)

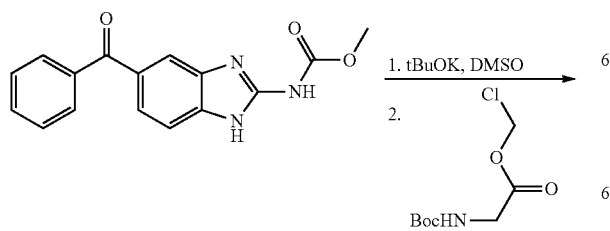

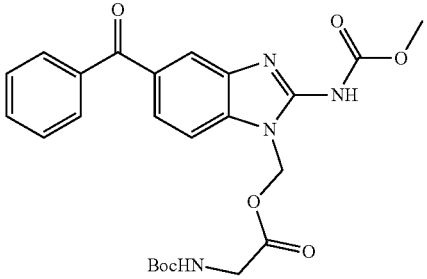

MBZ (832 mg, 2.82 mmol, 1 equiv) and t-BuOK (364 mg, 3.24 mmol, 1.15 equiv.) were suspended in anhydrous DMSO (10 mL) and the mixture was sonicated until complete dissolution occurred. Finally, chloromethyl (tert-butoxycarbonyl)glycinate (630 mg, 2.82 mmol, 1 equiv) in DMSO (5 mL) was added. The resulting solution was stirred for 1 h at rt and the solvent was evaporated (60° C.). The residue was chromatographed on a silica gel column (acetone/hexanes 2:3) giving 570 mg (42% yield) of product contaminated with MBZ. The product was used for the next step without further purification. MS (ESI) m/z (%): 483 (40, [M+H]$^+$), 505 (100, [M+Na]$^+$). HRMS (ESI): [M+H] ($C_{24}H_{27}O_7N_4$) calcd. 483.18743, found 483.18761; [M+Na] ($C_{24}H_{26}O_7N_4Na$) calcd. 505.16937, found 505.16942.

(5-Benzoyl-2-((methoxycarbonyl)amino)-1H-benzo[d]imidazol-1-yl)methyl tert-butyl succinate (4)

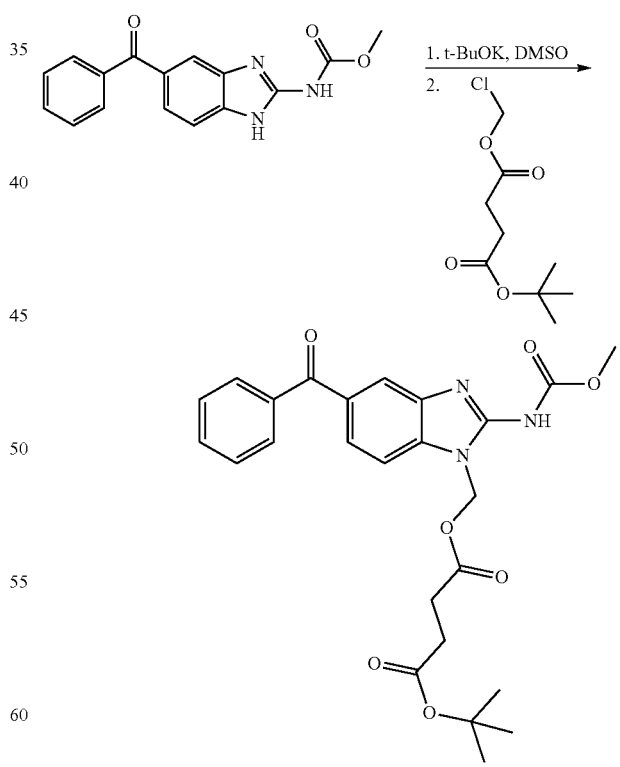

MBZ (2.07 g, 7.00 mmol, 1 equiv) and t-BuOK (903 mg, 8.05 mmol) were suspended in anhydrous DMSO (15 mL) and the suspension was sonicated until complete dissolution of both compounds. The resulting solution was stirred for 15 min at rt. Finally, a solution of tert-butyl (chloromethyl) succinate (1.56 g, 7.0 mmol, 1 equiv.) in DMSO (15 mL) was added dropwise and the mixture was stirred for 1 h at rt. Solvent was evaporated (60° C.). The residue was chromatographed repeatedly (2×) on a silica gel column (acetone/hexanes 2:3) giving 1.20 g (36% yield, mixture of $N^1$ and $N^3$ isomers) of amorphous solid. $^1$H NMR (500.1 MHz, CDCl$_3$): δ 1.37, 1.39 (2×s, 9H), 2.52-2.63 (m, 4H), 3.81, 3.82 (2×s, 3H), 6.13-6.18 (2×s, 2H), 7.30 (m, ½ H), 7.48-7.56 (m, 2½ H), 7.61 (m, 1H), 7.72-7.81 (m, 3½ H), 7.97 (d, ½ H, J=1.6), 11.29, 11.41 (2×bs, 1H). $^{13}$C NMR (125.7 MHz, CDCl$_3$): δ 27.9, 28.0, 28.9, 29.0, 29.9, 52.9, 52.9, 63.6, 63.8, 80.9, 80.9, 109.7, 109.9, 112.2, 112.3, 126.5, 126.8, 128.3, 129.9, 130.0, 132.4, 133.0, 133.3, 137.5, 137.6, 155.8, 164.3, 171.0-172.1 (m), 195.2, 195.4. MS (ESI) m/z (%): 482 (58, [M+H]$^+$), 504 (100, [M+Na]+). HRMS (ESI): [M+H] (C$_{25}$H$_{28}$O$_7$N$_3$) calcd. 482.19218, found 482.19222; [M+Na] (C$_{25}$H$_{27}$O$_7$N$_3$Na) calcd. 504.17412, found 504.17413.

Chloromethyl (((2R,3R,4S,5R,6R)-3,4,5,6-tetrakis ((trimethylsilyl)oxy)tetrahydro-2H-pyran-2-yl) methyl) carbonate

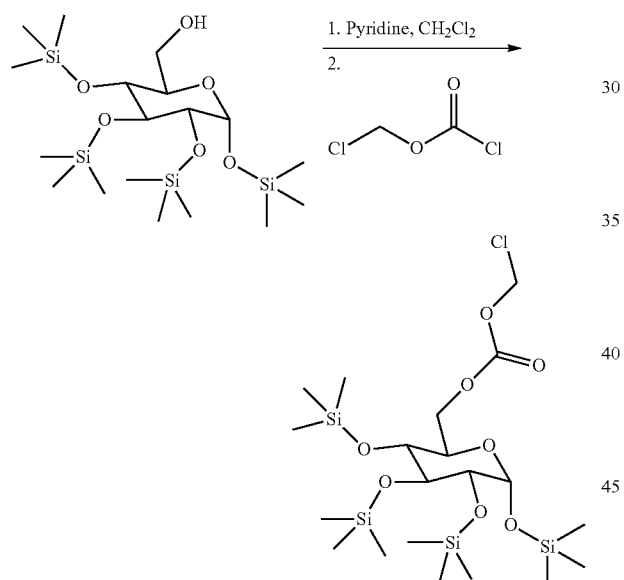

A solution of 1,2,3,4-tetra-OTMS-D-glucose (1.41 g, 3.0 mmol, 1 equiv) in anhydrous CH$_2$Cl$_2$ (15 mL) was cooled to 0° C., pyridine (290 μL, 3.6 mmol, 1.2 equiv) was added and finally chloromethyl chloroformate (293 μL, 3.3 mmol, 1.1 equiv) was added dropwise during 5 minutes. The resulting mixture was stirred for 1.5 h at rt, then quenched by addition of 5% aq. NH$_4$C$_1$ (20 mL). Aqueous phase was extracted with further CH$_2$Cl$_2$ (15 mL) and combined organic phases were dried over MgSO$_4$ and concentrated. The crude product was obtained as syrup yielded 1.64 g (97%) and it was used to the following step without further purification. $^1$H NMR (500.1 MHz, CDCl$_3$): δ 0.13 (s, 9H), 0.14 (2×s, 18H), 0.16 (s, 9H), 3.37 (dd, 1H, J=9.0, 3.0), 3.46 (dd, 1H, J=9.8, 8.6), 3.78 (t, 1H, J=8.9), 3.90-3.95 (m, 1H), 4.28 (dd, 1H, J=11.4, 4.5), 4.42 (dd, 1H, J=11.4, 2.3), 5.03 (d, 1H, J=3.0), 5.72 (d, 1H, J=6.3), 5.79 (d, 1H, 6.3). $^{13}$C NMR (125.7 MHz, CDCl$_3$): δ 0.3, 0.6, 1.0, 1.4, 68.1, 69.8, 72.0, 72.3, 73.8, 73.9, 94.1, 153.5. MS (ESI) m/z (%): 583 (100, [M+Na]$^+$), 585 (57, [M+Na]$^+$). HRMS (ESI): [M+Na] (C$_{20}$H$_{45}$O$_8$ClNaSi$_4$) calc. 583.17722, found 583.17738.

Methyl (5-benzoyl-1-(((((((2R,3R,4S,5R,6R)-3,4,5, 6-tetrakis((trimethylsilyl)oxy)tetrahydro-2H-pyran-2-yl)methoxy)carbonyl)oxy)methyl)-1H-benzo[d] imidazol-2-yl)carbamate (5)

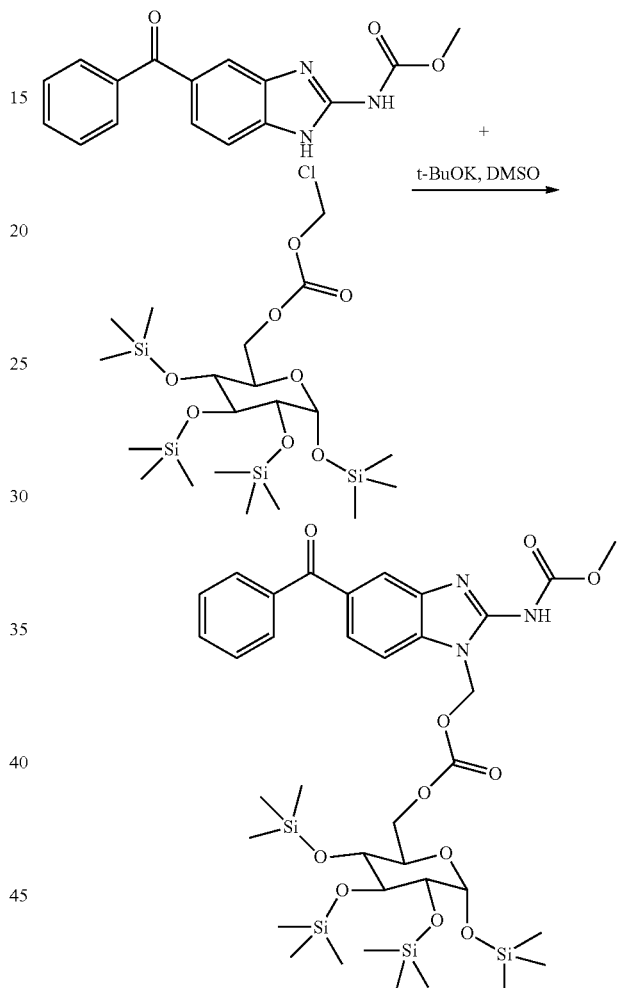

MBZ (703 mg, 2.38 mmol, 1 equiv) and t-BuOK (294 mg, 2.62 mmol, 1.1 equiv) were suspended in anhydrous DMSO (5 mL) and the mixture was sonicated until complete dissolution and then the solution was stirred for 15 min at rt. Then, a solution of chloromethyl (((2R,3R, 4S, 5R, 6R)-3, 4,5,6-tetrakis((trimethylsilyl)oxy)tetrahydro-2H-pyran-2-yl)methyl) carbonate (1.67 g, 2.97 mmol, 1.25 equiv) in DMSO (5 mL) was slowly added and the resulting solution was stirred for 1 h at rt. Solvent was evaporated (60° C.) and the residue was chromatographed on a silica gel column (acetone/hexanes 1:9 to 3:7). The desired compound was yielded 495 mg (25% yield, $N^1$ predominate positional isomer). $^1$H NMR (500.1 MHz, CDCl$_3$): δ 0.13-0.19 (4×s, 36H), 3.45 (dd, J=9.2, 3.0, 1H), 3.62 (t, J=9.1 Hz, 1H), 3.79-3.84 (m, 4H), 3.95-4.00 (m, 1H), 4.26 (dd, J=11.7, 4.5, 1H), 4.30-4.36 (m, 1H), 5.05 (d, J=3.0, 1H), 6.11-6.23 (m, 2H), 7.47-7.54 (m, 2H), 7.58-7.64 (m, 1H), 7.68-7.81 (m, 4H), 7.94-7.96 (m, 1H). $^{13}$C NMR (125.7 MHz, CDCl$_3$): δ 0.3, 0.6, 1.1, 1.4, 55.6, 65.2, 67.2, 70.2, 72.3, 74.0, 74.1, 94.1, 109.7, 112.1, 126.6, 127.2, 128.5, 130.1, 132.6, 133.1, 133.5, 137.8, 155.2, 154.9, 195.5. MS (ESI) m/z (%): 820 (38, [M+H]$^+$), 842 (100, [M+Na]+). HRMS (ESI): [M+H] (C$_{36}$H$_{58}$O$_{11}$N$_3$Si$_4$) calcd. 820.31429, found 820.31470; [M+Na] (C$_{36}$H$_{57}$O$_{11}$N$_3$NaSi$_4$) calcd. 842.29624, found 842.29653.

(5-Benzoyl-2-((methoxycarbonyl)amino)-1H-benzo[d]imidazol-1-yl)methyl (tert-butoxycarbonyl)-L-leucylglycinate (6)

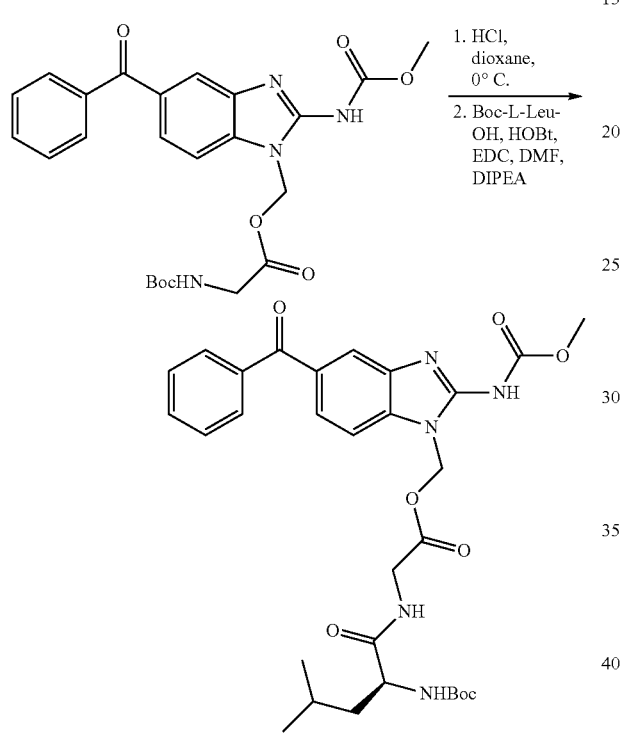

The crude compound 3 (907 mg, <1.88 mmol, 1 equiv) was treated with 2M HCl in dioxane (10 mL) at 0° C. and the solution was stirred for 1 h, solvent was evaporated and residue was codistilled with toluene (10 mL). The residue was dissolved in DMF (10 mL) and the solution was used immediately in subsequent reaction with Boc-L-Leu-OH. In the meantime a mixture of Boc-L-Leu-OH.H$_2$O (469 mg, 1.88 mmol, 1 equiv), HOBt (270 mg, 2.06 mmol, 1.1 equiv) and EDC.HCl (383 mg, 2.06 mmol, 1.1 equiv) in DMF (2 mL) was treated with DIPEA (675 µL, 3.88 mmol, 2.1 equiv) at 0° C. The mixture was stirred for 10 min at 0° C. and then a freshly prepared DMF solution of intermediate (5-benzoyl-2-((methoxycarbonyl)amino)-1H-benzo[d]imidazol-1-yl)methyl glycinate hydrochloride was added. The mixture was stirred at rt overnight, the solvent was evaporated and the residue was suspended in EtOAc (20 mL) using ultrasound. Crystals of MBZ were filtered off and the crude product was chromatographed on a silica gel column (MeOH/CHCl$_3$ 3:97). Yield 660 mg of syrup (59% yield, N$^1$ predominate positional isomer). $^1$H NMR (500.1 MHz, CDCl$_3$): δ 0.96 (m, 6H), 1.45 (s, 9H), 1.51-1.79 (m, 3H), 3.81 (s, 3H), 4.02-4.08 (m, 2H), 4.32 (m, 1H), 4.95 (bs, 1H), 6.17 (s, 2H), 6.83 (bs, 1H), 7.35 (d, 1H, J=8.3), 7.51 (m, 2H), 7.62 (m, 1H), 7.72 (m, 1H), 7.80 (m, 2H), 7.95 (d, 1H, J=1.5). $^{13}$C NMR (125.7 MHz, CD$_3$OD): δ 21.8, 22.9, 24.7, 28.3, 41.0, 41.6, 52.0, 53.0, 64.5, 79.9, 110.5, 111.8, 127.1, 128.4, 128.9, 130.0, 132.5, 133.0, 137.5, 155.2, 155.6, 155.8, 163.6, 169.1, 176.6, 195.3. MS (ESI) m/z (%): 596 (28, [M+H]$^+$), 618 [M+Na]$^+$. HRMS (ESI): [M+H] (C$_{30}$H$_{38}$O$_8$N$_5$) calcd. 596.27149, found 596.27153; [M+Na] (C$_{24}$H$_{37}$O$_8$N$_5$Na) calcd. 618.25343, found 618.25349.

(5-Benzoyl-2-((methoxycarbonyl)amino)-1H-benzo[d]imidazol-1-yl)methyl acetyl-L-leucylglycinate (7)

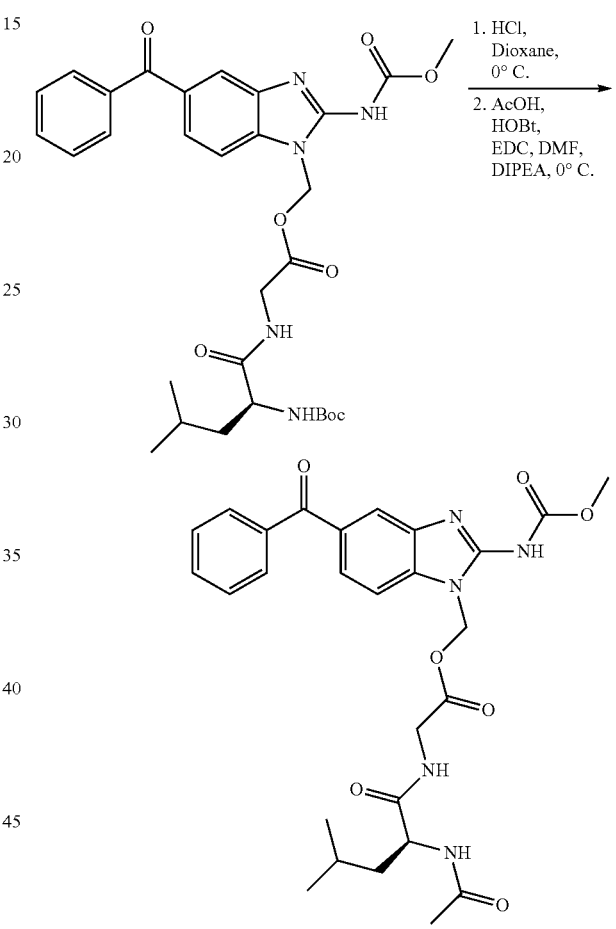

The crude compound 6 (623 mg, 1.05 mmol, 1 equiv.) was treated with 2M HCl in dioxane (10 mL) at 0° C. and the solution was stirred for 1 h at rt, then solvent was evaporated and the residue was codistilled with toluene (10 mL). The Boc-deprotected intermediate was dissolved in DMF (10 mL) and the solution was used immediately in subsequent reaction with AcOH. In the meantime a mixture of AcOH (54 µL, 1.05 mmol, 1 equiv), HOBt (149 mg, 1.10 mmol, 1.05 equiv) and EDC.HCl (211 mg, 1.10 mmol, 1.05 equiv) in DMF (1 mL) was treated with diisopropylethylamine (374 µL, 2.15 mmol, 2.05 equiv) at 0° C. The mixture was stirred for 10 min at 0° C. and then a freshly prepared DMF solution of (5-benzoyl-2-((methoxycarbonyl)amino)-1H-benzo[d]imidazol-1-yl)methyl L-leucylglycinate hydrochloride was added. The mixture was stirred at rt overnight, solvent was evaporated and the residue was suspended in EtOAc (20 mL) using sonication. Crystals of MBZ were filtered off and the crude product was chromatographed on a silica gel column MeOH:EtOAc (3:97 to 1:19); subsequent purification on 50 g C18 Aq column (20% to 75% ACN/H$_2$O) gave 62 mg (11% yield, N$^1$ predominant positional isomer). $^1$H NMR (500.1 MHz, CDCl$_3$): δ 0.87 (d, 3H, J=6.1), 0.89 (d, 3H, J=6.3), 1.43-1.66 (m, 3H), 1.99 (s, 3H), 3.79 (s, 3H), 3.95 (dd, 1H, J=18.2, 5.3), 4.06 (dd, 1H, J=18.2, 5.9), 4.53 (m, 1H), 6.12-6.17 (m, 2H), 6.53 (m, 1H), 7.11 (bs, 1H), 7.31 (d, 1H, J=8.2), 7.50 (m, 2H), 7.61 (m, 1H), 7.67 (dd, 1H, J=8.3, 1.4), 7.78 (m, 2H), 7.95 (d, 1H, J=1.5). $^{13}$C NMR (125.7 MHz, CDCl$_3$): δ 22.0, 22.8, 23.0, 24.6, 40.1, 41.2, 51.1, 52.9. 64.3, 109.5, 111.9, 127.1, 128.4, 128.9, 130.0, 132.5, 132.9, 137.4, 155.4, 163.8, 169.1, 170.8, 172.7, 195.5. MS (ESI) m/z (%): 538 (38, [M+H]$^+$), 560 [M+Na]$^+$. HRMS (ESI): [M+Na] (C$_{27}$H$_{31}$O$_7$N$_5$Na) calcd. 560.21157, found 560.21161.

4-((5-Benzoyl-2-((methoxycarbonyl)amino)-1H-benzo[d]imidazol-1-yl)methoxy)-4-oxobutanoic acid (8)

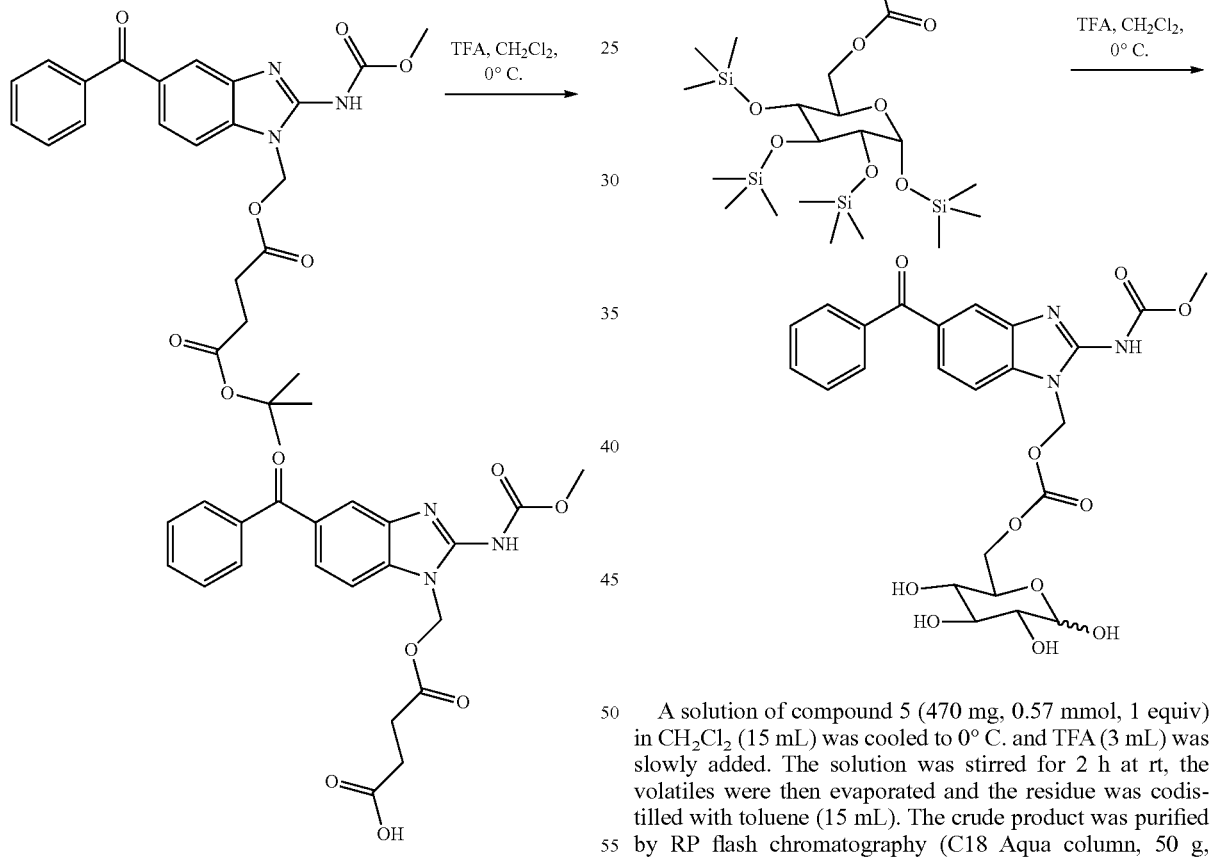

A suspension of compound 4 (1.15 g, 2.39 mmol, 1 equiv) in CH$_2$Cl$_2$ (30 mL) was cooled to 0° C. and then treated with TFA (10 mL). The resulting solution was stirred for 3.5 h at rt. The volatiles were distilled off and the residue was codistilled with toluene (30 mL). The product and MBZ as a major contaminant were separated by repeated RP flash chromatography (C18 Aqua column, 50 g, H$_2$O to 80% ACN/H$_2$O, 20 min). Yield 375 mg (37% yield, N$^1$ predominant positional isomer, 3:1 mixture) of solid compound. $^1$H NMR (500.1 MHz, CD$_3$COCD$_3$): δ 4.61-4.69 (m, 4H), 3.68 (s, 3H), 6.21 (s, 2H), 7.54-7.60 (m, 2H), 7.63-7.69 (m, 2H), 7.71-7.76 (m, 1H), 7.78-7.84 (m, 2H), 7.97 (dd, 1H, J=1.6, 0.6). $^{13}$C NMR (125.7 MHz, DMSO-d$_6$): δ 28.5 (bs), 52.1, 64.6, 109.8, 113.3, 125.4, 128.5, 129.5, 129.7, 131.3, 131.9, 132.4, 137.6, 154.3, 162.4, 171.8, 173.3, 195.0. MS (ESI) m/z (%): 424 (4, [M–H]$^+$), 849 (6, [2M–H]). HRMS (ESI): [M–H] (C$_{21}$H$_{18}$O$_7$N$_3$) calcd. 424.11502, found 424.11471.

Methyl (5-benzoyl-1-((((((2R,3S,4S,5R)-3,4,5,6-tetrahydroxytetrahydro-2H-pyran-2-yl)methoxy) carbonyl)oxy)methyl)-1H-benzo[d]imidazol-2-yl) carbamate (9)

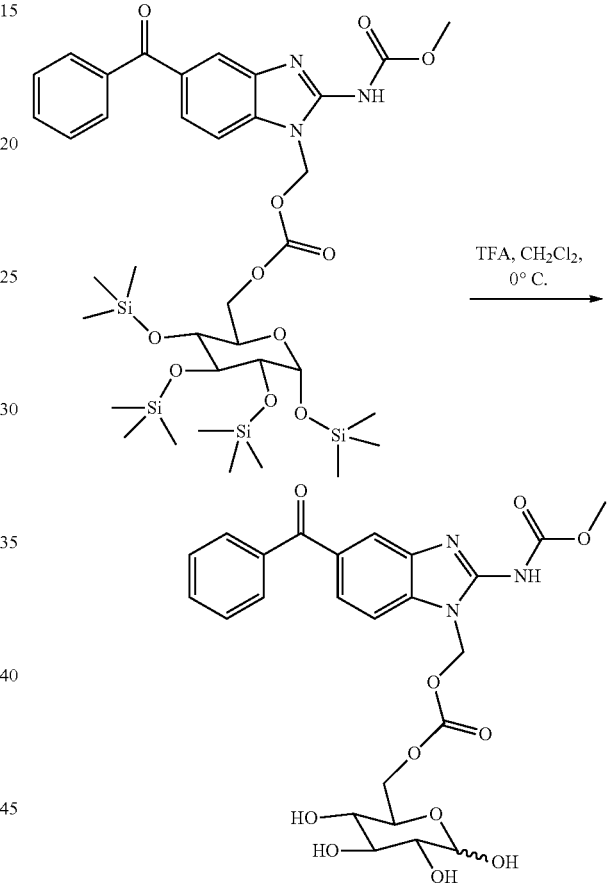

A solution of compound 5 (470 mg, 0.57 mmol, 1 equiv) in CH$_2$Cl$_2$ (15 mL) was cooled to 0° C. and TFA (3 mL) was slowly added. The solution was stirred for 2 h at rt, the volatiles were then evaporated and the residue was codistilled with toluene (15 mL). The crude product was purified by RP flash chromatography (C18 Aqua column, 50 g, H$_2$O→MeOH, 20 min) yield 188 mg. Recrystallization from EtOH/Et$_2$O afforded 122 mg of colorless solid (40% yield, mixture of N$^1$ and N$^3$ isomers). $^1$H NMR (500.1 MHz, MeOD-d$_4$): δ 3.14-3.20 (m, ½ H), 3.35-3.42 (m, 2H), 3.53-3.58 (m, ½ H), 3.71 (t, J=9.3, ½ H), 3.79, 3.80 (2×s, 3H), 4.00-4.07 (m, ½ H), 4.27-4.48 (m, 1½ H), 4.51 (dd, J=7.8, 1.9, 1H), 5.11 (d, J=3.7, ½ H), 6.16, 6.18 (2×bs, 2H), 7.51-7.57 (m, 2½ H), 7.61-7.68 (m, 1½ H), 7.69-7.86 (m, 3½ H). $^{13}$C NMR (125.7 MHz, DMSO-d$_6$) δ 55.2, 55.2, 64.9, 65.1, 67.4, 67.6, 69.4, 70.4, 72.3, 73.0, 73.8, 74.7, 76.6, 76.8, 92.3, 96.9, 109.9, 111.2, 111.7, 113.3, 125.4, 126.3, 128.5, 128.5, 129.5, 129.7, 131.5, 132.0, 132.4, 132.5, 137.5, 137.6, 154.2, 154.3, 154.3 (bs), 162.0 (bs), 194.9, 195.0. MS (ESI) m/z (%): 532 (5, [M+H]⁺), 554 (100, [M+Na]⁺), 1085 (6, [2M+Na]⁺). HRMS (ESI): [M+Na] (C$_{24}$H$_{25}$O$_{11}$N$_3$Na) calcd. 554.13813, found 554.13830.

Methyl (5-benzoyl-1-(((di-tert-butoxyphosphoryl)oxy)methyl)-1H-benzo[d]imidazol-2-yl)carbamate (10)

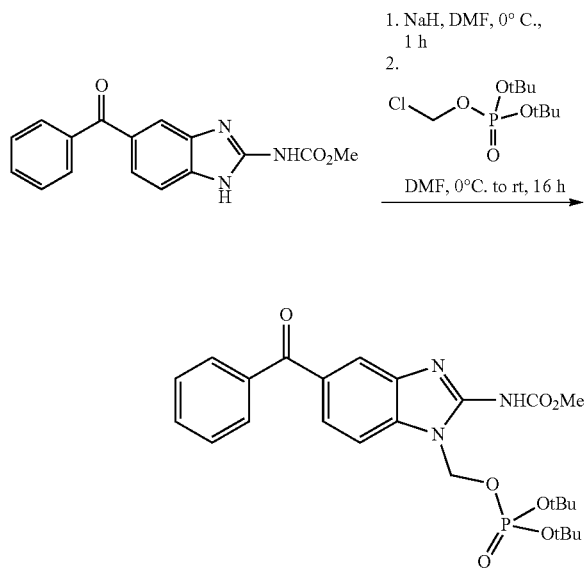

MBZ (2.00 g, 6.64 mmol, 1 equiv) and NaH (796 mg, 19.9 mmol, 3 equiv) were placed in a Schlenk flask and put under an argon atmosphere. DMF (40 mL) was slowly added while stirring. The mixture was stirred at rt for 1 h, during which time homogeneous yellow mixture formed. Di-tert-butyl (chloromethyl) phosphate (Flores-Ramos, et al., 2014) (2.06 g, 7.96 mmol, 1.2 equiv) in DMF (10 mL) was added dropwise during 2 min and the mixture was stirred overnight (16 h). Saturated aq. NaHCO$_3$ solution (100 mL) was added and the reaction mixture was extracted with EtOAc (4×180 mL), dried over MgSO$_4$, filtered and volatiles were evaporated. The residue was used without further purification to the following step.

Methyl (5-benzoyl-1-((phosphonooxy)methyl)-1H-benzo[d]imidazol-2-yl)carbamate (11)

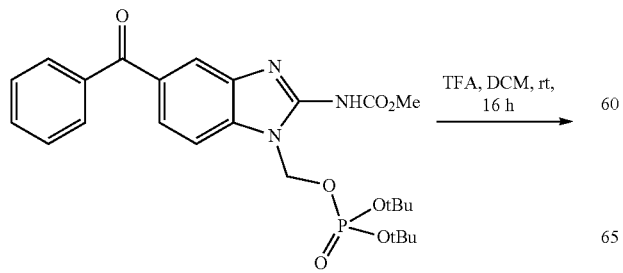

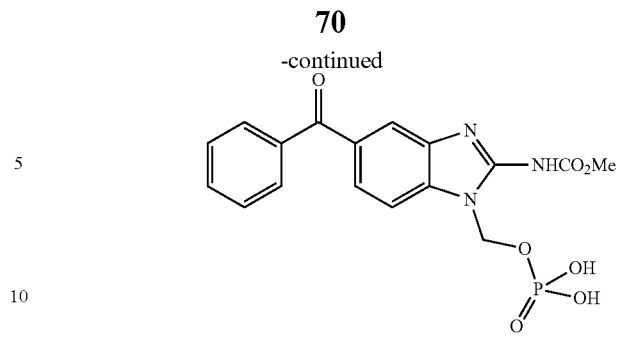

The crude compound 10, was placed in a Schlenk flask and put under an argon atmosphere. DCM (25 mL) was added followed by dropwise addition of trifluoroacetic acid (10 mL). The mixture was stirred at rt overnight (16 h). Volatiles were removed on rotavap and residue was purified on reverse phase C18 column (100 g, eluent H$_2$O+0.1% TFA to 70% MeCN, 20 min) to obtain 562 mg (21% yield, 1.39 mmol) of colorless solid after lyophilisation. ¹H NMR (400.1 MHz, DMSO-d$_6$): δ 3.67 (s), 3.68 (s, 3H), 5.85 (s), 5.87 (s, 2H), 7.54-7.71 (m, 5H), 7.72-7.78 (m, 2H), 7.85-7.97 (m, 1H). ¹³C NMR (100.8 MHz, DMSO-d$_6$): δ 52.2, 52.2, 66.3, 66.4, 109.9, 111.6, 111.9, 114.0, 125.2, 126.1, 128.5, 128.5, 129.3, 129.3, 129.5, 129.7, 131.4, 131.9, 132.4, 132.4, 132.6, 132.7, 137.4, 137.6, 153.2, 153.2, 161.1, 161.2, 194.9, 195.0. MS (ESI) m/z (%): 406 (100, [M+H]⁺). HRMS (ESI): [M+H] (C$_{17}$H$_{17}$O$_7$N$_3$P) calcd. 406.07986, found 406.07991.

Methyl (5-benzoyl-1-(((hydroxy(((isopropoxycarbonyl)oxy)methoxy)phosphoryl)oxy)methyl)-1H-benzo[d]imidazol-2-yl)carbamate, sodium salt (12)

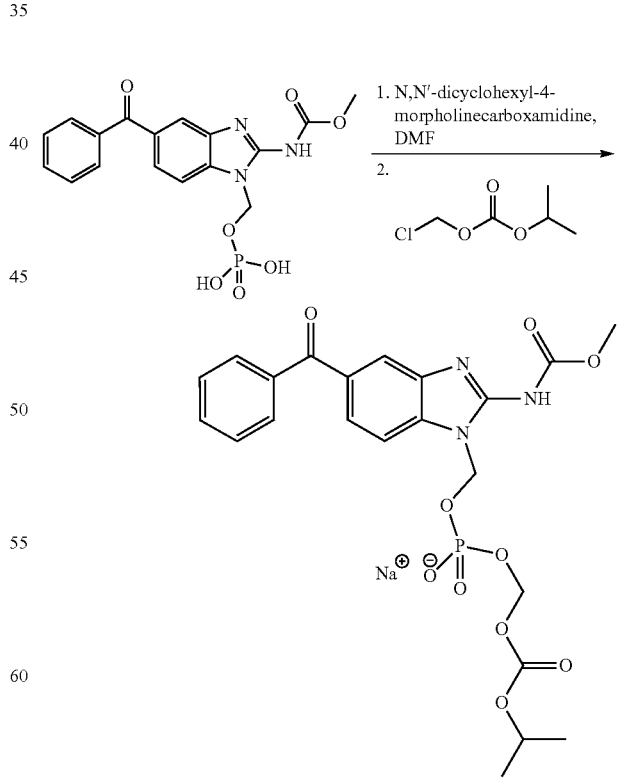

To a solution of compound 11 (600 mg, 1.48 mmol, 1 equiv) and N,N-dicyclohexyl-4-morpholinecarboxamidine (1.74 g, 5.92 mmol, 4 equiv) in anhydrous DMF (25 mL) chloromethyl isopropyl carbonate (1.3 mL, 8.88 mmol, 6 equiv) was added. The mixture was stirred for 24 h at rt. Solvent was evaporated and the residue was purified by RP flash chromatography (C18 Aqua column, 100 g, $H_2O$ to 70% $MeCN/H_2O$, 20 min) to yielded 536 mg of N,N-dicyclohexyl-4-morpholinecarboxamidine salt. The salt was put on a DOWEX 50×8 ($Na^+$) column and the product was eluted with 10% aq. methanol. UV absorbing fractions were concentrated and the product was precipitated by means of addition of several drops of EtOH, sonication and addition of excess of EtOAc. Yield 340 mg (42%, mixture of $N^1$ and $N^3$ isomers). $^1$H NMR (500.1 MHz, $CD_3OD$): δ 1.20, 1.24 (2×d, 6H, J=6.3), 3.78, 3.84 (2×bs, 3H), 4.72-4.83 (m, 1H), 5.42-5.49 (m, 2H), 5.88-5.94 (m, 2H), 7.53-7.56 (m, 2H), 7.62-7.67 (m, 1H), 7.77-7.82 (m, 2H), 7.47-8.08 (m, 3H). $^{13}$C NMR (125.7 MHz, $CD_3OD$): δ 21.9, 21.9, 53.5, 67.9, 68.8, 73.6, 86.8, 111.3, 113.6, 129.5, 129.5, 130.9, 131.1, 133.5, 133.9, 139.6, 154.9, 155.0, 197.8, 198.9. MS (ESI) m/z (%): 520 (72, [M−H]). HRMS (ESI): [M−H] ($C_{22}H_{23}O_{10}N_3P$) calcd. 520.11265, found 520.11230.

1-(tert-Butyl) 5-(chloromethyl) (tert-butoxycarbonyl)-L-glutamate

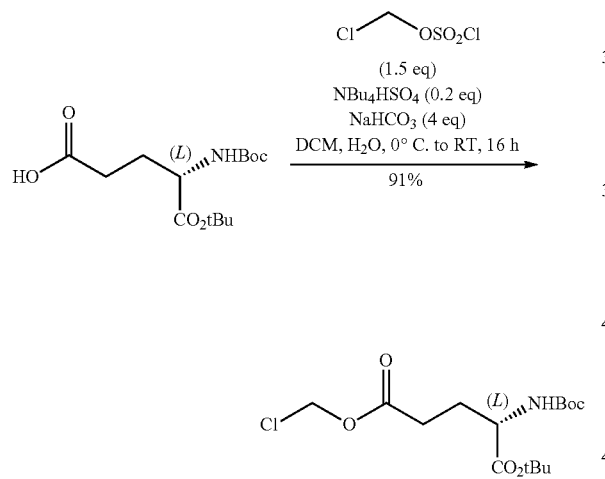

(S)-5-(tert-Butoxy)-4-((tert-butoxycarbonyl)amino)-5-oxopentanoic acid (2.00 g, 6.46 mmol, 1 equiv) was placed in a round-bottom flask and water (80 mL) was added followed by $Bu_4NHSO_4$ (448 mg, 1.29 mmol, 0.2 equiv) and portion wise addition of $NaHCO_3$ (2.19 g, 25.8 mmol, 4 equiv). The mixture was stirred for 15 min at rt, cooled to 0° C. and dichloromethane (80 mL) was added followed by dropwise (5 min) addition of chloromethyl chlorosulfate (989 µL, 9.69 mmol, 1.5 equiv). The mixture was warmed to rt and stirred overnight (16 h). The layers were separated, the aqueous one was washed once with dichloromethane (80 mL) and combined organic layers were dried with $MgSO_4$, filtered and after volatiles removal the oily residue was purified by column chromatography on silica (hexanes/EtOAc 7:3) affording 2.07 g (91%, 5.88 mmol) of yellowish oil. $^1$H NMR (400.1 MHz, $CDCl_3$): δ 1.43 (s, 9H), 1.46 (s, 9H), 1.86-1.98 (m, 1H), 2.11-2.25 (m, 1H), 2.37-2.56 (m, 2H), 3.96-4.35 (m, 1H), 4.71-5.25 (m, 1H), 5.65-5.73 (m, 2H); $^{13}$C NMR (100.8 MHz, $CDCl_3$): δ 27.9, 28.1, 28.4, 30.3, 53.3, 68.8, 80.0, 82.6, 155.5, 171.1, 171.2. MS (ESI) m/z (%): 374 (100, [M+Na]$^+$); HRMS (ESI): [M+Na] ($C_{15}H_{26}O_6NClNa$) calcd. 374.13409, found 374.13419.

5-((5-Benzoyl-2-((methoxycarbonyl)amino)-1H-benzo[d]imidazol-1-yl)methyl) 1-(tert-butyl) (tert-butoxycarbonyl)-L-glutamate (13)

MBZ (1.00 g, 3.32 mmol, 1 equiv) and NaH (146 mg, 3.65 mmol, 1.1 equiv) were placed in a Schlenk flask and put under an argon atmosphere. The flask was cooled to 0° C. and DMF (30 mL) was added while stirring. The mixture was stirred for 1 h at rt, during which time homogeneous yellow mixture was formed. 1-(tert-Butyl) 5-(chloromethyl) (tert-butoxycarbonyl)-L-glutamate (1.40 g, 3.98 mmol, 1.2 equiv) in DMF (10 mL) was added dropwise over 2 min. The resulting mixture was let warm up to rt and stirred overnight (16 h). After DMF removal, water (100 mL) was added and the mixture was extracted with EtOAc (3×150 mL) and combined organic layers were dried with $MgSO_4$, filtered and volatiles were removed using rotary evaporation. The resulting mixture was sonicated in $CHCl_3$ (10 mL), crystals were filtered off and washed with additional $CHCl_3$ (10 mL). Solvent was evaporated and the residue was purified on HPLC giving 648 mg (32% yield, 1.06 mmol) of a white solid. $^1$H NMR (400.1 MHz, $CDCl_3$): δ 1.37, 1.39 (s, 9H), 1.43, 1.44 (s, 9H), 1.74-2.01 (m, 1H), 2.06-2.23 (m, 1H), 2.35-2.54 (m, 2H), 3.83, 3.83 (s, 3H), 3.97-4.26 (m, 1H), 6.17 (d, J=4.9, 1H), 6.21 (s, 1H), 7.41-7.65 (m, 4H), 7.73-8.03 (m, 4H). $^{13}$C NMR (100.8 MHz, $CDCl_3$): δ 28.0, 28.0, 28.1, 28.1, 28.4, 28.4, 29.9, 29.9, 53.1, 53.1, 53.3, 53.4, 64.2, 64.4, 80.0, 80.1, 82.6, 82.6, 110.0, 111.2, 112.5, 113.5, 126.8, 127.2, 128.5, 128.5, 129.0, 129.3, 130.0, 130.2, 132.3, 132.5, 132.7, 132.7, 133.4, 133.8, 137.6, 137.6, 154.3, 154.6, 162.3, 162.3, 162.8, 162.8, 171.3, 171.3, 172.2, 172.4, 195.4, 195.5. MS (ESI) m/z (%): 633 (100, [M+Na]$^+$). HRMS (ESI): [M+Na] ($C_{31}H_{38}O_9N_4Na$) calcd. 633.25310, found 633.25321.

(S)-2-Amino-5-((5-benzoyl-2-((methoxycarbonyl)amino)-1H-benzo[d]imidazol-1-yl)methoxy)-5-oxopentanoic acid (14)

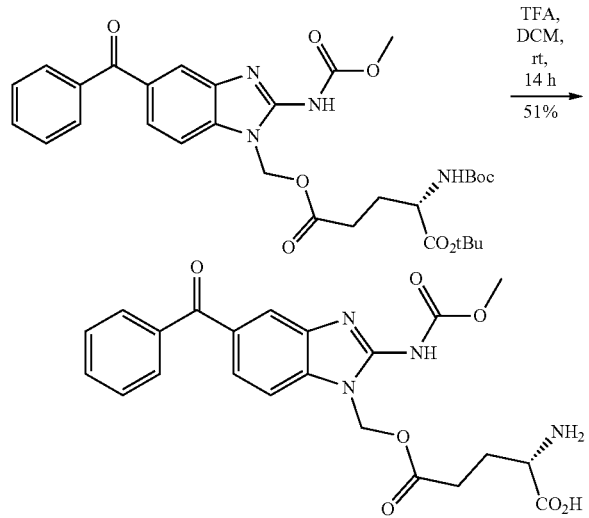

A mixture of 5-((5-benzoyl-2-((methoxycarbonyl)amino)-1H-benzo[d]imidazol-1-yl)methyl) 1-(tert-butyl) (tert-butoxycarbonyl)-L-glutamate and 5-((6-benzoyl-2-((methoxycarbonyl)amino)-1H-benzo[d]imidazol-1-yl)methyl) 1-(tert-butyl) (tert-butoxycarbonyl)-L-glutamate (106 mg, 0.17 mmol, 1 equiv) was placed in a Schlenk flask and put under an argon atmosphere. Dichloromethane (5 mL) was added followed by dropwise addition of trifluoroacetic acid (1 mL). The mixture was stirred at rt overnight (16 h). Volatiles were removed on rotavap and trifluoroacetic acid residue was removed by addition of toluene (3×5 mL) and its rotavap removal. The residual MBZ trifluoroacetate, which is soluble in CHCl₃, was removed by sonicating the mixture in CHCl₃ (2×5 mL), centrifugation and the supernatant removal. Acetonitrile (1 mL) and Et₂O (2 mL) were then added and the mixture was sonicated shortly causing a precipitate formation. After centrifugation, supernatant removal and final washing with CHCl₃ (5 mL) a white solid was obtained. The HPLC purity was 94% (50 mg, 0.09 mmol, 51% yield). The NMR spectra could not be obtained due to instability of the product in solution. MS (ESI) m/z (%): 455 (100, [M+H]$^+$). HRMS (ESI): [M+H] ($C_{22}H_{23}O_7N_4$) calcd. 455.15613, found 455.15623.

1-(5-benzoyl-2-((methoxycarbonyl)amino)-1H-benzo[d]imidazol-1-yl)ethyl pivalate (15)

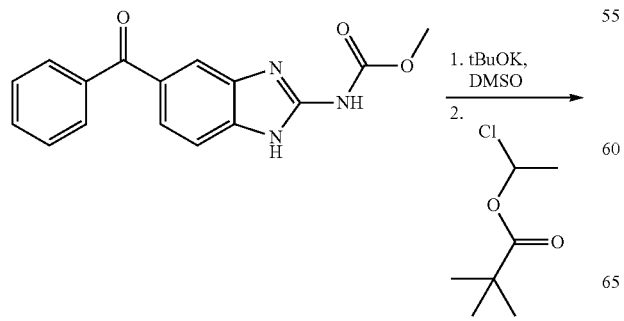

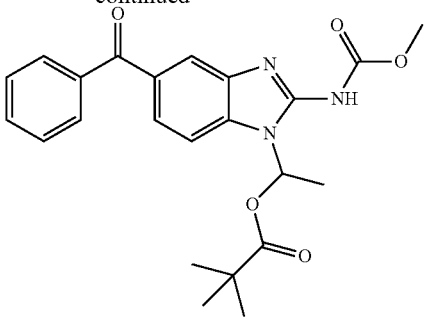

A suspension of MBZ (383 mg, 1.3 mmol) and t-BuOK (191 mg, 1.7 mmol) in anhydrous DMSO (5 mL) was sonicated until complete dissolution and then the solution was stirred 15 min at RT. 1-Chloroethyl pivalate (280 mg, 1.7 mmol) was added, the solution was stirred 1 h at RT and the solvent was then evaporated (70° C.). The residue was chromatographed on a silica gel column in 40% acetone/hexanes. Subsequent RP flash chromatography on a 50 g HP C18 Aq column (gradient H₂O→MeCN in 20 min, 40 mL/min) gave 133 mg (24%) of solid.

$^1$H NMR (401 MHz, CDCl₃): δ 1.16, 1.18 (2×s, 9H), 1.80, 1.82 (d, J=6.4 Hz, 3H), 3.78 (s, 3H), 7.19-7.29 (m, 1H), 7.47-7.81 (m, 7½ H), 8.02-8.04 (m, ½ H). $^{13}$C NMR (101 MHz, CDCl₃): δ 18.93, 18.96, 27.08, 27.10, 38.95, 38.99, 52.98, 75.07, 75.17, 110.86, 113.32, 125.86, 126.61, 128.46, 129.91, 129.98, 132.44, 132.51, 132.56, 132.73, 137.81, 137.92, 176.23, 176.37, 195.58, 195.59.

(Mixture of Position Isomers)

MS (ESI) m/z (%): 424 (100, [M+H]$^+$), 446 (66, [M+Na]$^+$), 869 (40, [2M+Na]+)

HRMS (ESI): [M+H] ($C_{23}H_{26}O_5N_3$) calc. 424.18670, found 424.18682

1-(5-benzoyl-2-((methoxycarbonyl)amino)-1H-benzo[d]imidazol-1-yl)-2-methylpropyl pivalate (16)

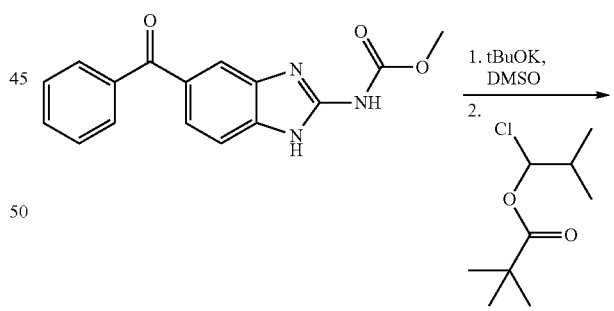

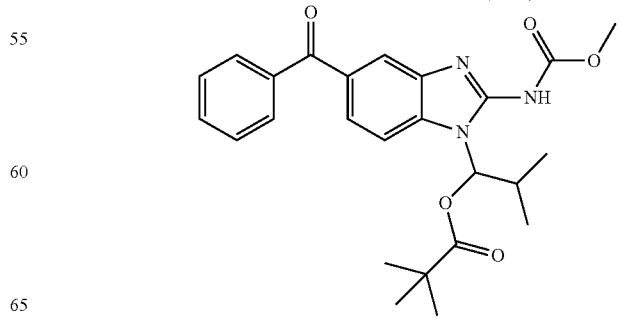

A suspension of MBZ (383 mg, 1.3 mmol) and t-BuOK (191 mg, 1.7 mmol) in anhydrous DMSO (5 mL) was sonicated until complete dissolution and then the solution was stirred 15 min at RT. 1-Chloro-2-methylpropyl pivalate (328 mg, 1.7 mmol) was added, the solution was stirred 1 h at RT and the solvent was then evaporated (70° C.). The residue was chromatographed on a silica gel column in 40% acetone/hexanes. Subsequent RP flash chromatography on a 50 g HP C18 Aq column (gradient $H_2O$ to MeCN in 20 min, 40 mL/min) gave 77 mg (13%) of solid.

$^1$H NMR (401 MHz, $CDCl_3$): δ 0.88 (t, J=6.9, 3H), 1.13-1.20 (m, 12H), 2.66-2.78 (m, 1H), 3.78 (2×s, 3H), 6.75, 6.78 (2×d, J=6.3, 1H), 7.47-7.81 (m, 7½ H), 7.98-8.01 (m, ½ H).

$^{13}$C NMR (101 MHz, $CDCl_3$): δ 17.74, 18.52, 27.11, 27.12, 31.40, 31.44, 39.14, 39.17, 53.00, 81.98, 82.05, 109.93, 111.06, 112.82, 113.43, 125.75, 126.66, 128.45, 129.94, 130.00, 132.44, 132.50, 132.68, 137.81, 137.92, 155.47, 155.57, 164.62, 176.30, 176.46, 195.56.

Mixture of $N^1$ and $N^3$ isomers

MS (ESI) m/z (%): 452 (66, [M+H]$^+$), 474 (100, [M+Na]$^+$)

HRMS (ESI): [M+H] ($C_{25}H_{30}O_5N_3$) calc. 452.21800, found 452.21803

Methyl (5-benzoyl-1-(((hydroxy(((isopropoxycarbonyl)oxy)ethoxy)phosphoryl)oxy) methyl)-1H-benzo[d]imidazol-2-yl)carbamate, sodium salt (17)

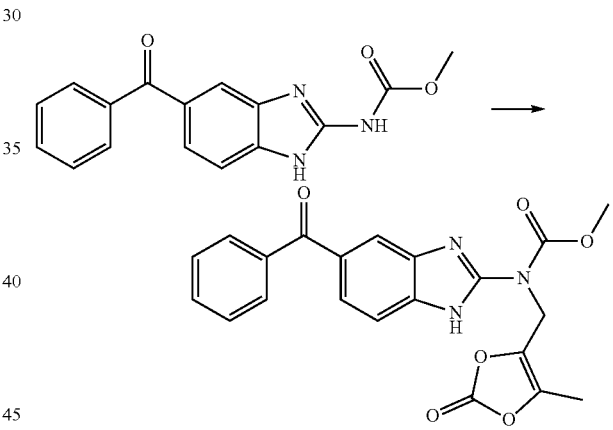

To a solution of methyl (5-benzoyl-1-((phosphonooxy) methyl)-1H-benzo[d]imidazol-2-yl)carbamate (17, 320 mg, 0.79 mmol) and N,N'-dicyclohexyl-4-morpholinecarboxamidine (1.16 g, 3.95 mmol) in DMF (15 mL) 1-chloroethyl isopropyl carbonate (960 mL, 6.32 mmol) was added. The mixture was stirred 5 days at RT. Then, the solvent was evaporated and the residue was purified by RP flash chromatography (C18 Aqua column, 50 g, $H_2O$ to 85% MeOH/ $H_2O$, 20 min, 40 mL/min), yield 155 mg of N,N-dicyclohexyl-4-morpholinecarboxamidine salt. The salt was put on a DOWEX 50WX8-400 (Na$^r$) column and the product was eluted with 20% aqueous methanol. UV adsorbing fractions were concentrated and the product was precipitated by means of addition of several drops of EtOH, sonication and addition of excess of EtOAc. Yield 72 mg (13%). Mixture of and $N^3$ isomers.

$^1$H NMR (401 MHz, $CD_3CO_2D$): δ 1.16-1.24 (m, 6H), 1.43, 1.46 (2×d, 3H, J=5.3), 3.91 (2×bs, 3H), 4.71, 4.72 (2×sept, J=6.2, 1H), 6.14, 6.17 (2×d, J=8.5, 2H), 6.28-6.38 (m, 1H), 7.52-7.59 (m, 2H), 7.64-7.70 (m, 1H), 7.77-7.95 (m, 4H), 8.13 (d, J=0.9, ½ H), 8.20 (d, J=0.9, ½ H).

$^{13}$C NMR (101 MHz, $CD_3CO_2D$): δ 22.32, 22.38, 22.43 (d), 22.52 (d), 55.40, 55.44, 69.58 (d), 69.70 (d), 74.16, 95.86 (d), 95.90 (d), 112.64, 114.81, 114.97, 117.08, 129.12, 129.29, 130.14, 130.19, 130.69, 130.92, 131.79, 131.87, 134.01, 134.58, 136.05, 136.33, 138.89, 138.92, 150.65, 150.85, 154.92, 154.95, 157.90, 158.06, 197.61, 197.62

MS (ESI) m/z (%): 534 (44, [M−H]).

HRMS (ESI): [M−H] ($C_{23}H_{25}O_{10}N_3P$) calc. 534.12830, found 534.12787.

Methyl (5-benzoyl-1H-benzo[d]imidazol-2-yl)((5-methyl-2-oxo-1,3-dioxol-4-yl)methyl)carbamate (18)

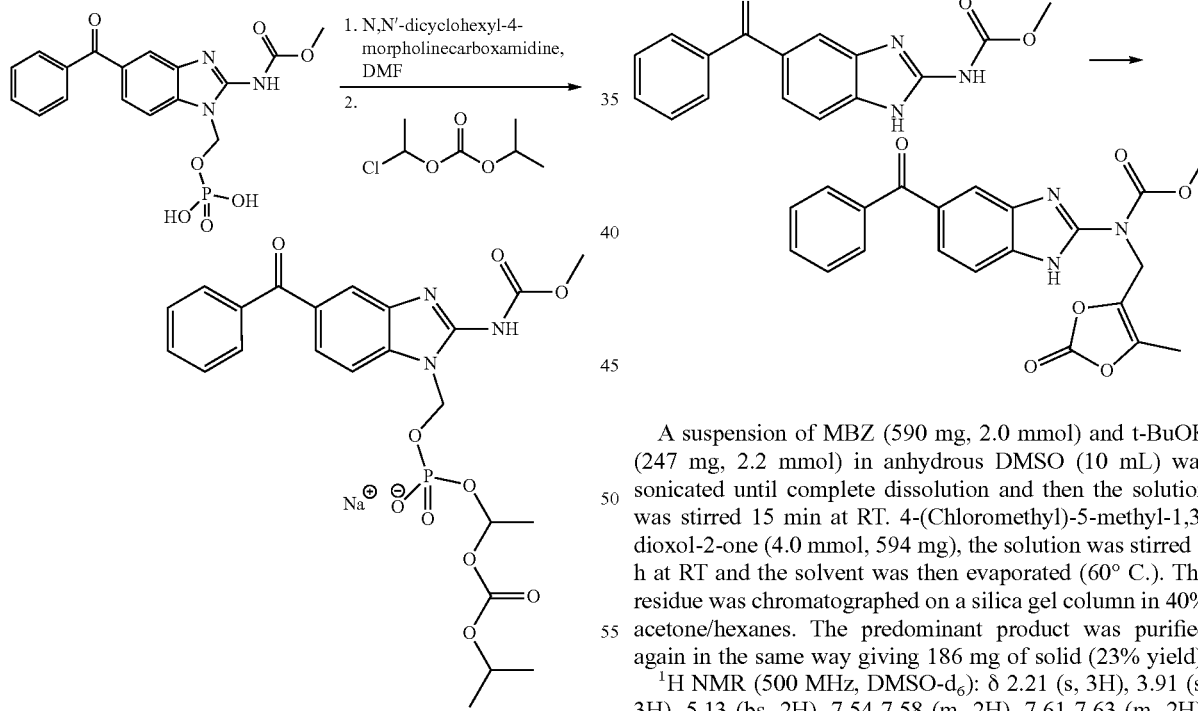

A suspension of MBZ (590 mg, 2.0 mmol) and t-BuOK (247 mg, 2.2 mmol) in anhydrous DMSO (10 mL) was sonicated until complete dissolution and then the solution was stirred 15 min at RT. 4-(Chloromethyl)-5-methyl-1,3-dioxol-2-one (4.0 mmol, 594 mg), the solution was stirred 1 h at RT and the solvent was then evaporated (60° C.). The residue was chromatographed on a silica gel column in 40% acetone/hexanes. The predominant product was purified again in the same way giving 186 mg of solid (23% yield).

$^1$H NMR (500 MHz, DMSO-$d_6$): δ 2.21 (s, 3H), 3.91 (s, 3H), 5.13 (bs, 2H), 7.54-7.58 (m, 2H), 7.61-7.63 (m, 2H), 7.66 (m, 1H), 7.71-7.74 (m, 2H), 7.79-7.97 (bm, 1H), 12.33 and 12.43 (2×bs, 1H).

$^{13}$C NMR (126 MHz, DMSO-$d_6$): δ 9.27, 54.48, 111.62, 114.74, 117.13, 119.92, 124.00, 128.57, 129.55, 132.12, 133.95, 138.46, 139.14, 150.14, 152.27, 153.53, 195.73\

MS (ESI) m/z (%): 408 (29, [M+H]$^+$), 430 (100, [M+Na]$^+$), 837 (20, [2M+Na]$^+$)

HRMS (ESI): [M+H] ($C_{21}H_{18}O_6N_3$) calc. 408.11901, found 408.11922.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

A Phase I Study of Mebendazole for the Treatment of Pediatric Gliomas. https://ClinicalTrials.gov/show/NCT01837862

Bai, R. Y.; Staedtke, V.; Rudin, C. M.; Bunz, F.; Riggins, G. J. Effective treatment of diverse medulloblastoma models with mebendazole and its impact on tumor angiogenesis. Neuro-Oncology 2015, 17, 545-54.

Bai, R. Y.; Staedtke, V.; Wanjiku, T.; Rudek, M. A.; Joshi, A.; Gallia, G. L.; Riggins, G. J. Brain Penetration and Efficacy of Different Mebendazole Polymorphs in a Mouse Brain Tumor Model. Clin Cancer Res 2015, 21, 3462-70.

Bai, R.-Y.; Staedtke, V.; Aprhys, C. M.; Gallia, G. L.; Riggins, G. J. Antiparasitic mebendazole shows survival benefit in 2 preclinical models of glioblastoma multiforme. Neuro-Oncology 2011, 13, 974-982.

Beaumont, K.; Webster, R.; Gardner, I.; Dack, K. Design of ester prodrugs to enhance oral absorption of poorly permeable compounds: challenges to the discovery scientist. Curr Drug Metab 2003, 4, 461-85.

Brits, M.; Liebenberg, W.; de Villiers, M. M. Characterization of polymorph transformations that decrease the stability of tablets containing the WHO essential drug mebendazole. J Pharm Sci 2010, 99, 1138-1151.

Carlert, S.; Akesson, P.; Jerndal, G.; Lindfors, L.; Lennernas, H.; Abrahamsson, B. In Vivo Dog Intestinal Precipitation of Mebendazole: A Basic BCS Class II Drug. Mol Pharm 2012, 9, 2903-2911.

Chanteux, H.; Van Bambeke, F.; Mingeot-Leclercq, M.-P.; Tulkens, P. M. Accumulation and oriented transport of ampicillin in Caco-2 cells from its pivaloyloxymethylester prodrug, pivampicillin. Antimicrobial agents and chemotherapy 2005, 49, 1279-1288.

Charoenlarp, P.; Waikagul, J.; Muennoo, C.; Srinophakun, S.; Kitayaporn, D. Efficacy of single-dose mebendazole, polymorphic forms A and C, in the treatment of hookworm and Trichuris infections. Southeast Asian J Trop Med Public Health 1993, 24, 712-6.

Chassaing, C.; Berger, M.; Heckeroth, A.; Ilg, T.; Jaeger, M.; Kern, C.; Schmid, K.; Uphoff, M. Highly water-soluble prodrugs of anthelmintic benzimidazole carbamates: synthesis, pharmacodynamics, and pharmacokinetics. J Med Chem 2008, 51, 1111-4.

Chiba, Y.; Kohri, N.; Iseki, K.; Miyazaki, K. Improvement of Dissolution and Bioavailability for Mebendazole, an Agent for Human Echinococcosis, by Preparing Solid Dispersion with Polyethylene Glycol. Chem Pharm Bull (Tokyo) 1991, 39, 2158-2160.

Dando, T.; Plosker, G. Adefovir dipivoxil: a review of its use in chronic hepatitis B. Drugs 2003, 63, 2215-34.

Daniel-Mwuambete, K.; Ponce-Gordo, F.; Torrado, J.; Torrado, S.; Cuesta-Bandera, C. Effect of two formulations of benzimidazole carbamates on the viability of cysts of Echinococcus granulosus in vivo. Parasite 2003, 10, 371-3.

Dawson, M.; Allan, R. J.; Watson, T. R. The pharmacokinetics and bioavailability of mebendazole in man: a pilot study using [3H]-mebendazole. Br J Clin Pharmacol 1982, 14, 453-5.

Dawson, M.; Braithwaite, P. A.; Roberts, M. S.; Watson, T. R. The pharmacokinetics and bioavailability of a tracer dose of [3H]-mebendazole in man. Br J Clin Pharmacol 1985, 19, 79-86.

Dawson, M.; Watson, T. R. 4-Amino-3-(3'-methoxycarbonyl-2'-thioureido)benzophenone, a prodrug of mebendazole. Eur J Drug Metab Pharmacokinet 1983, 8, 329-34.

Dawson, M.; Watson, T. R. The effect of dose form on the bioavailability of mebendazole in man. Br J Clin Pharmacol 1985, 19, 87-90.

Dayan, A. D. Albendazole, mebendazole and praziquantel. Review of non-clinical toxicity and pharmacokinetics. Acta Trop 2003, 86, 141-159.

de Paula, K.; Cami, G. E.; Brusau, E. V.; Narda, G. E.; Ellena, J. Mebendazole Mesylate Monohydrate: A New Route to Improve the Solubility of Mebendazole Polymorphs. J Pharm Sci 2013, 102, 3528-3538.

De Witt, M.; Gamble, A.; Hanson, D.; Markowitz, D.; Powell, C.; Al Dimassi, S.; Atlas, M.; Boockvar, J.; Ruggieri, R.; Symons, M. Repurposing Mebendazole as a Replacement for Vincristine for the Treatment of Brain Tumors. Mol Med 2017, 23, 50-56.

DeGoey, D. A.; Grampovnik, D. J.; Flosi, W. J.; Marsh, K. C.; Wang, X. C.; Klein, L. L.; McDaniel, K. F.; Liu, Y.; Long, M. A.; Kati, W. M.; Molla, A.; Kempf, D. J. Water-soluble prodrugs of the human immunodeficiency virus protease inhibitors lopinavir and ritonavir. J Med Chem 2009, 52, 2964-70.

Doudican, N.; Rodriguez, A.; Osman, I.; Orlow, S. J. Mebendazole Induces Apoptosis via Bcl-2 Inactivation in Chemoresistant Melanoma Cells. Mol Cancer Res 2008, 6, 1308-1315.

Fan, W.; Wu, Y.; Li, X. K.; Yao, N.; Li, X.; Yu, Y. G.; Hai, L. Design, synthesis and biological evaluation of brain-specific glucosyl thiamine disulfide prodrugs of naproxen. Eur J Med Chem 2011, 46, 3651-61.

Flores-Ramos, M.; Ibarra-Velarde, F.; Hernandez-Campos, A.; Vera-Montenegro, Y.; Jung-Cook, H.; Canto-Alarcon, G. J.; del Rivero, L. M.; Castillo, R. A highly water soluble benzimidazole derivative useful for the treatment of fasciolosis. Bioorg Med Chem Lett 2014, 24, 5814-5817.

Himmelreich, M.; Rawson, B. J.; Watson, T. R. Polymorphic Forms of Mebendazole. Australian J of Pharm Sci 1971, 6, 123-125.

Honorato, S. B.; Farfan, S.; Viana, A.; Filho, J. M.; CamarÃ£o, G. C.; Fechine, F. V.; Moraes, M. E. A.; Moraes, M. O.; Ferro, M.; Dabbene, V.; Cuffini, S. L.; Ayala, A. P. Polymorphism evaluation in generic tablets containing mebendazole by dissolution tests. J Braz Chem Soc 2012, 23, 220-227.

Kearney, B. P.; Flaherty, J. F.; Shah, J. Tenofovir disoproxil fumarate. Clinical pharmacokinetics 2004, 43, 595-612.

Klepser, M. E.; Marangos, M. N.; Patel, K. B.; Nicolau, D. P.; Quintiliani, R.; Nightingale, C. H. Clinical pharmacokinetics of newer cephalosporins. Clinical pharmacokinetics 1995, 28, 361-384.

Larsen, A. R.; Bai, R. Y.; Chung, J. H.; Borodovsky, A.; Rudin, C. M.; Riggins, G. J.; Bunz, F. Repurposing the antihelmintic mebendazole as a hedgehog inhibitor. Mol Cancer Ther 2015, 14, 3-13.

Liu, C. S.; Zhang, H. B.; Jiang, B.; Yao, J. M.; Tao, Y.; Xue, J.; Wen, A. D. Enhanced bioavailability and cysticidal effect of three mebendazole-oil preparations in mice infected with secondary cysts of Echinococcus granulosus. Parasitol Res 2012, 111, 1205-11.

Liu, C. S.; Zhang, H. B.; Lei, W.; Zhang, C. W.; Jiang, B.; Zheng, Q.; Yin, J. H.; Han, X. M. An alternative mebendazole formulation for cystic echinococcosis: the treatment efficacy, pharmacokinetics and safety in mice. Parasit Vectors 2014, 7, 589.

Majer, P.; Jancarik, A.; Krecmerova, M.; Tichy, T.; Tenora, L.; Wozniak, K.; Wu, Y.; Pommier, E.; Ferraris, D.; Rais, R.; Slusher, B. S. Discovery of Orally Available Prodrugs of the Glutamate Carboxypeptidase II (GCPII) Inhibitor 2-Phosphonomethylpentanedioic Acid (2-PMPA). J Med Chem 2016, 59, 2810-9.

Martarelli, D.; Pompei, P.; Baldi, C.; Mazzoni, G. Mebendazole inhibits growth of human adrenocortical carcinoma cell lines implanted in nude mice. Cancer Chemother Pharmacol 2008, 61, 809-817.

Martins, F. T.; Neves, P. P.; Ellena, J.; Cami, G. E.; Brusau, E. V.; Narda, G. E. Intermolecular contacts influencing the conformational and geometric features of the pharmaceutically preferred mebendazole polymorph C. J Pharm Sci 2009, 98, 2336-44.

Mebendazole in Newly Diagnosed High-Grade Glioma Patients Receiving Temozolomide. https://ClinicalTrials.gov/show/NCT01729260

Mukhopadhyay, T.; Sasaki, J.-i.; Ramesh, R.; Roth, J. A. Mebendazole Elicits a Potent Antitumor Effect on Human Cancer Cell Lines Both in Vitro and in Vivo. Clin Cancer Res 2002, 8, 2963-2969.

Nielsen, L. S.; Sloek, F.; Bundgaard, H. N-alkoxycarbonyl prodrugs of mebendazole with increased water solubility. Int J Pharm 1994, 102, 231-9.

Nygren, P.; Fryknäs, M.; Ågerup, B.; Larsson, R. Repositioning of the antihelmintic drug mebendazole for the treatment for colon cancer. J Cancer Res Clin Oncol 2013, 139, 2133-2140.

Pantziarka, P.; Bouche, G.; Meheus, L.; Sukhatme, V.; Sukhatme, V. P. Repurposing Drugs in Oncology (ReDo)—mebendazole as an anti-cancer agent. Ecancer 2014, 8:443.

Phase I Study of Mebendazole Therapy for Recurrent/Progressive Pediatric Brain Tumors. https://ClinicalTrials.gov/show/NCT02644291

Pinto, L. C.; Soares, B. M.; Pinheiro, J. o. d. J. V.; Riggins, G. J.; Assumpção, P. P.; Burbano, R. M. r. R.; Montenegro, R. C. The anthelmintic drug mebendazole inhibits growth, migration and invasion in gastric cancer cell model. Toxicol in Vitro 2015, 29, 2038-2044.

Rodriguez-Caabeiro, F.; Criado-Fornelio, A.; Jimenez-Gonzalez, A.; Guzman, L.; Igual, A.; Perez, A.; Pujol, M. Experimental chemotherapy and toxicity in mice of three mebendazole polymorphic forms. Chemotherapy 1987, 33, 266-71.

Sasaki, J.-i.; Ramesh, R.; Chada, S.; Gomyo, Y.; Roth, J. A.; Mukhopadhyay, T. The anthelmintic drug mebendazole induces mitotic arrest and apoptosis by depolymerizing tubulin in non-small cell lung cancer cells. Mol Cancer Ther 2002, 1, 1201-1209.

Study of the Safety, Tolerability and Efficacy of Metabolic Combination Treatments on Cancer. https://ClinicalTrials.gov/show/NCT02201381

Swanepoel, E.; Liebenberg, W.; de Villiers, M. M. Quality evaluation of generic drugs by dissolution test: changing the USP dissolution medium to distinguish between active and non-active mebendazole polymorphs. Eur J Pharm Biopharm 2003, 55, 345-349.

Ueda, Y.; Matiskella, J. D.; Golik, J.; Connolly, T. P.; Hudyma, T. W.; Venkatesh, S.; Dali, M.; Kang, S. H.; Barbour, N.; Tejwani, R.; Varia, S.; Knipe, J.; Zheng, M.; Mathew, M.; Mosure, K.; Clark, J.; Lamb, L.; Medin, I.; Gao, Q.; Huang, S.; Chen, C. P.; Bronson, J. J. Phosphonooxymethyl prodrugs of the broad spectrum antifungal azole, ravuconazole: synthesis and biological properties. Bioorg Med Chem Lett 2003, 13, 3669-72.

Zhou, L.; Yang, L.; Tilton, S.; Wang, J. Development of a high throughput equilibrium solubility assay using miniaturized shake-flask method in early drug discovery. J Pharm Sci 2007, 96, 3052-71.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound having the structure of formula (I):

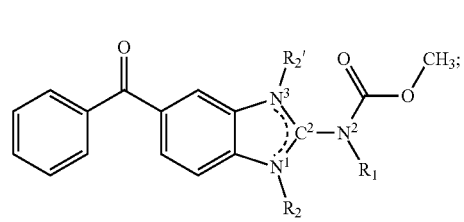

wherein:
$R_2$ or $R_2'$ can be absent or present, provided that at least one of $R_2$ and $R_2'$ is present;
the dashed line indicates a double bond between $N^1$ and $C^2$, in which $R_2'$ is present and $R_2$ is absent, or a double bond between $N^3$ and $C^2$, in which $R_2$ is present and $R_2'$ is absent;

wherein:
$R_2$ is H and $R_1$ is:

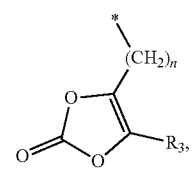

wherein n is an integer selected from 1, 2, 3, 4, 5, 6, 7, and 8, and $R_3$ is $C_1$-$C_6$ straight-chain or branched alkyl, each of which can be substituted; or
$R_1$ is H and $R_2$ or $R_2'$ when present is —$(CR_4R_5)_m$—$R_y$, wherein m is an integer selected from 1, 2, 3, 4, 5, 6, 7, and 8, and wherein —(CR$_4$R$_5$)$_m$—R$_y$ is selected from the group consisting of:

—(CR$_4$R$_5$)$_m$—O—(C═O)—O—R$_6$, wherein C$_4$ and C$_5$ are each H and R$_6$ is C$_1$-C$_6$ straight-chain or branched alkyl;

—(CR$_4$R$_5$)$_m$—O—(C═O)—(CR$_7$R$_8$)$_p$—C(═O)—OR$_9$, wherein R$_4$, R$_5$, R$_7$, R$_8$, and R$_9$ are each H;

—(CR$_4$R$_5$)$_m$—O—(C═O)—O—(CR$_7$R$_8$)$_p$—R$_{10}$ or —(CR$_4$R$_5$)$_m$—O—(C═O)—R$_{10}$, wherein R$_4$, R$_5$, R$_7$, R$_8$, and R$_9$ are each H, and R$_{10}$ is a monosaccharide;

—(CR$_4$R$_5$)$_m$—P(═O)(O$^-$)—O—(CR$_7$R$_8$)$_p$—O—(C═O)—O—R$_6$, wherein R$_4$ and R$_5$ are each H, R$_7$ and R$_8$ are each H or C$_1$-C$_6$ substituted or unsubstituted alkyl, and R$_6$ is C$_1$-C$_6$ straight-chain or branched alkyl; and —(CR$_4$R$_5$)$_m$—O—(C═O)—(CR$_7$R$_8$)$_p$—CR$_{11}$R$_{12}$—C(═O)—OR$_9$; —(CR$_4$R$_5$)$_m$—O—(C═O)—(CR$_7$R$_8$)$_p$—NR$_{15}$—(C═O)—CR$_{16}$R$_{17}$(NR$_{18}$—C(═O)—R$_{19}$), and —(CR$_4$R$_5$)$_m$—R$_{20}$, wherein each R$_4$, R$_5$, R$_7$, and R$_8$ is H, R$_9$, R$_{11}$, R$_{15}$, R$_{16}$, and R$_{18}$ are each H; R$_{12}$ is —NR$_{13}$R$_{14}$, wherein R$_{13}$ and R$_{14}$ are each H; and R$_{17}$ and R$_{19}$ are each C$_1$-C$_6$ straight-chain or branched alkyl; and R$_{20}$ is an amino acid or a substituted amino acid; or a pharmaceutically acceptable salt thereof.

2. The compound of claim 1, wherein R$_2$ is H and R$_1$ is:

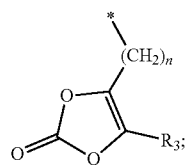

wherein R$_3$ is C$_1$-C$_6$ straight-chain or branched alkyl.

3. The compound of claim 2, wherein the compound of formula (I) has the following structure:

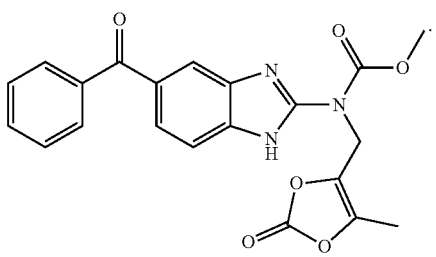 [SMILES: COC(=O)N(Cc1oc(=O)oc1C)c1nc2cc(C(=O)c3ccccc3)ccc2[nH]1]

4. The compound of claim 1, wherein R$_1$ is H and —(CR$_4$R$_5$)$_m$—R$_y$ is —(CR$_4$R$_5$)$_m$—O—(C═O)—O—R$_6$, wherein C$_4$ and C$_5$ are each H and R$_6$ is C$_1$-C$_6$ straight-chain or branched alkyl.

5. The compound of claim 4, wherein the compound of formula (I) has the following structure:

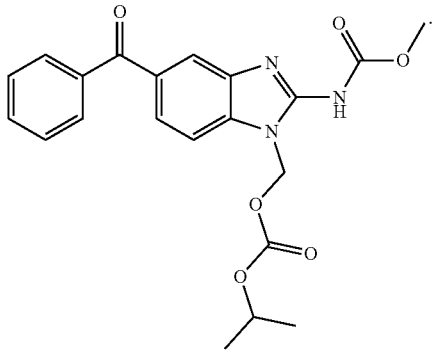 [SMILES: COC(=O)Nc1nc2cc(C(=O)c3ccccc3)ccc2n1COC(=O)OC(C)C]

6. The compound of claim 1, wherein R$_1$ is H and —(CR$_4$R$_5$)$_m$—R$_y$ is —(CR$_4$R$_5$)$_m$—O—(C═O)—(CR$_7$R$_8$)$_p$—C(═O)—OR$_9$, wherein R$_4$, R$_5$, R$_7$, R$_8$, and R$_9$ are each H.

7. The compound of claim 6, wherein the compound of formula (I) has the following structure:

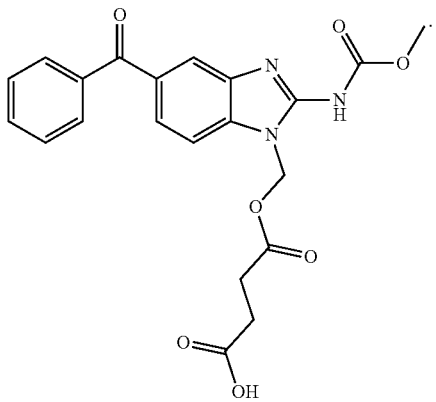 [SMILES: COC(=O)Nc1nc2cc(C(=O)c3ccccc3)ccc2n1COC(=O)CCC(=O)O]

8. The compound of claim 1, wherein R$_1$ is H and —(CR$_4$R$_5$)$_m$—R$_y$ is —(CR$_4$R$_5$)$_m$—O—(C═O)—O—(CR$_7$R$_8$)$_p$—R$_{10}$ or —(CR$_4$R$_5$)$_m$—O—(C═O)—R$_{10}$, wherein R$_4$, R$_5$, R$_7$, R$_8$, and R$_9$ are each H, and R$_{10}$ is a monosaccharide.

9. The compound of claim 8, wherein the compound of formula (I) has the following structure:

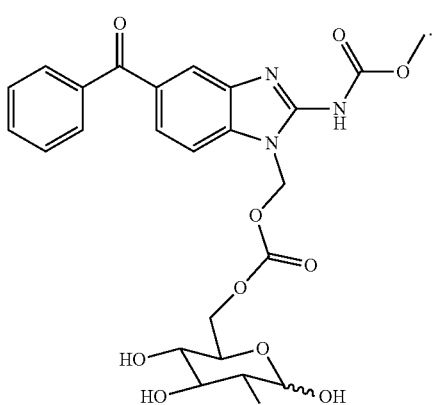

10. The compound of claim 1, wherein R$_1$ is H and —(CR$_4$R$_5$)$_m$—R$_y$ is —(CR$_4$R$_5$)$_m$—P(═O)(O$^-$)—O—

(CR$_7$R$_4$—O—(C=O)—O—R$_6$, wherein R$_4$ and R$_5$ are each H; R$_7$ and R$_8$ are each H or C$_1$-C$_6$ substituted or unsubstituted alkyl; and R$_6$ is C$_1$-C$_6$ straight-chain or branched alkyl.

11. The compound of claim 10, wherein the compound of formula (I) has a structure selected from the group consisting of:

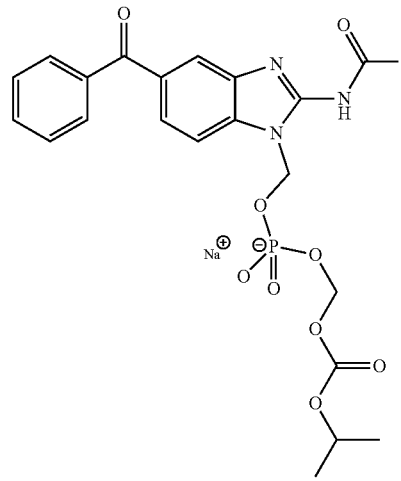

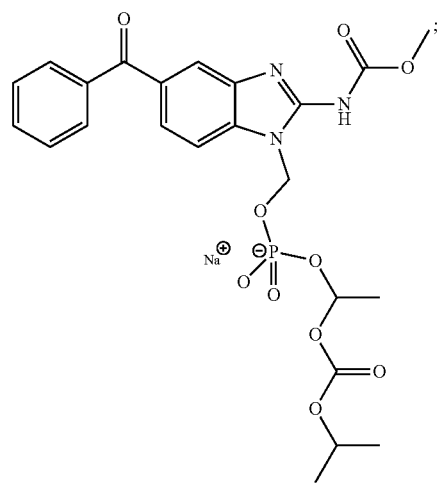

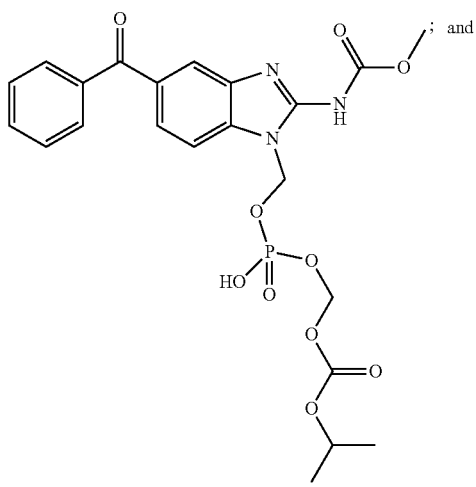

-continued

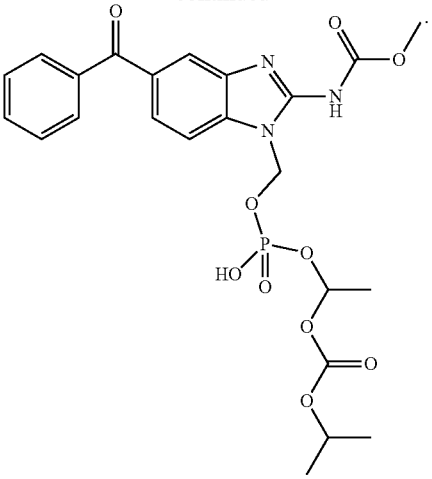 [SMILES: COC(=O)Nc1nc2cc(C(=O)c3ccccc3)ccc2n1COP(=O)(O)OC(C)OC(=O)OC(C)C]

12. The compound of claim 1, wherein R$_1$ is H and —(CR$_4$R$_5$)$_m$—R$_y$ is selected from the group consisting of: —(CR$_4$R$_5$)$_m$—O—(C=O)—(CR$_7$R$_8$)$_p$—CR$_{11}$R$_{12}$—C(=O)—OR$_9$; —(CR$_4$R$_5$)$_m$—O—(C=O)—(CR$_7$R$_8$)$_p$—NR$_{15}$—(C=O)—CR$_{16}$R$_{17}$(NR$_{18}$—C(=O)—R$_{19}$); and —(CR$_4$R$_5$)$_m$—R$_{20}$, wherein each R$_4$, R$_5$, R$_7$, and R$_8$ is H; R$_9$, R$_{11}$, R$_{15}$, R$_{16}$, and R$_{18}$ are each H; R$_{12}$ is —NR$_{13}$R$_{14}$, wherein R$_{13}$ and R$_{14}$ are each H; and R$_{17}$ and R$_{19}$ are each C$_1$-C$_6$ straight-chain or branched alkyl; and R$_{20}$ is an amino acid or a substituted amino acid.

13. The compound of claim 12, wherein the compound of formula (I) is selected from the group consisting of:

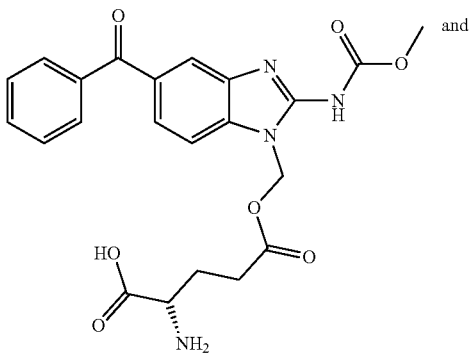

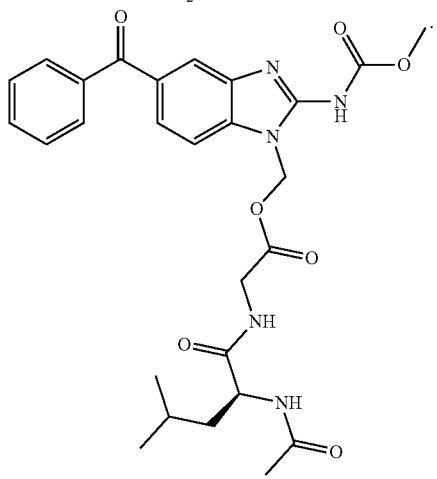

14. The compound of claim 1, wherein the compound of formula (I) is a mixture of $N^1$ and $N^3$ positional isomers.

15. A pharmaceutical composition comprising the compound of claim 1 and a pharmaceutically acceptable carrier, diluent or excipient.

16. The pharmaceutical composition of claim 15, further comprising one or more therapeutic agents selected from the group consisting of a chemotherapeutic agent, a radiotherapeutic agent, an immunotherapeutic agent, and combinations thereof.

17. A method for treating disease, disorder, or condition the method comprising administering to a subject in need of treatment thereof a therapeutically effective amount of a compound of claim 1.

18. The method of claim 17, wherein the disease, disorder, or condition is cancer.

19. The method of claim 18, wherein the cancer is selected from the group consisting of melanoma, non-small cell lung cancer, adrenocortical cancer, colon cancer, breast cancer, leukemia, osteosarcoma, medulloblastomas, and gliomas.

\* \* \* \* \*